(12) United States Patent
Abell et al.

(10) Patent No.: US 8,710,178 B2
(45) Date of Patent: Apr. 29, 2014

(54) MACROCYCLIC CYSTEINE PROTEASE INHIBITORS AND COMPOSITIONS THEREOF

(75) Inventors: Andrew David Abell, Christchurch (NZ); James Morriss Coxon, Christchurch (NZ); Matthew Alan Jones, Christchurch (NZ); Stephen Brian McNabb, Christchurch (NZ); Axel Thomas Neffe, Christchurch (NZ); Steven Geoffrey Aitken, Christchurch (NZ); Blair Gibb Stuart, Christchurch (NZ); Janna Marie Nikkel, Christchurch (NZ); Joanna Kimberley Duncan, Christchurch (NZ); Mutita Klanchantra, Christchurch (NZ); James David Morton, Canterbury (NZ); Roy Bickerstaffe, Canterbury (NZ); Lucinda Jane Goodricke Robertson, Canterbury (NZ); Hannah Yun Young Lee, Christchurch (NZ); Matthew Stewart Muir, Canterbury (NZ)

(73) Assignees: Lincoln University, Lincoln, Canterbury (NZ); Canterprise Limited, Christchurch (NZ); Douglas Pharmaceuticals Limited, Henderson Auckland (NZ)

( * ) Notice: Subject to any disclaimer, the term of this patent is extended or adjusted under 35 U.S.C. 154(b) by 791 days.

(21) Appl. No.: 12/446,053

(22) PCT Filed: Oct. 18, 2007

(86) PCT No.: PCT/NZ2007/000311
§ 371 (c)(1),
(2), (4) Date: Oct. 6, 2010

(87) PCT Pub. No.: WO2008/048121
PCT Pub. Date: Apr. 24, 2008

(65) Prior Publication Data
US 2011/0021434 A1 Jan. 27, 2011

(30) Foreign Application Priority Data
Oct. 18, 2006 (NZ) ........................................ 550631

(51) Int. Cl.
A61K 38/06 (2006.01)
A61P 9/00 (2006.01)
A61P 25/02 (2006.01)
C07K 5/08 (2006.01)

(52) U.S. Cl.
USPC ......... 530/300; 530/331; 514/16.9; 514/17.7; 514/20.2

(58) Field of Classification Search
None
See application file for complete search history.

(56) References Cited

U.S. PATENT DOCUMENTS

2011/0021434 A1* 1/2011 Abell et al. .................. 514/16.9

FOREIGN PATENT DOCUMENTS

| WO | 96/16950 | 6/1996 |
| WO | WO 97/26002 | 7/1997 |
| WO | 01/81325 | 11/2001 |

OTHER PUBLICATIONS

Tholey, J. of Peptide Science, 1997, vol. 3(3), pp. 186-192.*
Written Opinion of the International Searching Authority, dated Mar. 31, 2008, of International Patent Application No. PCT/NZ2007/000311.
Tholey, A. et al., "Solid-phase Synthesis of Tyrosyl H-Phosphonopeptides and Methylphosphonopeptides", Journal of Peptide Science, vol. 3, 186-192 (1997).
Kunz et al., "Synthesis of glycopeptides with the Tn and T antigen structures, and their coupling to bovine serum albumin", Carbohydrate Research, 202 (1990) 207-223.
Rene Beugelmans et al., "An Easy Access to Functionalized Diaryl Ethers: Formal Total Synthesis of K-13," Tetrahedron Letters, vol. 35, No. 31, 1994, pp. 5649-5652.
Dieter Bromme, "Cysteine Proteases as Therapeutic Targets," Drug News Perspect 12(2) Mar. 1999, pp. 73-82.
Manuel Perez-Gonzalez et al., "Pd-catalysed C-C macrocyclisation of a simple tripeptide: efficient total synthesis of K-13," Chem. Commun., 2000, pp. 2423-2424.
Joel D.A. Tyndall et al., "Synthesis, Stability, Antiviral Activity, and Protease-Bound Structures of Substrate Mimicking Constrained Macrocyclic Inhibitors of HIV-1 Protease," J. Med. Chem, vol. 43, 2000, pp. 3495-3504.
Robert C. Reid et al., "Countering Cooperative Effects in Protease Inhibitors Using Constrained Beta-Strand-Mimicking Templates in Focused Combinatorial Libraries," J. Med. Chem., vol. 47, 2004, pp. 1641-1651.
James W. Janetka et al., Novel Cyclic Biphenyl Ether Peptide Beta-Strand Mimetics and HIV-Protease Inhibitors, J. Am. Chem. Soc., vol. 119, 1997, pp. 441-442.
Antonella Marchetti et al., "Synthesis of Two Novel Cyclic Biphenyl Ether Analogs of an Inhibitor of HCV NS3 Protease," Synlett (1999), pp. 1000-1002.
Gilles Quelever et al., "New Beta-strand macrocyclic peptidomimetic analogues containing alpha-(O-, S- or NH-) aryl substituted glycine residues: synthesis, chemical and enzymatic properties," Org. Biomol. Chem., 2003, 1, pp. 1676-1683.

(Continued)

Primary Examiner — Karlheinz R Skowronek
Assistant Examiner — Roy Teller
(74) Attorney, Agent, or Firm — Dann, Dorfman, Herrell and Skillman, P.C.

(57) ABSTRACT

The present invention provides a novel class of macrocyclic compounds, which are useful as cysteine protease inhibitors. Also provided are novel intermediates and methods of preparing the compounds. The invention also provides pharmaceutical compositions comprising the compounds. The compounds and compositions are useful in methods of treating or preventing one or more diseases associated with cysteine protease activity, particularly those associated with calpain activity.

5 Claims, 2 Drawing Sheets

(56) References Cited

OTHER PUBLICATIONS

Julie Sanderson et al., "A Human Lens Model of Cortical Cataract: Ca2+ -Induced Protein Loss, Vimentin Cleavage and Opacification," Investigative Ophthalmology & Visual Science, Jul. 2000, vol. 41, No. 8, pp. 2255-2261.

Valery F. Thompson et al., "A BODIPY Fluorescent Microplate Assay for Measuring Activity of Calpains and Other Proteases," Analytical Biochemistry, 279, (2000), pp. 170-178.

Kevin K.W. Wang et al., "Calpain inhibition: an overview of its therapeutic potential," Trends Pharmacol. Sci., vol. 15, Nov. 1994, pp. 412-419.

* cited by examiner

MACROCYCLIC CYSTEINE PROTEASE INHIBITORS AND COMPOSITIONS THEREOF

TECHNICAL FIELD

This invention relates to compounds with enzyme inhibitory activity and to compositions that comprise one or more of these compounds. In particular, the invention relates to compounds that inhibit cysteine proteases, particularly calpains. These compounds have utility in the treatment of a variety of diseases.

BACKGROUND ART

A protease is an enzyme that degrades proteins into smaller peptide fragments. Cysteine proteases incorporate a cysteine residue that is essential to the catalytic process.

Calpains are cysteine proteases that are activated by elevated levels of intracellular calcium ions. Under normal circumstances, calcium ion signalling of calpain leads to controlled proteolysis during cytoskeletal remodelling, signal transduction and apoptosis in mammals. Uncontrolled or high levels of calcium ions in a cell can cause excessive calpain activity, and lead to tissue damage.

There are two major isoforms of calpain, which require different concentrations of calcium ions for activity. They are μ-calpain (also known as calpain I or calpain 1) and m-calpain (also known as calpain II or calpain 2). The μ-calpain isoform has been identified as the major isoform present during pathological conditions of the nervous system such as Alzheimer's disease, motor neuron damage, muscular dystrophy and stroke.

The m-calpain isoform has been associated with the development of cataracts. Cataracts are a condition whereby the lens of an eye becomes increasingly clouded and eventually results in blindness. The clouding is due to the precipitation of degraded lens proteins that results from sustained activity of the calcium ion-activated calpain.

Several classes of calpain inhibitors are known. However, many of the known calpain inhibitors have limited therapeutic potential because they have poor stability, cell permeability, solubility or selectivity, or because they have high cell toxicity.

Accordingly, it is an object of the present invention to go some way to avoiding the above disadvantages or to at least provide the public with a useful choice.

Other objects of the invention may become apparent from the following description which is given by way of example only.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date.

SUMMARY OF THE INVENTION

In a first aspect, the present invention provides a compound of Formula I or a pharmaceutically acceptable salt, solvate, hydrate or prodrug derivative thereof:

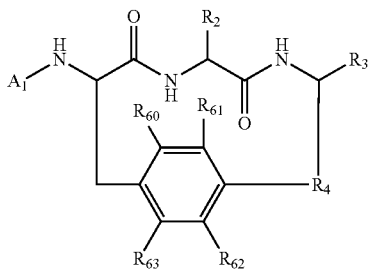

Formula I wherein;

A is —C(=O)R$_5$ or —S(=O)$_2$R$_6$;
  wherein R$_5$ is optionally substituted C$_1$-C$_6$ alkyl, optionally substituted aryl, optionally substituted heteroaryl, optionally substituted aryloxy, optionally substituted heteroaryloxy, optionally substituted arylalkoxy or optionally substituted heteroarylalkoxy; and
  R$_6$ is optionally substituted C$_1$-C$_6$ alkyl, optionally substituted aryl, optionally substituted heteroaryl, optionally substituted aryloxy, optionally substituted heteroaryloxy, optionally substituted arylalkoxy or optionally substituted heteroarylalkoxy;
R$_2$ is a side chain of a natural or non-natural alpha-amino acid;
R$_3$ is —CH$_2$OH, —CH$_2$OR$_7$, —CH$_2$N$_3$, —CH$_2$NR$_8$R$_9$, —CH(OH)R$_{10}$, —CHO, —CH(OH)C(=O)NR$_{11}$R$_{12}$, —C(=O)C(=O)NR$_{11}$R$_{12}$, or —C(=O)R$_{13}$;
  wherein R$_7$ is C$_1$-C$_6$ alkyl, aryl or arylalkyl;
  R$_8$ is hydrogen, C$_1$-C$_6$ alkyl, aryl or arylalkyl;
  R$_9$ is hydrogen, C$_1$-C$_6$ alkyl, aryl or arylalkyl;
  R$_{10}$ is C$_1$-C$_6$ alkyl, alkoxy, thioalkoxy, aryl, arylalkyl, heteroaryl, heteroarylalkyl or cyano;
  R$_{11}$ and R$_{12}$ are each independently selected from hydrogen, C$_1$-C$_6$ alkyl, hydroxyalkyl, aryl, arylalkyl, heterocyclyl, heterocyclylalkyl, heteroaryl and heteroarylalkyl; or R$_{11}$ and
  R$_{12}$ taken together with the nitrogen to which they are attached form a heterocyclyl or heteroaryl; and
  R$_{13}$ is C$_1$-C$_6$ alkyl, aryl, arylalkyl, heteroaryl or heteroarylalkyl;
R$_4$ is —O—R$_{20}$— which is attached to the 1,4-phenylene ring through the oxygen atom;
  wherein R$_{20}$ is optionally substituted straight chain —(C$_3$-C$_6$)-alkyl- or optionally substituted straight chain —(C$_3$-C$_6$)-alkenyl-; wherein any one methylene group within the straight chain —(C$_3$-C$_6$)-alkyl- or straight chain —(C$_3$-C$_6$)-alkenyl-, except the methylene group adjacent to the oxygen atom to which R$_{20}$ is attached, may be replaced by an oxygen, nitrogen or sulfur heteroatom or a —S(=O)— or —S(=O)$_2$— group; and wherein any two carbon atoms, or a carbon atom and a nitrogen heteroatom, if present, of the straight chain —(C$_3$-C$_6$)-alkyl- or straight chain —(C$_3$-C$_6$)-alkenyl- may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl; and
R$_{60}$, R$_{61}$, R$_{62}$ and R$_{63}$ are each independently selected from hydrogen, halogen, —NH$_2$, —NO$_2$, —OH, C$_1$-C$_6$ alkyl and C$_1$-C$_6$ alkoxy.

The present invention also provides a compound of Formula II or a salt, solvate or hydrate thereof:

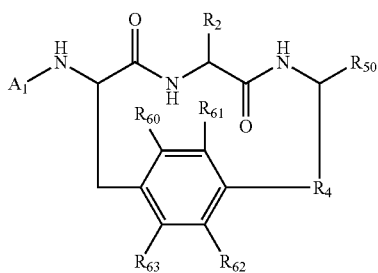

Formula II wherein;
$R_{50}$ is —C(=O)O—$R_{40}$;
$R_{40}$ is alkyl, benzyl, allyl, dialkylphenyl or silyl;
$A_1$ is hydrogen, an amino protecting group or A; and
A, $R_2$, $R_4$, $R_{60}$, $R_{61}$, $R_{62}$ and $R_{63}$ are as defined for Formula I.

The present invention also provides a compound of Formula III or a salt, solvate or hydrate thereof:

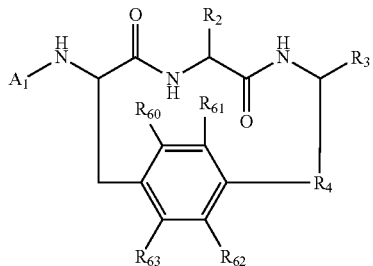

Formula III wherein;
$A_1$ is hydrogen or an amino protecting group; and
$R_2$, $R_3$, $R_4$, $R_{60}$, $R_{61}$, $R_{62}$ and $R_{63}$ are as defined for Formula I.

The present invention also provides a compound of Formula IV or a salt, solvate or hydrate thereof:

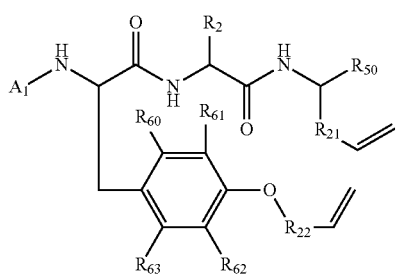

Formula IV wherein;
$R_{21}$ is optionally substituted straight chain ($C_m$)-alkyl; and
$R_{22}$ is optionally substituted straight chain ($C_n$)-alkyl;
wherein m=0-4 and n=0-4; provided that the sum m+n=1-4; and wherein any one methylene group of $R_{21}$ and $R_{22}$, except that adjacent to the oxygen atom to which $R_{22}$ is attached may be replaced by an oxygen, nitrogen or sulfur heteroatom or a —S(=O)— or —S(=O)$_2$— group; and wherein any two carbon atoms, or a carbon atom and a nitrogen atom, if present, of $R_{21}$ may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl, or any two carbon atoms, or a carbon atom and a nitrogen atom, if present, of $R_{22}$ may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl;
$A_1$ is hydrogen, an amino protecting group or A; and
A, $R_2$, $R_{60}$, $R_{61}$, $R_{62}$ and $R_{63}$ are, as defined for Formula I and $R_{50}$ is as defined for Formula II.

The present invention also provides a compound of Formula V or a salt, solvate or hydrate thereof:

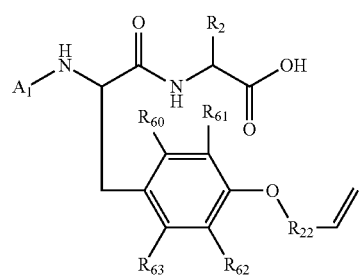

Formula V wherein $R_2$, $R_{60}$, $R_{61}$/$R_{62}$ and $R_{63}$ are as defined for Formula I and $A_1$ and $R_{22}$ are as defined for Formula IV.

The present invention also provides a compound of Formula VI or a salt, solvate or hydrate thereof:

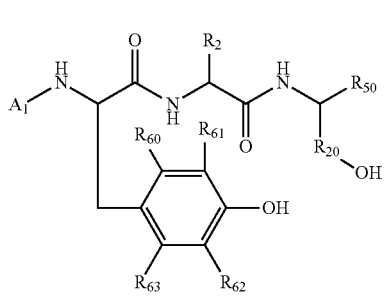

Formula VI wherein $A_1$ is hydrogen, an amino protecting group or A; and
A, $R_2$, $R_{20}$, $R_{60}$, $R_{61}$, $R_{62}$ and $R_{63}$ are as defined for Formula I and $R_{50}$ is as defined for Formula II.

The present invention also provides the compound (S)-2-[(S)-3-(4-allyloxy-phenyl)-2-(4-fluoro-benzenesulfonylamino)-propionylamino]-4-methyl-pentanoic acid methyl ester:

(11)

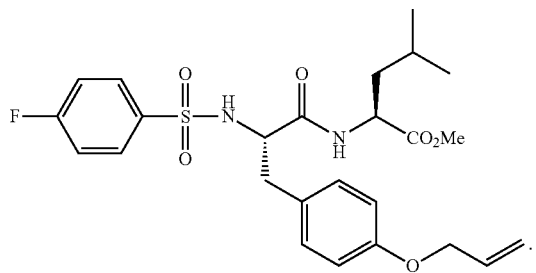

The present invention also provides the compound (S)-3-(4-but-3-enyloxy-phenyl)-2-tert-butoxycarbonylamino-propionic acid methyl ester:

(18)

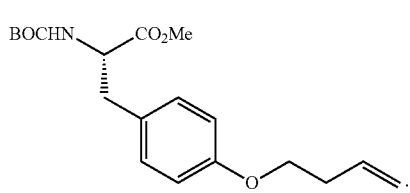

The present invention also provides the compound (S)-3-(4-but-3-enyloxy-phenyl)-2-tert-butoxycarbonylamino-propionic acid:

(19)

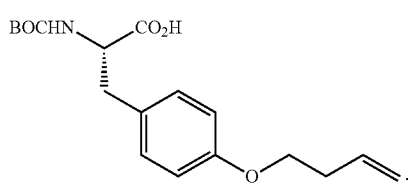

The present invention also provides the compound (S)-2-[(S)-3-(4-but-3-enyloxy-phenyl)-2-tert-butoxycarbonylamino-propionylamino]-4-ethyl-pentanoic acid methyl ester:

(20)

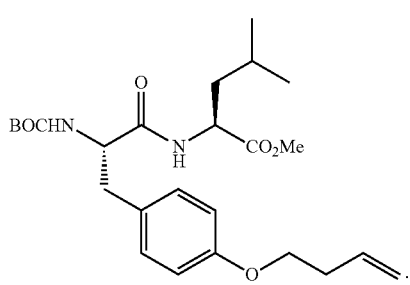

The present invention also provides the compound (S)-6-hydroxy-2-{(S)-2-[(S)-3-(4-hydroxy-phenyl)-2-methyl-propionylamino]-4-methyl-pentanoylamino}-hexanoic acid methyl ester:

(83)

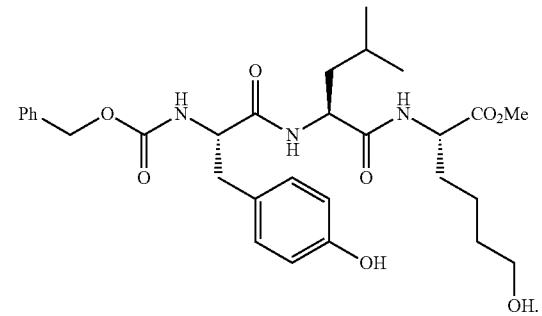

The present invention also provides a process for preparing a compound of Formula I:

Formula I

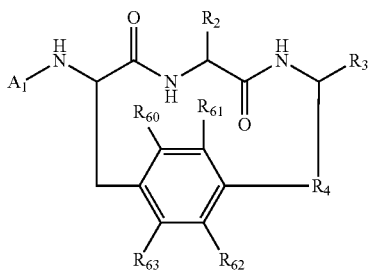

the process comprising the steps of:
(a) cyclising a compound of Formula VI:

Formula VI

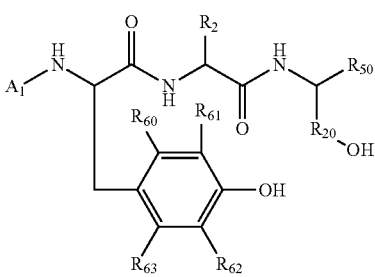

to provide a compound of Formula II:

Formula II

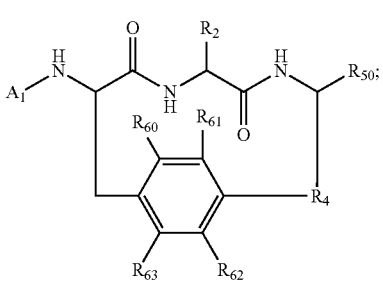

and
(b) converting the compound of Formula II into the compound of Formula I.

In one embodiment, the process further comprises the steps of:
(a) providing a compound of Formula VII:

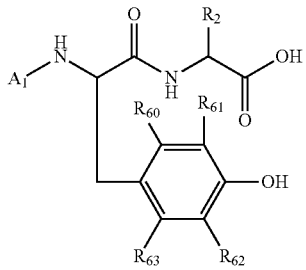

Formula VII or an activated acid derivative thereof, wherein $A_1$ is hydrogen, an amino protecting group or A; and
A, $R_2$, $R_{60}$, $R_{61}$, $R_{62}$ and $R_{63}$ are as defined for Formula I; and
(b) coupling the compound of Formula VII with a compound of Formula VIII:

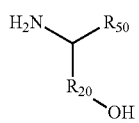

Formula VIII or an activated amino derivative thereof, wherein $R_{20}$ is as defined for Formula I and $R_{50}$ is as defined for Formula II, to provide the compound of Formula VI.

The present invention also provides a process for preparing a compound of Formula I:

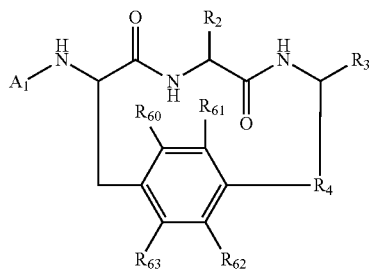

Formula I the process comprising the steps of:
(a) cyclising a compound of Formula IV:

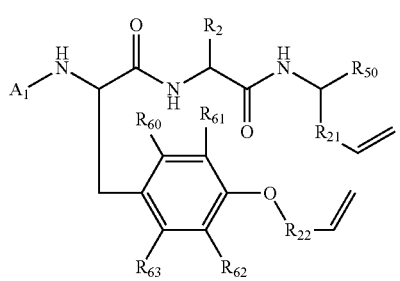

Formula IV to provide a compound of Formula II:

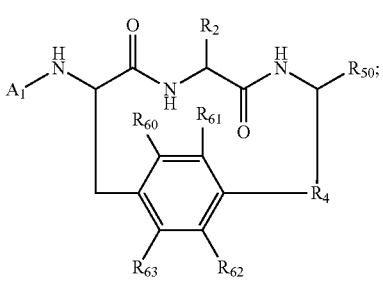

Formula II and
(b) converting the compound of Formula II into the compound of Formula I.

In one embodiment, the process further comprises the steps of:
(a) providing a compound of Formula V:

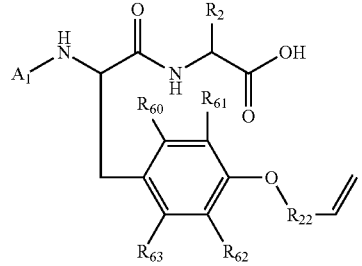

Formula V or an activated acid derivative thereof; and
(b) coupling the compound of Formula V with a compound of Formula IX:

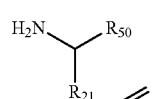

Formula IX or an activated amino derivative thereof, wherein $R_{21}$ is as defined for Formula IV and $R_{50}$ is as defined for Formula II, to provide the compound of Formula IV.

In another aspect, the present invention provides a compound of Formula I for use as a medicament.

In another aspect, the present invention provides a compound of Formula I for use as a cysteine protease inhibitor.

In another aspect, the present invention provides a method for inhibiting a cysteine protease in a mammal comprising the step of administering a compound of Formula I to the mammal.

In another aspect, the present invention provides a method for the treatment or prophylaxis of a disease or disorder resulting from excessive cysteine protease activity in a mammal comprising the step of administering a compound of Formula I to the mammal.

In another aspect, the present invention provides an in vitro method for inhibiting a cysteine protease comprising contacting the cysteine protease with a compound of Formula I.

In another aspect, the present invention provides a method of inhibiting a cysteine protease in a cell comprising contacting the cell with an effective amount of a compound of Formula I.

In another aspect, the present invention provides a use of a compound of Formula I for the manufacture of a medicament for reducing the activity of a cysteine protease.

In another aspect, the present invention provides a use of a compound of Formula I for the manufacture of a medicament for the treatment or prophylaxis of a disease or disorder resulting from excessive cysteine protease activity.

In another aspect, the present invention provides a method for the treatment or prophylaxis of cataracts in a mammal comprising the step of administering a compound of Formula I to the mammal.

In another aspect, the present invention provides a use of a compound of Formula I for the manufacture of a medicament for the treatment or prophylaxis of cataracts.

In another aspect, the present invention provides a composition comprising a compound of Formula I.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The term "comprising", or variations such as "comprises", as used in this specification and claims means "consisting at least in part of". That is to say when interpreting statements in this specification and claims which include that term, the features prefaced by that term in each statement all need to be present but other features can also be present.

Although the present invention is broadly as defined above, those persons skilled in the art will appreciate that the invention is not limited thereto and that the invention also includes embodiments of which the following description gives examples.

BRIEF DESCRIPTION OF THE DRAWINGS

The invention will now be described with reference to the Figures in which.

DETAILED DESCRIPTION OF THE INVENTION

Figure 1:
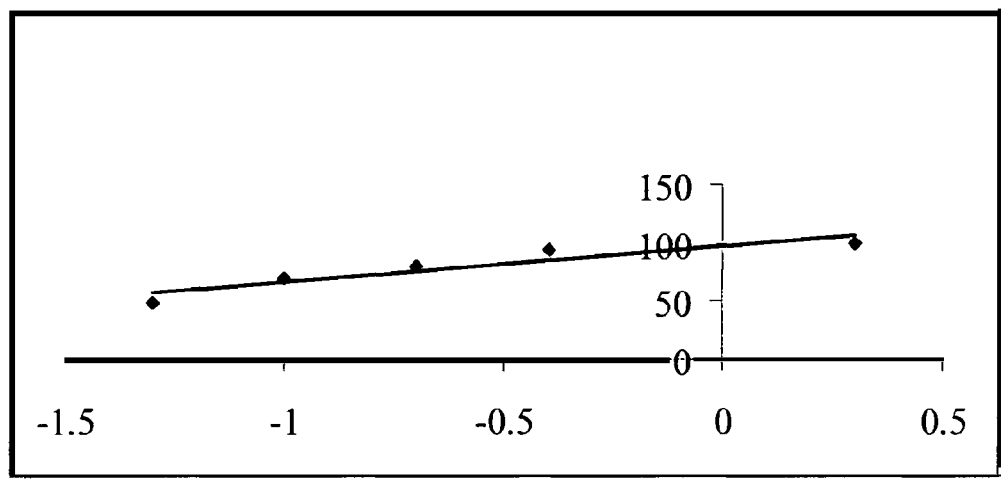
FIG. 1 is a graph of the results of a fluorescence-based assay of the inhibition of m-calpain activity by (7S,10S,13S)-7-formyl-10-isobutyl-9,12-dioxo-2-oxa-8,11-diaza-bicyclo[13.2.2]-nonadeca-1(18),15(19),16-trien-13-yl)-carbamic acid benzyl ester (9)

In a first aspect, the present invention provides a compound of Formula I or a pharmaceutically acceptable salt, solvate, hydrate or prodrug derivative thereof:

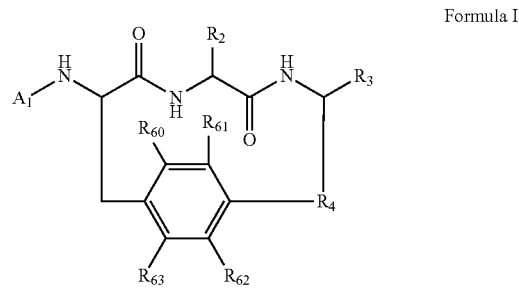

Formula I wherein;

A is —C(=O)$R_5$ or —S(=O)$_2R_6$;
  wherein $R_5$ is optionally substituted $C_1$-$C_6$ alkyl, optionally substituted aryl, optionally substituted heteroaryl, optionally substituted aryloxy, optionally substituted heteroaryloxy, optionally substituted arylalkoxy or optionally substituted heteroarylalkoxy; and
  $R_6$ is optionally substituted $C_1$-$C_6$ alkyl, optionally substituted aryl, optionally substituted heteroaryl, optionally substituted aryloxy, optionally substituted heteroaryloxy, optionally substituted arylalkoxy or optionally substituted heteroarylalkoxy;

$R_2$ is a side chain of a natural or non-natural alpha-amino acid;
$R_3$ is —$CH_2OH$, —$CH_2OR_7$, —$CH_2N_3$, —$CH_2NR_8R_9$, —CH(OH)$R_{10}$, —CHO, —CH(OH)C(=O)$NR_{11}R_{12}$, —C(=O)C(=O)$NR_{11}R_{12}$, or —C(=O)$R_{13}$;
  wherein $R_7$ is $C_1$-$C_6$ alkyl, aryl or arylalkyl;
  $R_8$ is hydrogen, $C_1$-$C_6$ alkyl, aryl or arylalkyl;
  $R_9$ is hydrogen, $C_1$-$C_6$ alkyl, aryl or arylalkyl;
  $R_{10}$ is $C_1$-$C_6$ alkyl, alkoxy, thioalkoxy, aryl, arylalkyl, heteroaryl, heterocyclylalkyl or cyano;
  $R_{11}$ and $R_{12}$ are each independently selected from hydrogen, $C_1$-$C_6$ alkyl, hydroxyalkyl, aryl, arylalkyl, heterocyclyl, heterocyclylalkyl, heteroaryl and heteroarylalkyl; or $R_{11}$ and $R_{12}$ taken together with the nitrogen to which they are attached form a heterocyclyl or heteroaryl; and $R_{13}$ is $C_1$-$C_6$ alkyl, aryl, arylalkyl, heteroaryl or heteroarylalkyl;

$R_4$ is —O—$R_{20}$— which is attached to the 1,4-phenylene ring through the oxygen atom;

wherein $R_{20}$ is optionally substituted straight chain —($C_3$-$C_6$)-alkyl- or optionally substituted straight chain —($C_3$-$C_6$)-alkenyl-; wherein any one methylene group within the straight chain —($C_3$-$C_6$)-alkyl- or straight chain —($C_3$-$C_6$)-alkenyl-, except the methylene group adjacent to the oxygen atom to which $R_{20}$ is attached, may be replaced by an oxygen, nitrogen or sulfur heteroatom or a —S(=O)— or —S(=O)$_2$— group; and wherein any two carbon atoms, or a carbon atom and a nitrogen heteroatom, if present, of the straight chain —($C_3$-$C_6$)-alkyl- or straight chain —($C_3$-$C_6$)-alkenyl- may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl; and $R_{60}$, $R_{61}$, $R_{62}$ and $R_{63}$ are each independently selected from hydrogen, halogen, —NH$_2$, —NO$_2$, —OH, $C_1$-$C_6$ alkyl and $C_1$-$C_6$ alkoxy.

As used herein, the term "side chain of a natural or non-natural alpha-amino acid" means the group $R_4$ in a natural or non-natural amino acid of formula NH$_2$—CH($R_4$)—COOH.

As used herein, the term "natural alpha-amino acid" includes the 20 L-amino acids (or a residue thereof) which commonly comprise most polypeptides in living systems, that is: alanine (Ala); arginine (Arg); asparagine (Asn); aspartic acid (Asp); cysteine (Cys); glutamine (Gln); glutamic acid (Glu); glycine (Gly); histidine (His); isoleucine (Ileu); leucine (Leu); lysine (Lys); methionine (Met); phenylalanine (Phe); proline (Pro); serine (Ser); threonine (Thr); tryptophan (Trp); tyrosine (Tyr); and valine (Val). The term also includes rarer amino acids found in fibrous proteins (for example, 4-hydroxyproline, 5-hydroxylysine, N-methyllysine, 3-methylhistidine, desmosine and isodesmosine), and naturally occurring amino acids not found in proteins (for example, gamma-aminobutyric acid, homocysteine, homoserine, citrulline, ornithine, canavanine, djenkolic acid and beta-cyanoalanine).

Natural alpha-amino acids which contain functional substituents, for example amino, carboxyl, hydroxy, mercapto, guanidyl, imidazolyl or indolyl groups in their characteristic side chains include arginine, lysine, glutamic acid, aspartic acid, tryptophan, histidine, serine, threonine, tyrosine and cysteine. When $R_1$ and/or $R_2$ in the compounds of the invention is a side chain that includes a functional substituent, such as a side chain of one of those natural alpha-amino acids, the functional substituent may optionally be protected. Suitable protecting groups are known to those skilled in the art.

As used herein, the term "non-natural alpha-amino acid" includes any alpha-amino acid (or residue thereof) other than the natural amino acids listed above. Non-natural amino acids include the D-isomers of the natural L-amino acids. Non-natural amino acids also include, but are not limited to: D-phenylalanine; norleucine; hydroxyproline; alpha-carboxyglutamic acid; and pyroglutamic acid.

The prefixes "D-" or "L-" indicate an alpha-amino acid of D- or L-configuration respectively. A "D.L-" prefix indicates a racemic mixture of amino acids of the two configurations. Where no prefix is included, this means that the amino acid can be of either the D- or the L-configuration, except in the Examples where residues are of L-configuration unless otherwise stated.

As used herein, the term "pharmaceutically acceptable salt" is intended to include acid addition salts of any basic moiety that may be present in a compound of Formula I, and base addition salts of any acidic moiety that may be present in a compound of Formula I. Such salts are generally prepared by reacting the compound with a suitable organic or inorganic acid or base. Examples of pharmaceutically acceptable salts of basic moieties include: sulfates; methanesulfonates; acetates; hydrochlorides; hydrobromides; phosphates; toluenesulfonates; citrates; maleates; succinates; tartrates; lactates; and fumarates. Examples of pharmaceutically acceptable salts of acidic moieties include: ammonium salts; alkali metal salts such as sodium salts and potassium salts; and alkaline earth metal salts such as calcium salts and magnesium salts. Other pharmaceutically acceptable salts will be apparent to those skilled in the art.

As used herein, the term "prodrug derivative" is intended to include functional derivatives of the compounds of Formula I, the pharmacological action of which results from conversion to a compound of Formula I by metabolic processes within the body. Therefore, a prodrug derivative is any covalently bonded carrier that releases a compound of Formula I in vivo when the prodrug derivative is administered to a mammal. Prodrug derivatives are generally prepared by modifying functional groups in such a way that the modification is cleaved in vivo to yield the parent compound. Conventional procedures for the selection and preparation of suitable prodrug derivatives are known to those persons skilled in the art and are discussed in, for example, T. Higuchi and V. Stella, *Pro-drugs as Novel Delivery Systems*, volume 14 of the A.C.S. Symposium Series, 1987, and E. B. Roche (ed.), *Bioreversible Carriers in Drug Design*, Pergamon Press, New York, 1987.

The compounds of Formula I may form hydrates, or solvates with pharmaceutically acceptable solvents. The present invention contemplates such hydrates and solvates as well as the corresponding unsolvated forms.

As used herein, the term "optionally substituted" is intended to mean that one or more hydrogen atoms in the group indicated is replaced with one or more independently selected suitable substituents, provided that the normal valency of each atom to which the optional substituent/s are attached is not exceeded, and that the substitution results in a stable compound.

Unless a moiety of a compound is defined as being unsubstituted, that moiety may be optionally substituted. In a preferred embodiment, the optional substituents are independently selected from the group consisting of alkyl, alkoxyalkyl, aminoalkyl, haloalkyl, hydroxyalkyl, alkenyl, alkynyl, alkoxy, haloalkoxy, aryl, arylalkyl, arylalkoxy, aryloxy, heterocyclyl, heterocyclylalkyl, heteroaryl, heteroarylalkoxy, heteroarylalkyl, heteroaryloxy, carboxy, oxo, acyl, amido, nitro, cyano, hydroxyl and halo; —O(C=O)—$R^x$, —C(=O)O—$R^x$, —C(=O)—$R^x$, NH—C(=O)—$R^x$, —S(=O)—$R^x$ and S(=O)$_2$—$R^x$, wherein each $R^x$ is independently selected from alkyl, aryl, heterocyclyl and heteroaryl; —NR$^y$R$^z$, -alkyl-NR$^y$R$^z$, —C(=O)—NR$^y$R$^z$, —S(=O)—NR$^y$R$^z$ and —S(=O)$_2$—NR$^y$R$^z$, wherein each R$^y$ and R$^z$ is independently selected from hydrogen, alkyl, aryl, heterocyclyl and heteroaryl.

The general chemical terms used in the formulae herein have their usual meanings. For example:

As used herein, the term "alkyl" is intended to include straight chain, branched chain or cyclic saturated hydrocarbon groups. In one embodiment, preferred alkyl groups comprise 1 to 6 carbon atoms. In another preferred embodiment, the alkyl group is methyl, ethyl, n-propyl, iso-propyl, cyclopropyl, n-butyl, iso-butyl, tert-butyl or cyclobutyl.

As used herein, the term "alkenyl" is intended to include straight chain, branched chain or cyclic mono-unsaturated hydrocarbon groups As used herein, the term "alkoxy" is intended to include the groups alkyl-O— where alkyl is as defined above.

As used herein, the term "aryl" is intended to include aromatic radicals including, but not limited to: phenyl; naphthyl; indanyl; biphenyl; and the like. In one embodiment, preferred aryl groups comprise 4 to 10 carbon atoms.

As used herein, the term "aryloxy" is intended to include the groups aryl-O— where aryl is as defined above.

As used herein, the term "arylalkoxy" is intended to include the groups aryl-alkyl-O— where alkyl and aryl are as defined above.

As used herein, the term "arylalkyl" is intended to include the groups aryl-alkyl- where alkyl and aryl are as defined above.

As used herein, the term "heteroaryl" is intended to include heteroaromatic radicals including, but not limited to: pyrimidinyl; pyridyl; pyrrolyl; furyl; oxazolyl; thiophenyl; and the like.

As used herein, the term "heteroaryloxy" is intended to include the groups heteroaryl-O— where heteroaryl is as defined above.

As used herein, the term "heteroarylalkoxy" is intended to include the groups heteroaryl-alkyl-O— where alkyl and heteroaryl are as defined above.

As used herein, the term "heteroarylalkyl" is intended to include the groups heteroaryl-alkyl- where alkyl and heteroaryl are as defined above.

As used herein, the term "heterocyclyl" is intended to include non-aromatic saturated heterocyclic radicals including, but not limited to: piperidinyl; pyrrolidinyl; piperazinyl; 1,4-dioxanyl; tetrahydrofuranyl; tetrahydrothiophenyl; and the like.

As used herein, the term "heterocyclylalkyl" is intended to include the groups heterocyclyl-alkyl- where alkyl and heterocyclyl are as defined above.

As used herein, the term "thioalkoxy" is intended to include the groups alkyl-S— where alkyl is as defined above.

In one embodiment wherein $R_5$ or $R_6$ comprises a substituted aryl or heteroaryl group, the substituent/s on the aryl or heteroaryl group are independently selected from —$NH_2$, —OH, alkyl, alkoxy, preferably methoxy, and halogen.

In one embodiment wherein $R_{10}$ comprises a substituted aryl or heteroaryl group, the substituent/s on the aryl or heteroaryl group are independently selected from alkyl, alkoxy and halogen.

In a preferred embodiment wherein A is —C(=O)$R_5$, $R_5$ is optionally substituted arylalkoxy. More preferably, $R_5$ is benzyloxy.

In a preferred embodiment wherein A is —C(=O)$R_5$, $R_5$ is optionally substituted aryl or heteroaryl. More preferably, $R_5$ is 2-pyrrolyl.

In a preferred embodiment wherein A is —S(=O)$_2R_6$, $R_6$ is optionally substituted $C_1$-$C_6$ alkyl. In a further preferred embodiment, $R_6$ is methyl.

In a preferred embodiment wherein A is —S(=O)$_2R_6$, $R_6$ is optionally substituted aryl. In a further preferred embodiment, $R_6$ is substituted phenyl. More preferably, $R_6$ is halophenyl, more preferably, 4-fluorophenyl.

In a preferred embodiment, $R_2$ is a hydrophobic side chain of a natural or non-natural alpha-amino acid.

In a preferred embodiment, $R_2$ is a side chain of a natural alpha-amino acid.

In a preferred embodiment, $R_2$ is alkyl.

In a preferred embodiment, $R_2$ is a side chain of L-leucine or L-valine.

In one embodiment wherein $R_3$ is —CH(OH)C(=O)$NR_{11}R_{12}$ or —C(=O)C(=O)$NR_{11}R_{12}$, $R_{11}$ and $R_{12}$ taken together with the nitrogen atom to which they are attached form a heterocyclyl.

In a preferred embodiment wherein $R_3$ is —CH(OH)C(=O)$NR_{11}R_{12}$ or —C(=O)C(=O)$NR_{11}R_{12}$, one of $R_{11}$ and $R_{12}$ is hydrogen.

In a preferred embodiment wherein $R_3$ is —CH(OH)C(=O)$NR_{11}R_{12}$ or —C(=O)C(=O)$NR_{11}R_{12}$, $R_{11}$ is $C_1$-$C_6$ alkyl and $R_{12}$ is hydrogen. More preferably, $R_{11}$ is cyclopropyl, ethyl or methyl.

In a preferred embodiment wherein $R_3$ is —$CH_2NR_8R_9$, one of $R_8$ or $R_9$ is cyclopropyl.

In a preferred embodiment, $R_3$ is —$CH_2OH$ or —CHO.

In a preferred embodiment, $R_{20}$ is unsubstituted straight chain $C_3$-$C_6$-alkyl.

In a preferred embodiment, $R_{20}$ is unsubstituted straight chain $C_3$-$C_6$-alkenyl.

In a preferred embodiment, $R_{20}$ is unsubstituted straight chain $C_3$-$C_6$-alkyl wherein one of the methylene groups has been replaced by —O— or —S—.

In one embodiment, wherein $R_{20}$ includes a fused ring, the fused ring includes 3 to 8 ring members, more preferably 3 to 6 ring members.

In a particularly preferred embodiment, $R_4$ is —O-propyl-, —O-butyl-, —O-pentyl-, —O—$(CH_2)_4OCH_2$— or —O—$(CH_2)_4SCH_2$—.

In a preferred embodiment wherein $R_3$ is —CH(OH)$R_{10}$, $R_{10}$ is alkoxy or thioalkoxy. More preferably, $R_{10}$ is alkoxy. Still more preferably, $R_{10}$ is $C_{16}$-$C_{18}$-alkoxy.

In another preferred embodiment wherein $R_3$ is —CH(OH)$R_{10}$, $R_{10}$ is cyano.

In a preferred embodiment, $R_{60}$, $R_{61}$, $R_{62}$ and $R_{63}$ are each hydrogen.

A preferred group of compounds of Formula I has the following stereochemistry:

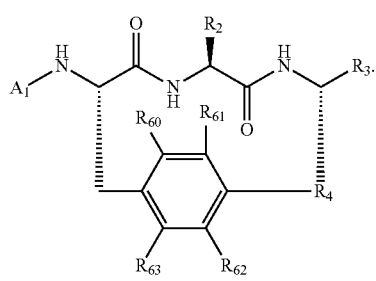

Another preferred group of compounds of Formula I has the following structural formula:
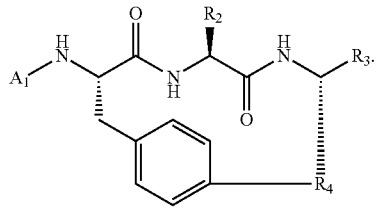
A particularly preferred group of compounds of Formula I consists of:
8
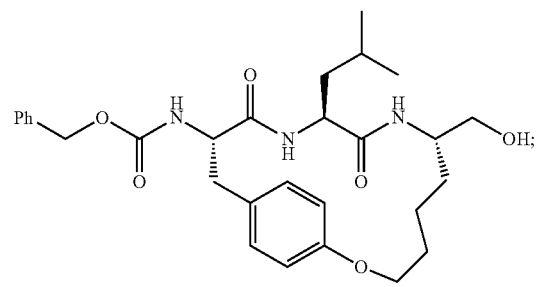
9
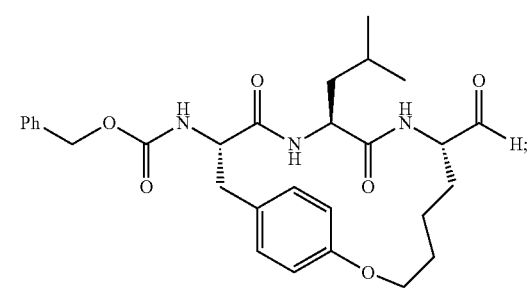
16
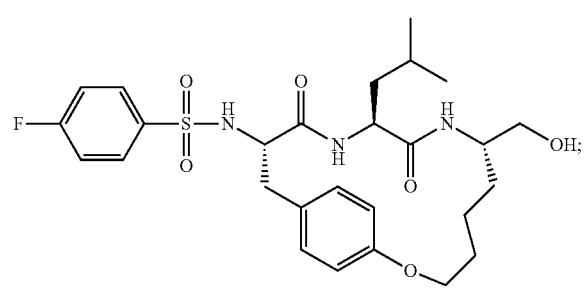
17
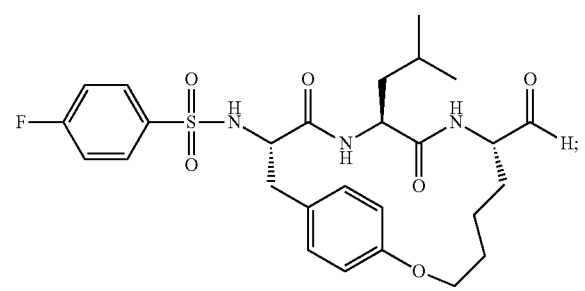
27
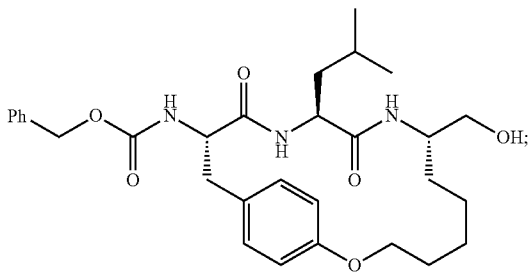
28
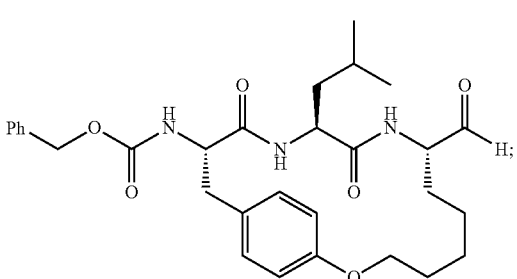
36
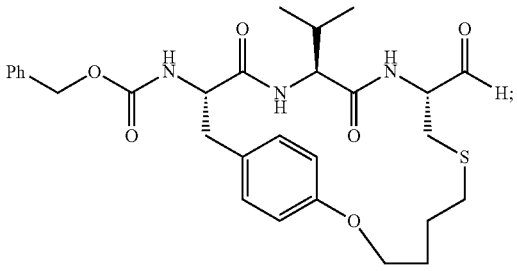
49
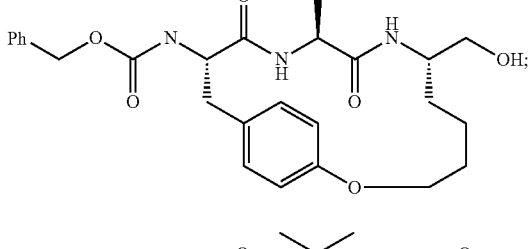
50
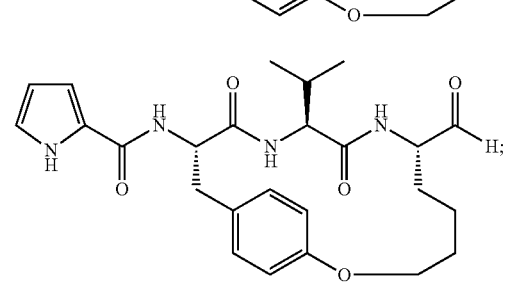
52

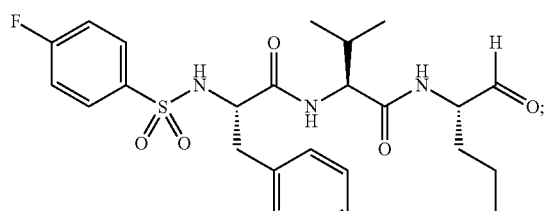
54
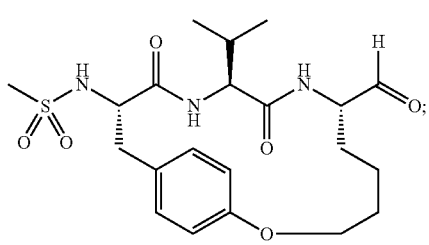
56
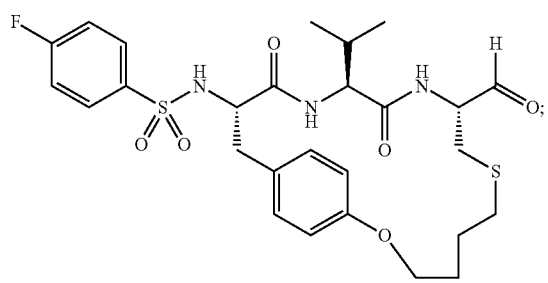
58
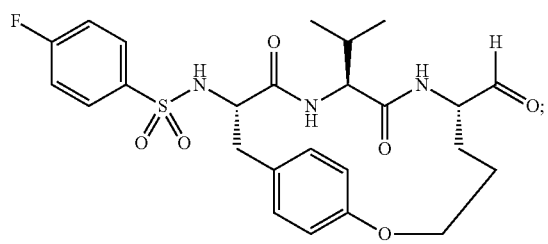
69
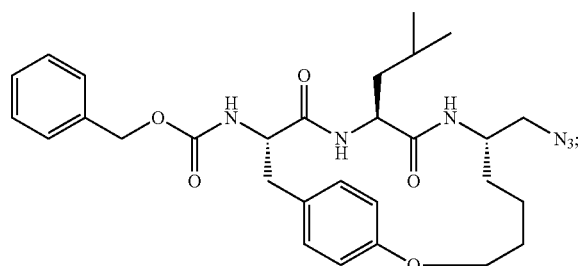
79
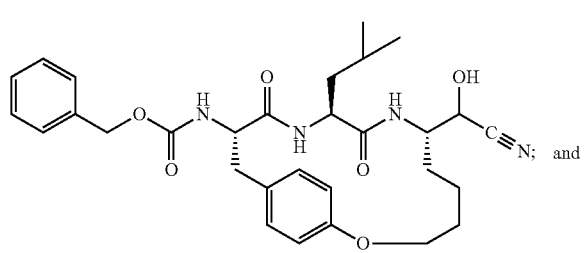
80
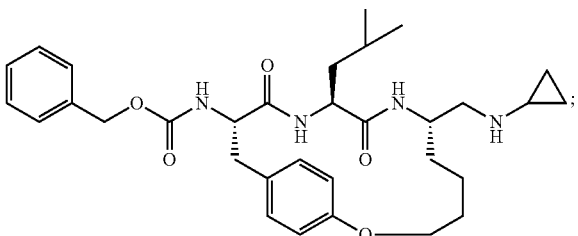
81
and the pharmaceutically acceptable salts, solvates, hydrates or prodrug derivatives thereof.
A further particularly preferred group of compounds of Formula I consists of:
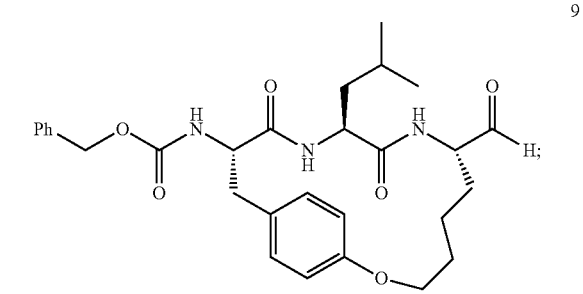 [SMILES: CC(C)C[C@@H]1NC(=O)[C@@H](NC(=O)OCc2ccccc2)Cc2ccc(cc2)OCCCC[C@@H](C=O)NC1=O]
9
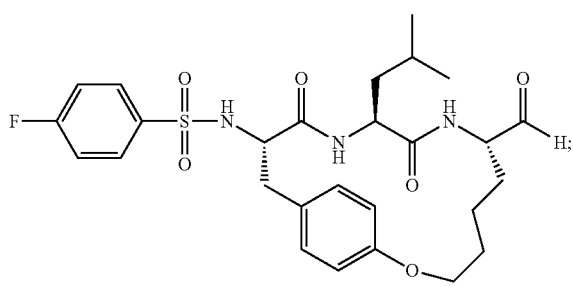
17
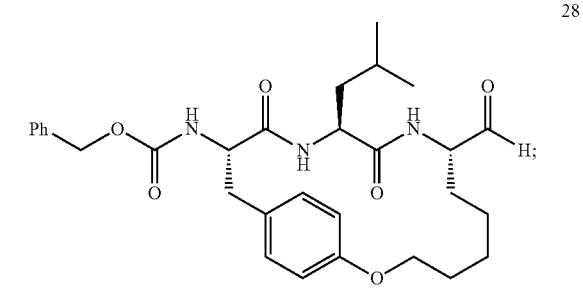
28
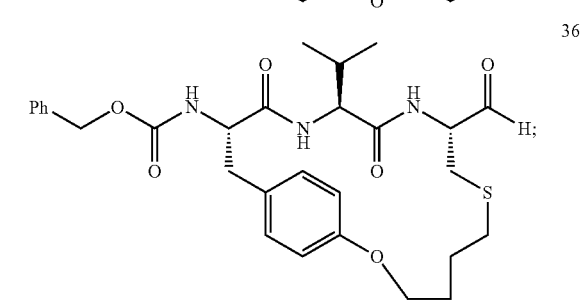
36

-continued

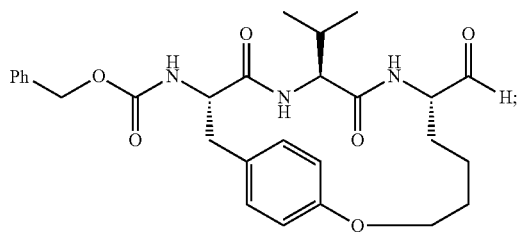
50

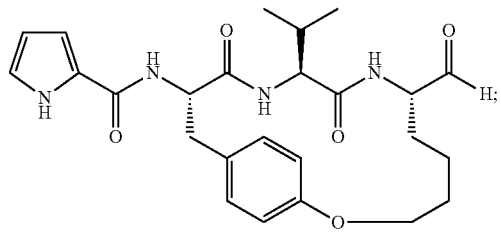
52

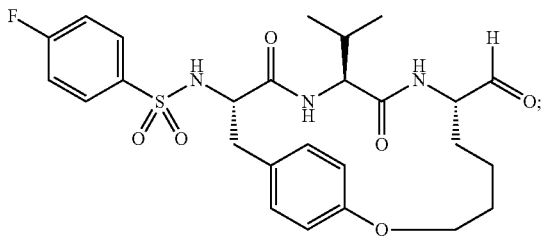
54

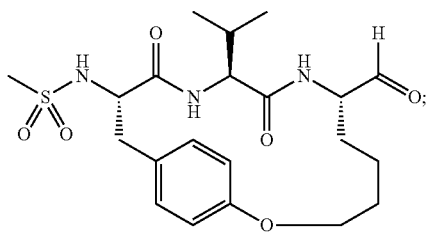
56

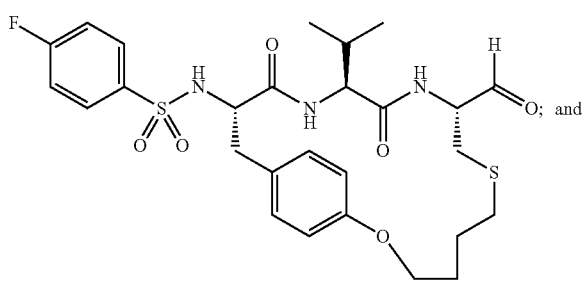
58

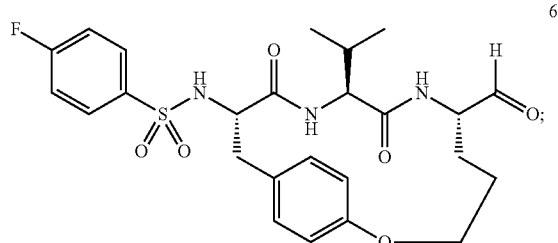
69 and the pharmaceutically acceptable salts, solvates, hydrates or prodrug derivatives thereof.

Another particularly preferred group of compounds of Formula I consists of:

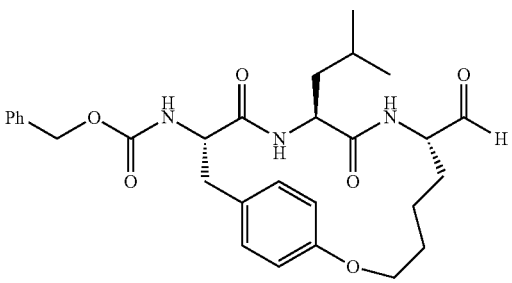
9 and the pharmaceutically acceptable salts, solvates, hydrates or prodrug derivatives thereof.

The present invention also provides a compound of Formula II or a salt, solvate or hydrate thereof:

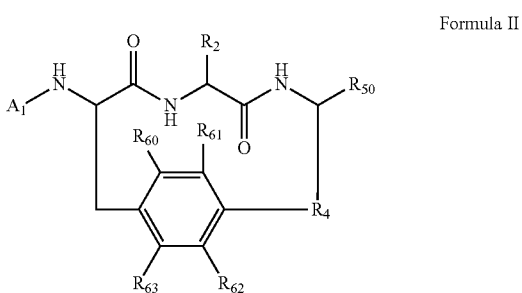

Formula II wherein;
$R_{50}$ is —C(=O)O—$R_{40}$;
$R_{40}$ is alkyl, benzyl, allyl, dialkylphenyl or silyl;
$A_1$ is hydrogen, an amino protecting group or A; and
A, $R_2$, $R_4$, $R_{60}$, $R_{61}$, $R_{62}$ and $R_{63}$ are as defined for Formula I.

The compounds of Formula II are useful as intermediates in the preparation of compounds of Formula I.

In a preferred embodiment, $R_{40}$ is $C_1$-$C_6$-alkyl. More preferably, $R_{40}$ is methyl or tert-butyl. More preferably, $R_{40}$ is methyl.

In a preferred embodiment, $A_1$ is tert-butoxycarbonyl, benzyloxycarbonyl or —S(=O)$_2$-(4-fluorophenyl).

The present invention also provides a compound of Formula III or a salt, solvate or hydrate thereof:

Formula III wherein;
$A_1$ is hydrogen or an amino protecting group; and
$R_2$, $R_3$, $R_4$, $R_{60}$, $R_{61}$, $R_{62}$ and $R_{63}$ are as defined for Formula I.

The compounds of Formula III are useful as intermediates in the preparation of compounds of Formula I.

In a preferred embodiment, $A_1$ is tert-butoxycarbonyl or benzyloxycarbonyl.

The present invention also provides a compound of Formula IV or a salt, solvate or hydrate thereof:

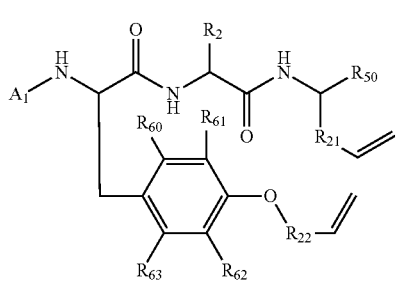

Formula IV wherein;

$R_{21}$ is optionally substituted straight chain $(C_m)$-alkyl; and
$R_{22}$ is optionally substituted straight chain $(C_n)$-alkyl;
wherein m=0-4 and n=0-4; provided that the sum m+n=1-4; and wherein any one methylene group of $R_{21}$ and $R_{22}$, except that adjacent to the oxygen atom to which $R_{22}$ is attached may be replaced by an oxygen, nitrogen or sulfur heteroatom or a —S(=O)— or —S(=O)$_2$— group; and wherein any two carbon atoms, or a carbon atom and a nitrogen atom, if present, of $R_{21}$ may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl, or any two carbon atoms, or a carbon atom and a nitrogen atom, if present, of $R_{22}$ may be linked to one another through a chain of 1 to 4 atoms to form a fused ring selected from optionally substituted cycloalkyl, optionally substituted cycloalkenyl, optionally substituted heterocyclyl, optionally substituted aryl and optionally substituted heteroaryl;
$A_1$ is hydrogen, an amino protecting group or A; and
A, $R_2$, $R_{60}$, $R_{61}$, $R_{62}$ and $R_{63}$ are as defined for Formula I and $R_{50}$ is as defined for Formula II.

In a preferred embodiment, $A_1$ is tert-butoxycarbonyl, benzyloxycarbonyl or —S(=O)$_2$-(4-fluorophenyl).

The compounds of Formula IV are useful as intermediates in the preparation of compounds of Formula I, Formula II and Formula III.

The present invention also provides a compound of Formula V or a salt, solvate or hydrate thereof:

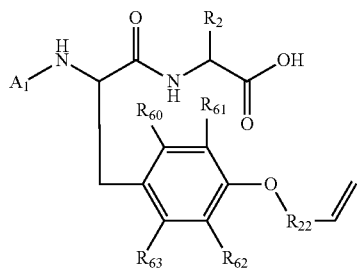

Formula V wherein $R_2$, $R_{60}$, $R_{61}$, $R_{62}$ and $R_{63}$ are as defined for Formula I and $A_1$ and $R_{22}$ are as defined for Formula IV.

The compounds of Formula V are useful as intermediates in the preparation of compounds of Formula I, Formula II, Formula III and Formula IV.

The present invention also provides a compound of Formula VI or a salt, solvate or hydrate thereof:

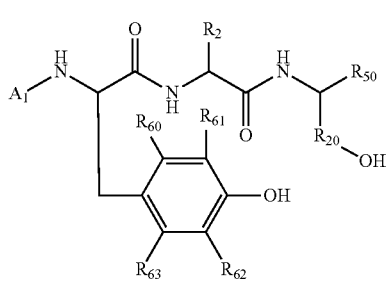

Formula VI wherein $A_1$ is hydrogen, an amino protecting group or A; and
A, $R_2$, $R_{20}$, $R_{60}$, $R_{61}$, $R_{62}$ and $R_{63}$ are as defined for Formula I and $R_{50}$ is as defined for Formula II.

In a preferred embodiment, $A_1$ is benzyloxycarbonyl.

The compounds of Formula VI are useful as intermediates in the preparation of compounds of Formula I, Formula II and Formula III.

The group $R_{50}$ in the compounds of Formulae II, IV and VI is a carboxyl protecting group. The present invention also contemplates compounds of Formulae II', IV' and VI' in which the group $R_{50}$ is an alternative carboxyl protecting group such as; an oxazole (described in, for example, H. L. Wehrmeister, J. Org. Chem. 1961, 26, 3821); a dioxanone (described in, for example, K. Ishihara et al., Synlett. 1996, 839); an ortho ester (described in, for example, E. J. Corey and N. Raju, Tetrahedron Lett. 1983, 24, 5571); or a Braun ortho ester (described in, for example, D. Waldmuller, M. Braun and A. Steigel, Synlett. 1991, 160); and wherein all of the other variables are as defined for the corresponding compounds of Formulae II, IV and VI.

The present invention also provides the compound (S)-2-[(S)-3-(4-allyloxy-phenyl)-2-(4-fluoro-benzenesulfonylamino)-propionylamino]-4-methyl-pentanoic acid methyl ester:

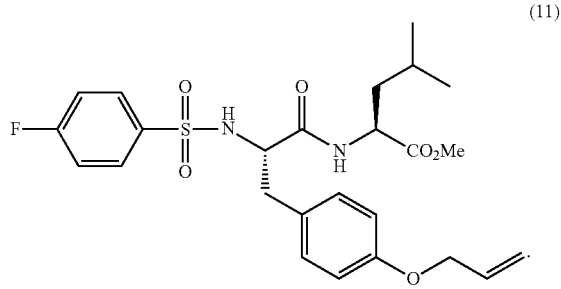 [SMILES: C=CCOc1ccc(C[C@H](NS(=O)(=O)c2ccc(F)cc2)C(=O)N[C@@H](CC(C)C)C(=O)OC)cc1]

(11)

The present invention also provides the compound (S)-3-(4-but-3-enyloxy-phenyl)-2-tert-butoxycarbonylamino-propionic acid methyl ester:

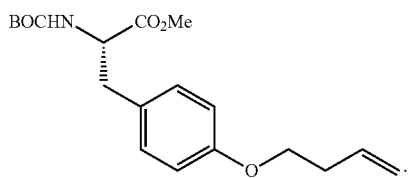
(18)

The present invention also provides the compound (S)-3-(4-but-3-enyloxy-phenyl)-2-tert-butoxycarbonylamino-propionic acid:

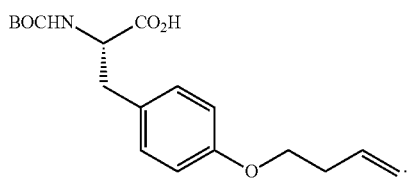
(19)

The present invention also provides the compound (S)-2-[(S)-3-(4-but-3-enyloxy-phenyl)-2-tert-butoxycarbonylamino-propionylamino]-4-ethyl-pentanoic acid methyl ester:

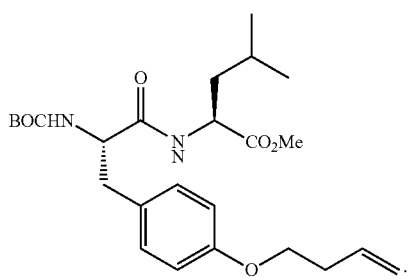
(20)

The present invention also provides the compound (S)-6-hydroxy-2-{(S)-2-[(S)-3-(4-hydroxy-phenyl)-2-methyl-propionylamino]-4-methyl-pentanoylamino}-hexanoic acid methyl ester:

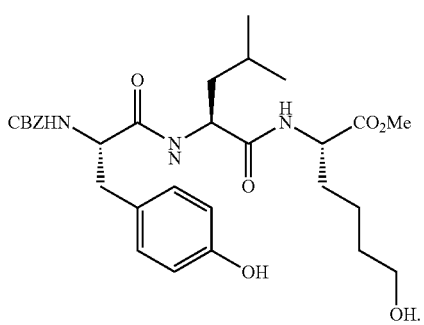
(83)

The compounds of the invention may have asymmetric carbon atoms. Therefore, stereoisomers (both enantiomers and diastereomers) of such compounds can exist. The present invention contemplates the pure stereoisomers and any mixture of the isomers. For example, a pure enantiomer of a compound of the invention can be isolated from a mixture of enantiomers of the compound using conventional optical resolution techniques. Enol forms and tautomers are also contemplated.

Compounds of the invention, including compounds of Formula I, may be prepared by, for example, the process shown in Scheme 1. The substituents $R_{60}$, $R_{61}$, $R_{62}$ and $R_{63}$ are omitted in the interests of clarity.

Scheme 1

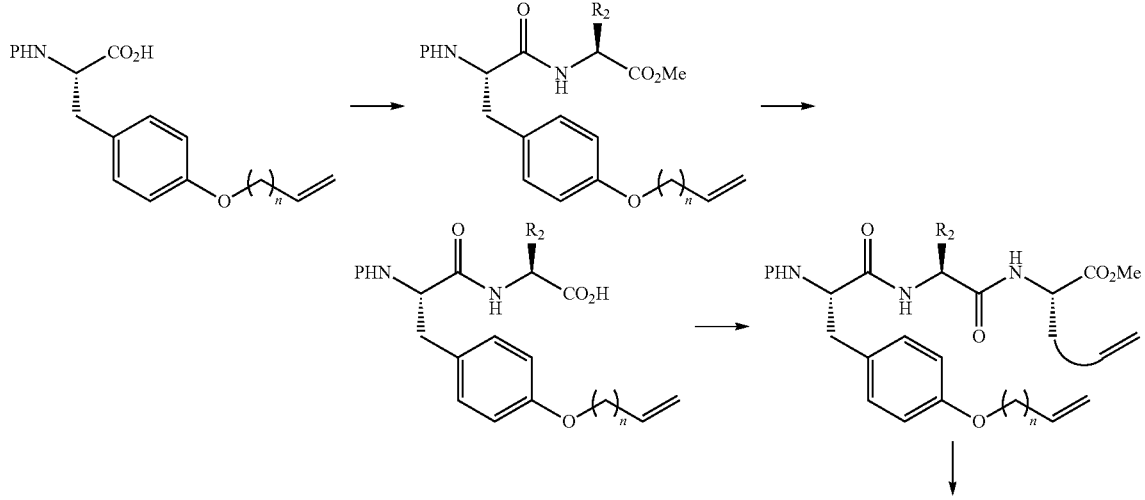

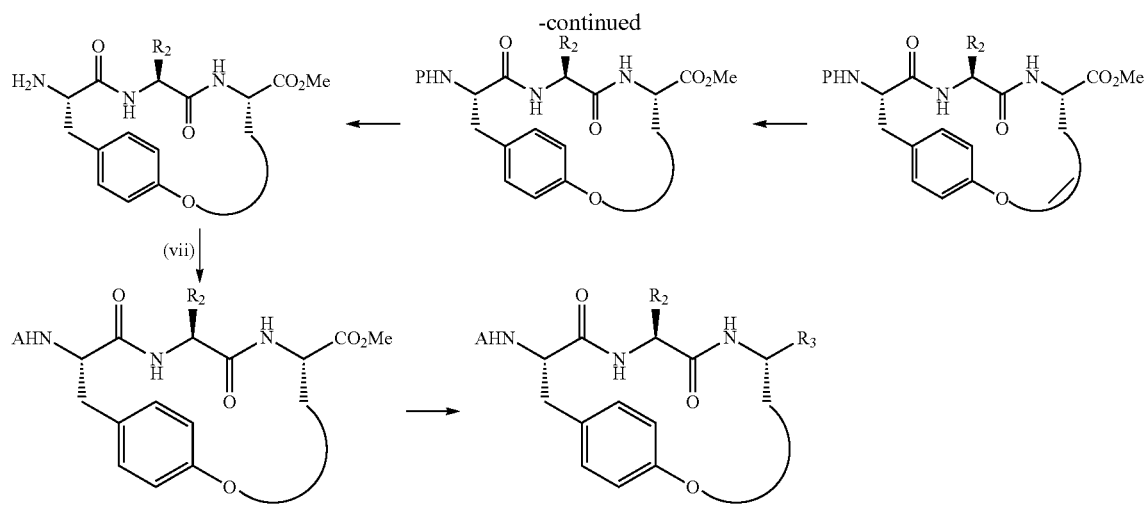

As shown in Scheme 1, an orthogonally protected tri-peptide diene may be synthesised using the required C-terminus protected or side chain allylated amino acids. P represents an amino protecting group. Standard HATU mediated peptide coupling and base hydrolysis procedures may be employed. The unsaturated macrocycle may then be formed from the diene by, for example, thermal or microwave assisted ring closing metathesis. The unsaturated macrocycle can then be hydrogenated and the N-terminus protecting group may be cleaved to yield the saturated macrocyclic amine. The address region moiety (A) may be introduced using either standard sulfonamide or amide bond formation conditions. The methyl ester is then converted into the desired functional group ($R_3$).

Alternatively, compounds of the invention, including compounds of Formula I, may be prepared by, for example, the process shown in Scheme 2. The substituents $R_{60}$, $R_{61}$, $R_{62}$ and $R_{63}$ are omitted in the interests of clarity.

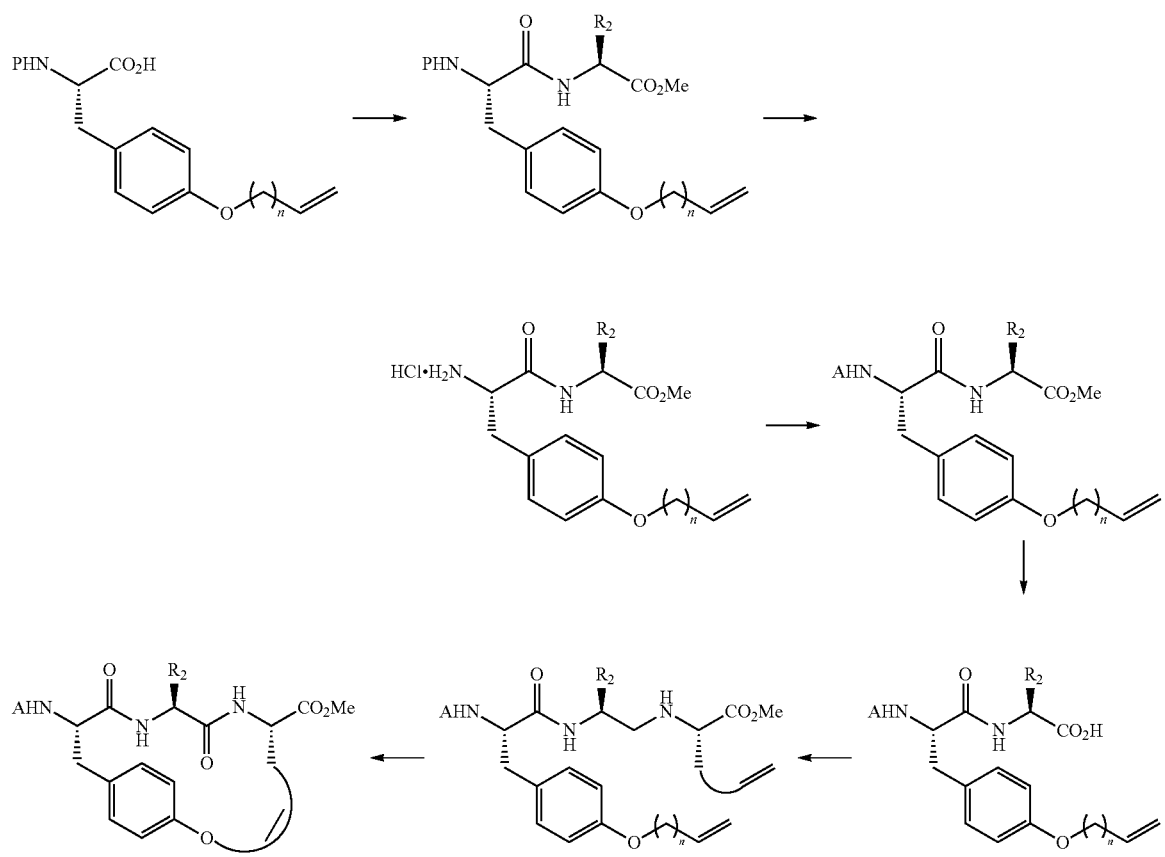

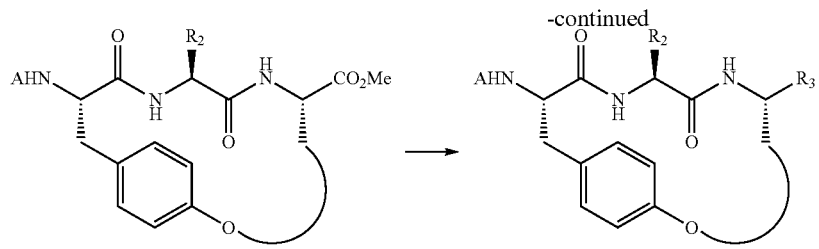

As shown in Scheme 2, the required tri-peptide diene with the desired address moiety (A) may be synthesised using the required C-terminus protected or side chain allylated amino acids. P represents an amino protecting group. Standard HATU mediated peptide coupling and base hydrolysis procedures may be employed. The A group may be introduced using either standard peptide coupling or sulfonyl chloride coupling procedures. The unsaturated macrocycle may be formed from the diene by, for example, thermal or microwave assisted ring closing metathesis.

Hydrogenation and then conversion of the C-terminus protecting group into the desired functional group ($R_3$) may be used to yield the compound of Formula I.

Alternatives to microwave assisted ring closing metathesis are known to those skilled in the art. These include, for example: nucleophilic substitution reactions, such as the Mitsunobu reaction (described in, for example, A. Arasappan et al., *J. Org. Chem.* 2002, 67, 3923 and A. Arasappan et al., *Bioorganic & Medicinal Chemistry Letters* 2006, 16, 3960); and palladium cross coupling reactions (described in, for example, R. Bates, *Organic Synthesis using Transition Metals*, Sheffield Academic Press Ltd., Sheffield, 2000).

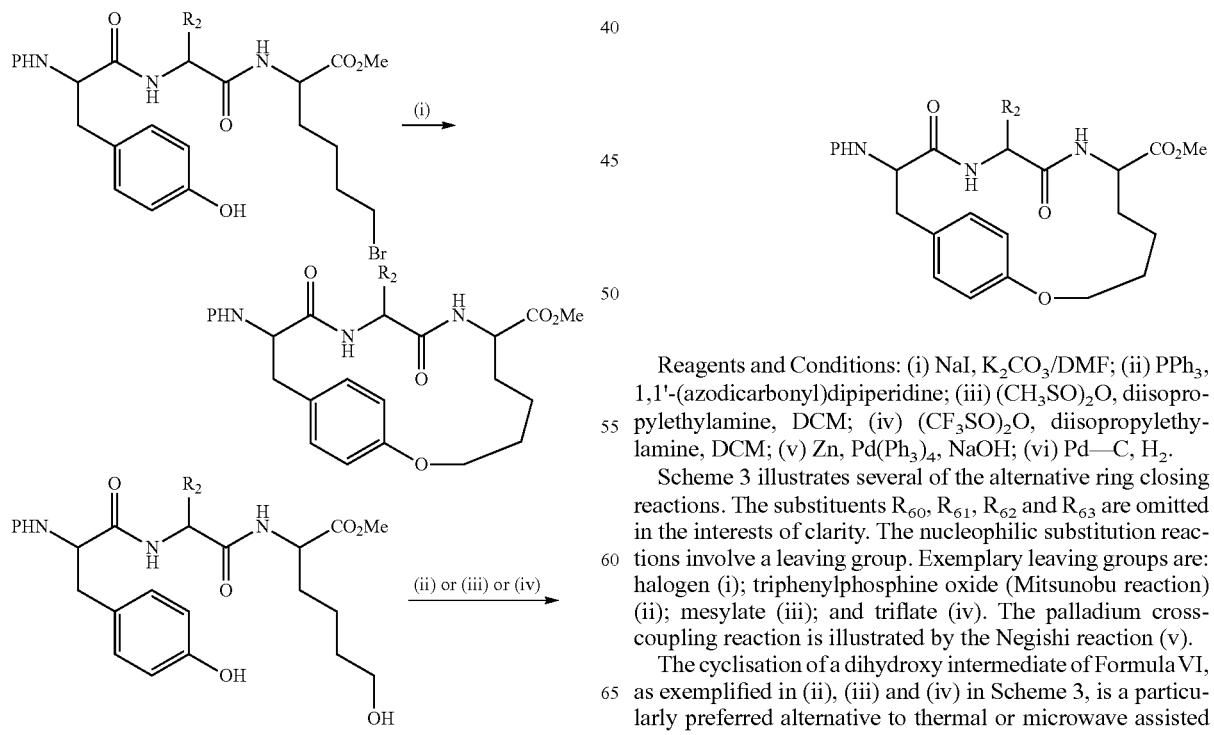

Reagents and Conditions: (i) NaI, $K_2CO_3$/DMF; (ii) $PPh_3$, 1,1'-(azodicarbonyl)dipiperidine; (iii) $(CH_3SO)_2O$, diisopropylethylamine, DCM; (iv) $(CF_3SO)_2O$, diisopropylethylamine, DCM; (v) Zn, $Pd(Ph_3)_4$, NaOH; (vi) Pd—C, $H_2$.

Scheme 3 illustrates several of the alternative ring closing reactions. The substituents $R_{60}$, $R_{61}$, $R_{62}$ and $R_{63}$ are omitted in the interests of clarity. The nucleophilic substitution reactions involve a leaving group. Exemplary leaving groups are: halogen (i); triphenylphosphine oxide (Mitsunobu reaction) (ii); mesylate (iii); and triflate (iv). The palladium cross-coupling reaction is illustrated by the Negishi reaction (v).

The cyclisation of a dihydroxy intermediate of Formula VI, as exemplified in (ii), (iii) and (iv) in Scheme 3, is a particularly preferred alternative to thermal or microwave assisted ring closing metathesis.

The present invention also provides a process for preparing a compound of Formula I:

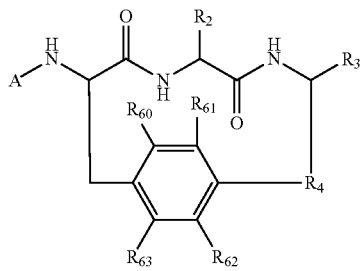

Formula I the process comprising the steps of:
(a) cyclising a compound of Formula VI:

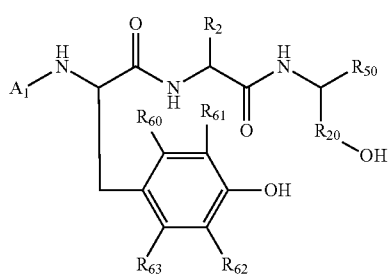

Formula VI to provide a compound of Formula II:

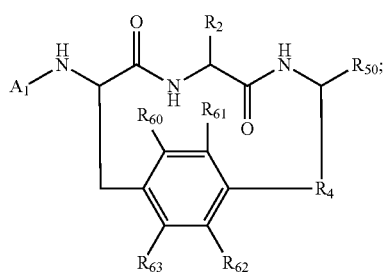

Formula II and
(b) converting the compound of Formula II into the compound of Formula I.

In one embodiment, the process further comprises the steps of:
(a) providing a compound of Formula VII:

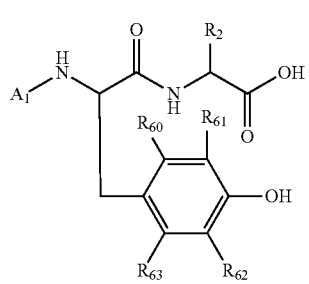

Formula VII or an activated acid derivative thereof, wherein $A_1$ is hydrogen, an amino protecting group or A; and
A, $R_2$, $R_{60}$, $R_{61}$, $R_{62}$ and $R_{63}$ are as defined for Formula I; and
(b) coupling the compound of Formula VII with a compound of Formula VIII:

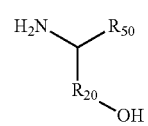

Formula VIII or an activated amino derivative thereof, wherein $R_{20}$ is as defined for Formula I and $R_{50}$ is as defined for Formula II, to provide the compound of Formula VI.

The present invention also provides a process for preparing a compound of Formula I:

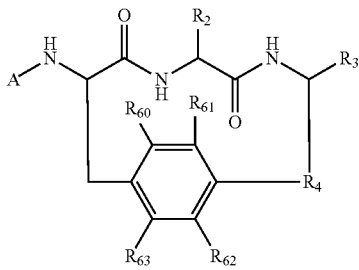

Formula I the process comprising the steps of:
(a) cyclising a compound of Formula IV:

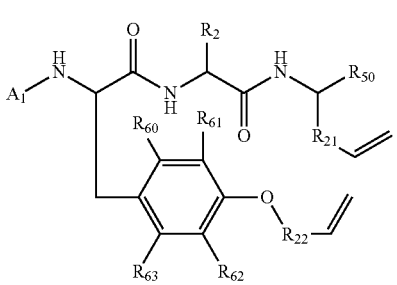

Formula IV to provide a compound of Formula II:

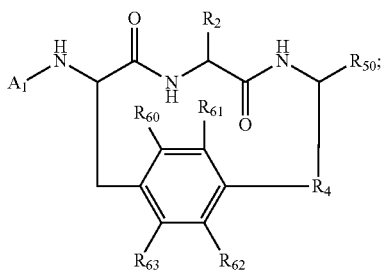

Formula II and
(b) converting the compound of Formula II into the compound of Formula I.

In one embodiment, the process further comprises the steps of:
(a) providing a compound of Formula V:

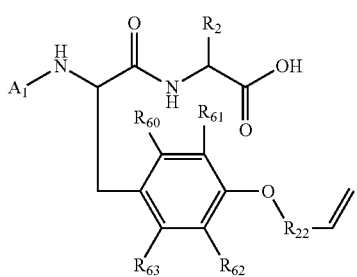

Formula V or an activated acid derivative thereof; and
(b) coupling the compound of Formula V with a compound of Formula IX:

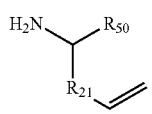

Formula IX or an activated amino derivative thereof, wherein $R_{21}$ is as defined for Formula IV and $R_{50}$ is as defined for Formula II, to provide the compound of Formula IV.

The peptide coupling reactions are generally conducted in dimethylformamide (DMF) in the presence of a coupling agent, such as O-(7-azabenzotriazol-1-yl)-N,N,N',N'-tetramethyluronium hexafluorophosphate (HATU), and a suitable base, such as diisopropyl ethyl amine (DIPEA). A catalytic auxiliary nucleophile, such as 1-hydroxybenzotriazole (HOBt), may also be used. Alternatively, the acid chloride, acid fluoride or mixed acid anhydride of the carboxylic acid may be utilised. Other coupling reagents may also be utilised including, but not limited to: N,N'-dicyclohexylcarbodiimide (DCC); N-(3-dimethylaminopropyl)-N'-ethylcarbodiimide (EDC); (7-azabenzotriazol-1-yloxy)tripyrrolidinophosphonium hexafluorophosphate (PyAoP); bromotripyrrolidinophosphonium hexafluorophosphate (PyBroP); and O-(benzotriazol-1-yl)-N,N,N',N'-tetramethyluronium tetrafluoroborate (TBTU).

Compounds of the invention in which $R_{20}$ includes a carbon-carbon double bond may be transformed into other compounds of the invention using methods known to those skilled in the art. For example, the double bond may be halogenated (see, for example, P. B. D. de la Mare, *Electrophilic Halogenation*, Cambridge University Press, Cambridge, 1976), epoxidised (see, for example, R. C. Larock, *Comprehensive organic transformations*, VCH, New York, 1989, p 456 and the references cited therein) or dihydroxylated (see, for example, R. C. Larock, *Comprehensive organic transformations*, VCH, New York, 1989, p 494 and the references cited therein). The double bond may also be subjected to a Diels-Alder cycloaddition reaction to give compounds wherein $R_{20}$ includes a cyclic moiety (see, for example, A. Wasserman, *Diels-Alder Reactions*, Elsevier, New York, 1965).

Compounds of the invention wherein $R_3$ is —CH(OH)$R_{10}$ and $R_{10}$ is alkoxy or thioalkoxy may be prepared by reacting the corresponding aldehyde with the appropriate alcohol or thiol.

Compounds of the invention may be prepared according to the general methodology described above and in the Examples. A person skilled in the art will be able, without undue experimentation and with regard to that skill and this disclosure, to select appropriate reagents and conditions to modify these methodologies to produce compounds of the invention.

Those persons skilled in the art will appreciate that other synthetic routes may be used to synthesize the compounds of the invention. In addition, those persons skilled in the art will appreciate that, in the course of preparing the compounds of the invention, the functional groups of intermediate compounds may need to be protected by protecting groups. Functional groups which it may be desirable to protect include, but are not limited to: hydroxyl; amino; and carboxylic acid groups. Protecting groups may be added and removed in accordance with techniques that are well known to those persons skilled in the art. The use of protecting groups is described in, for example, J. W. F. McOmie (ed.), *Protective Groups in Organic Chemistry*, Plenum Press, London, 1973 and T. W. Greene and P. G. M. Wutz, *Protective Groups in Organic Synthesis*, $2^{nd}$ edition, Wiley, New York, 1991.

As described in the Examples, compounds of Formula I have been determined to have enzyme inhibitory activity in tests which are predictive of such activity in mammals, including humans. Such properties render the compounds of the invention suitable for use, alone or together with other active agents, in a number of therapeutic applications, including those that involve cysteine protease inhibition.

Molecular modelling of compounds of Formula I has demonstrated that they are able to form the beta-strand typical peptide secondary structural motif. Without wishing to be bound by theory, it is believed that a beta-strand structure of a compound is required for molecular recognition by, and inhibition of, cysteine proteases.

In particular, compounds of Formula I have been found to inhibit calpains. There is experimental evidence to demonstrate the involvement of excessive calpain activity in a variety of pathologies (K. K. W. Wang, and P-W. Yuen, *Trends Pharmacol. Sci.* 1994, 15, 412; D. Brömme, *Drug News Perspect.* 1999, 12, 73). Such pathologies include: inflammatory and immunological diseases, for example rheumatoid arthritis, pancreatitis, multiple sclerosis and inflammations of the gastro-intestinal system including ulcerative or non-ulcerative colitis and Crohn's disease; cardiovascular and cerebrovascular diseases, for example arterial hypertension, septic shock, cardiac or cerebral infarctions of ischemic or hemorrhagic origin, ischemia, and disorders linked to platelet aggregation; disorders of the central or peripheral nervous system, for example neurodegenerative diseases including cerebral or spinal cord trauma, sub-arachnoid haemorrhage, epilepsy, ageing, senile dementia including Alzheimer's disease and Huntington's chorea, Parkinson's disease and peripheral neuropathies; osteoporosis; muscular dystrophies; cachexia; proliferative diseases, for example atherosclerosis or recurrence of stenosis; loss of hearing; ocular disorders, for example optic neuropathies, including ischemic optic neuropathies and diabetic neuropathy, glaucoma, macular degeneration and retinal damage, including detachment, tears or holes, presbyopia and cataracts; organ transplant; auto-immune and viral diseases, for example lupus, AIDS, parasitic and viral infections, diabetes and its complications and multiple sclerosis; and cancer.

Given the role of calpains in these pathologies, the compounds of Formula I can produce beneficial or favourable effects in their treatment.

Accordingly, in another aspect, the invention provides a compound of Formula I for use as a medicament.

More particularly, the invention provides a compound of Formula I for use as a cysteine protease inhibitor. In a preferred embodiment, the cysteine protease is a calpain.

In another aspect, the present invention provides a method for inhibiting a cysteine protease in a mammal comprising the step of administering a compound of Formula I to the mammal.

The term "mammal" as used herein refers to a human or non-human mammal. Examples of non-human mammals include livestock animals such as sheep, cows, pigs, goats, rabbits and deer; and companion animals such as cats, dogs, rodents and horses.

In another aspect, the present invention provides a method for the treatment or prophylaxis of a disease or disorder resulting from excessive cysteine protease activity in a mammal comprising the step of administering a compound of Formula I to the mammal.

The invention further provides an in vitro method for inhibiting a cysteine protease comprising contacting the cysteine protease with a compound of the invention.

The invention also provides a method of inhibiting a cysteine protease in a cell comprising contacting the cell with an effective amount of a compound of Formula I.

In another aspect, the present invention provides a use of a compound of Formula I for the manufacture of a medicament for reducing the activity of a cysteine protease.

In another aspect, the present invention provides a use of a compound of Formula I for the manufacture of a medicament for the treatment or prophylaxis of a disease or disorder resulting from excessive cysteine protease activity.

In preferred embodiments of the method and use aspects of the present invention, the cysteine protease is a calpain.

In particular embodiments, the disease or disorder results from excessive calpain activity and is selected from the group consisting of: disorders of the central or peripheral nervous system; muscular dystrophies; cachexia; loss of hearing; and ocular disorders.

In a particularly preferred embodiment, the disease or disorder resulting from excessive calpain activity is cataracts.

Therefore, in another aspect, the present invention provides a method for the treatment or prophylaxis of cataracts in a mammal comprising the step of administering a compound of Formula I to the mammal.

The present invention also provides a use of a compound of Formula I for the manufacture of a medicament for the treatment or prophylaxis of cataracts.

In another aspect, the invention provides a composition comprising a compound of Formula I. In a preferred embodiment, the composition is a pharmaceutical composition and further comprises a pharmaceutically acceptable carrier, diluent or excipient.

Pharmaceutically acceptable carriers, diluents and excipients are non-toxic to recipients at the dosages and concentrations employed. Each carrier, diluent and excipient must also be "acceptable" in the sense of being compatible with the other ingredients of the formulation.

The compound of Formula I, or the composition comprising same, may be administered to a mammal by different routes. The most suitable route may depend upon, for example, the condition and disease of the mammal. Preferred administration routes are oral, parenteral and topical, including intraocular.

The compositions of the present invention may be formulated for administration in unit dosage forms, such as tablets, capsules, pills, powders, granules, suppositories, sterile parenteral solutions or suspensions, sterile non-parenteral solutions or suspensions, oral solutions or suspensions, topical solutions or suspensions, and intraocular solutions or suspensions and the like, that comprise a compound of the invention as an active ingredient.

Solid or fluid unit dosage forms can be prepared for oral administration.

Powders may be prepared by comminuting the active ingredient to a suitably fine size and mixing with a similarly comminuted diluent or excipient. Suitable diluents and excipients are known to those persons skilled in the art.

Capsules may be produced by preparing a powder mixture as described above and filling into formed gelatine sheaths. Soft gelatine capsules may be prepared by encapsulating a slurry of the active ingredient with an acceptable vegetable oil, light liquid petrolatum or other inert oil or triglyceride.

Tablets may be made by preparing a powder mixture, granulating or slugging, adding a lubricant and pressing into tablets. The powder mixture is prepared by mixing the active ingredient, suitably comminuted, with a diluent or base. Suitable diluents and bases are known to those persons skilled in the art. The powder mixture can be granulated by wetting with a binder and forcing through a screen. As an alternative to granulating, the powder mixture can be slugged, i.e. run through a tablet machine and the resulting imperfectly formed tablets broken into pieces (slugs). The slugs can be lubricated to prevent sticking to the tablet-forming dies. The lubricated mixture can then be compressed into tablets.

In one embodiment, the tablet is provided with a protective coating.

Fluid unit dosage forms for oral administration, such as syrups, elixirs and suspensions, wherein a specific volume of composition contains a predetermined amount of active ingredient for administration, can be prepared. Water-soluble active ingredients can be dissolved in an aqueous vehicle together with other ingredients to form a syrup. An elixir is prepared by using a hydro-alcoholic vehicle. Suspensions can be prepared from insoluble forms in a suitable vehicle with the aid of a suspending agent.

Fluid unit dosage forms are prepared for parenteral administration utilising an active ingredient and a sterile vehicle. The active ingredient can be either suspended or dissolved in the vehicle, depending on the form and concentration used. In preparing solutions, the water-soluble active ingredient can be dissolved in a suitable solvent for injection and filter sterilised before filling into a suitable vial or ampoule and sealing. Adjuvants can also be dissolved in the vehicle. Parenteral suspensions are prepared in substantially the same manner.

In addition to oral and parenteral administration, the rectal and vaginal routes may be utilised. An active ingredient can be administered by means of a suppository. A vehicle which has a melting point at about body temperature or one that is readily soluble can be utilised.

Fluid unit dosage forms for intranasal instillation are prepared utilising an active ingredient and a suitable pharmaceutical vehicle. Alternatively, a dry powder can be utilised for insufflation.

The active ingredients, together with a gaseous or liquefied propellant and suitable adjuvants as may be necessary or desirable, can be packaged into a pressurized aerosol container for use as an aerosol.

Suitable dosage forms for intraocular administration include, but are not limited to: eye drops; and ophthalmic emulsions and ointments. In addition to a compound of the invention, the topical dosage forms may comprise a variety of other components, for example: solvents; stabilisers; emulsifiers; suspending agents; surfactants; preservatives; buffers; isotonising agents; pH control agents; and ointment bases.

Examples of the techniques and protocols mentioned above can be found in A. R. Gennaro (ed.), *Remington's Pharmaceutical Sciences*, 18$^{th}$ edition, Mack Publishing Company, Easton 1990.

The compounds of Formula I and compositions of the invention may be used in combination therapies with one or more other active agents. The one or more other active agents may form part of the same composition, or be formulated as one or more separate compositions for administration at the same time or a different time.

Administration of the compound of Formula I or composition of the invention is preferably in a therapeutically effective amount, this being an amount sufficient to show the desired benefit to the mammal, including preventing or alleviating the symptoms of any disease or disorder being prevented or treated. The particular dosage of active ingredient to be administered will depend upon the specific disease to be treated, and various characteristics of the mammal, including age, gender, health and weight. In addition, therapeutic factors such as the site of delivery, the method of administration, any concurrent treatment, the frequency of treatment and therapeutic ratio, may also be relevant. Determining the appropriate dosage is within the ability of those persons skilled in the art.

It is expected that a useful unit dosage will comprise between about 0.1 to about 1000 mg, preferably 1 to 200 mg, of a compound of Formula I.

When the compound of Formula I is formulated for intraocular administration, for example as an eye drop solution, it is expected that a useful concentration of a compound of the invention will comprise about 0.001 to about 2.0% (w/v), preferably 0.01 to 1.0% (w/v). Approximately 20 to 50 µL of such a solution may be instilled into the eye at regular intervals throughout the day.

In a preferred embodiment, the compound of Formula I is formulated into an ointment for intraocular administration. In a particularly preferred embodiment, the ointment has the following composition (w/w):
1% compound of Formula I
25% cetyl stearyl alcohol
35% wool fat
39% paraffinum subl.

In a preferred embodiment, the compound of Formula I is formulated into an emulsion for intraocular administration. In a particularly preferred embodiment, the emulsion has the following composition (w/w):
0.7% compound of Formula I
20% cetyl stearyl alcohol
25% wool fat
25% paraffinum subl.
1% sodium lauryl sulfate
0.1% sodium benzoate
28.3% water The following non-limiting examples are provided to illustrate the present invention and in no way limit the scope thereof.

EXAMPLES

Compounds within the scope of the invention were prepared by the following synthetic procedures.
Abbreviations
1,1,2-TCE 1,1,2-trichloroethane
BOC tert-butoxycarbonyl
BODIPY 4,4-difluoro-5,7-dimethyl-4-bora-3a,4-diaza-s-indacene-3-propionic acid
CBZ benzyloxycarbonyl
1,2-DCE 1,2-dichloroethane
DCM dichloromethane
DIBAL-H diisobutylaluminium hydride
DIPEA diisopropyl ethyl amine
DMF dimethylformamide
DMSO dimethylsulfoxide
EDC N-(3-dimethylaminopropyl)-N'-ethylcarbodiimide
EMEM Eagle's minimum essential medium
ES electrospray mass spectrometry
Et$_2$O diethyl ether
EtOAc ethyl acetate
FTIR Fourier transform infrared spectroscopy
GSGC Grubbs second generation catalyst—benzylidene[1,3-bis(2,4,6-trimethylphenyl)-2-imidazolidinyidene]dichloro(tricyclohexyl-phosphine)ruthenium
h hour(s)
HATU O-(7-azabenzotriazol-1-yl)-N,N,N',N'-tetramethyluronium hexafluorophosphate
HOBt hydroxybenzotriazole
HRMS high resolution mass spectrometry
LCMS liquid chromatography mass spectrometry
MeOH methanol
min(s) minute(s)
m.p. melting point
NMR nuclear magnetic resonance spectroscopy
Ph phenyl
rt room temperature
SO$_3$.Pyr sulfur trioxide.pyridine complex
TFA trifluoroacetic acid
THF tetrahydrofuran
Synthesis Scheme 4
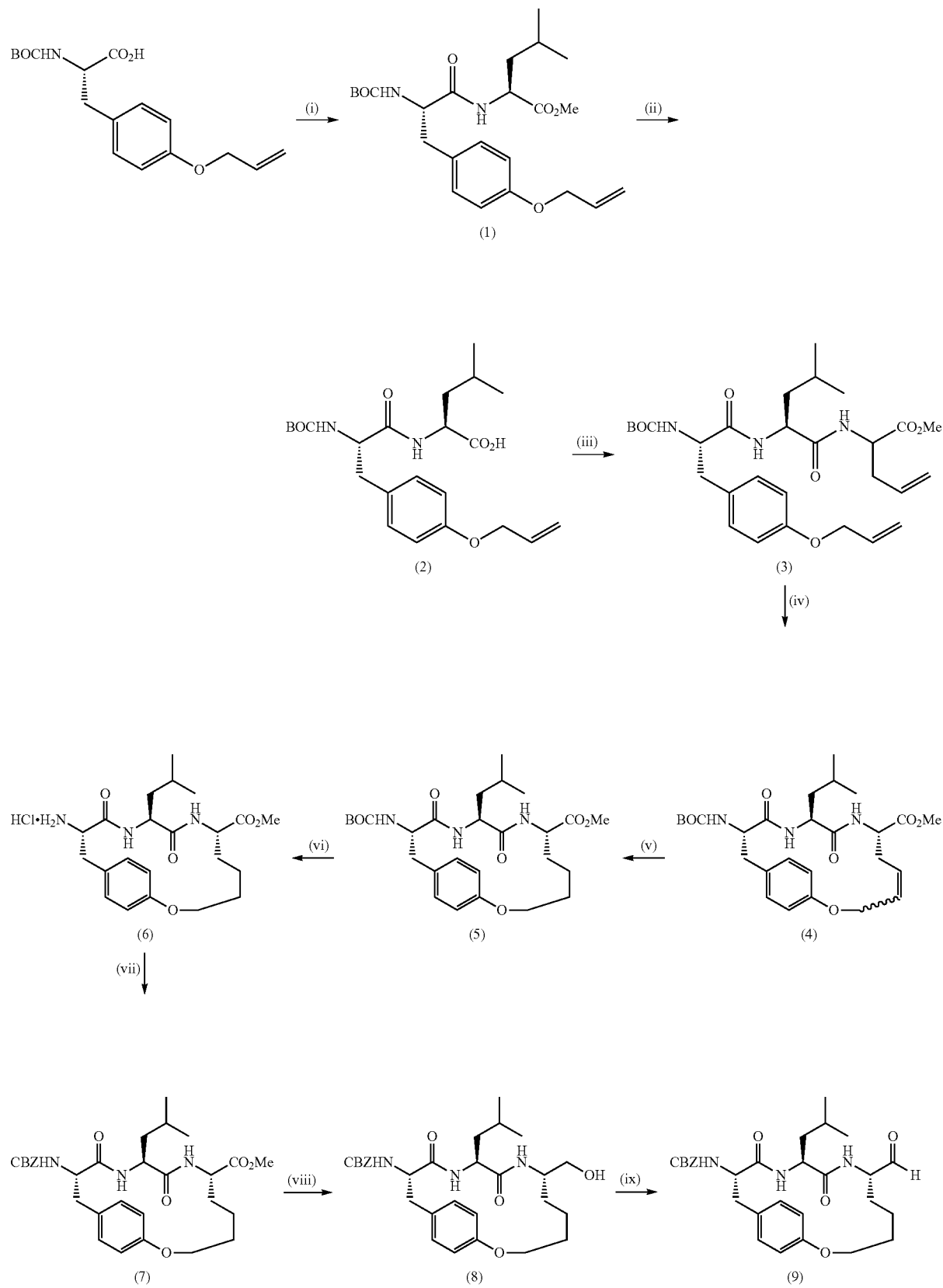

Reagents and Conditions: (i) HATU, DIPEA, Leu-OMe, DMF, (80%); (ii) NaOH, THF, $H_2O$, MeOH, (97%); (iii) HATU, DIPEA, (s)-allyl-Gly-OMe, DMF, (97%); (iv) 3×10 mol % GSGC, 10 mol % chloro-dicyclohexyl borane, 1,1,2-TCE, microwave, (91%); (v) $H_2$, 20 mol % Pd/C, MeOH, EtOAc, (98%); (vi) 4M HCl, 1,4-dioxane, (100%); (vii) benzyl chloroformate, DIPEA, DMF, (43%); (viii) $LiAlH_4$, THF, (83%); (ix) $SO_3$.Pyr, DIPEA, DMSO, DCM, (42%).

(S)-2-[(S)-3-(4-Allyloxy-phenyl)-2-tert-butoxycarbonylamino-propionylamino]-4-methyl-pentanoic acid methyl ester (1)

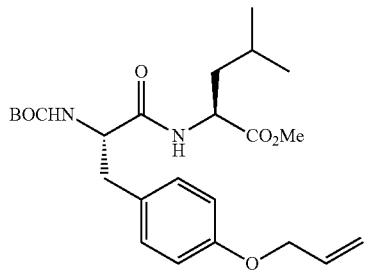

N—BOC—O-allyl-tyrosine (obtained from NeoMPS, San Diego, Calif. 92126, USA) (10.0 g, 32.5 mmol), HATU (12.4 g, 35.8 mmol) and leucine methyl ester hydrochloride (5.90 g, 65.0 mmol) were dissolved in anhydrous DMF (50 mL). DIPEA (22.7 mL, 130 mmol) was added and the reaction mixture was stirred at rt for 18 h before being partitioned between EtOAc and 1M hydrochloric acid. The organic phase was then washed sequentially with 1M hydrochloric acid and brine before being dried ($MgSO_4$), filtered and concentrated in vacuo. Purification was achieved using flash chromatography, eluting with a gradient of 1/5 EtOAc/(50/70) petroleum ether to 100% EtOAc to yield a white solid, 8.45 g, 58%. $R_f$=0.33 (1/3 EtOAc/(50/70) petroleum ether).

$^1$H-NMR (500 MHz in $CDCl_3$) 7.08 (2H, d J=8.5 Hz, Ar—H), 6.79 (2H, d J=8.5 Hz, Ar—H), 6.43 (1H, d J=7.6 Hz, NH Leu), 6.04 (1H, tdd J=5.3 Hz, J=5.3 Hz, J=10.5, J=17.1 Hz, $CH_2CHCH_2$), 5.26-5.42 (2H, m, $CH_2CHCH_2$), 5.09 (1H, d J=6.6 Hz, NH Tyr); 4.54-4.57 (1H, m, CH Leu), 4.47 (2H, d J=5.3 Hz, $CH_2CHCH_2$), 4.30-4.36 (1H, m, $CHCH_2Ph$), 3.66 (3H, s, $CO_2CH_3$), 2.88-3.02 (2H, m, $CHCH_2Ph$), 1.54-1.62 (2H, m, $CHCH_2CH(CH_3)_2$), 1.43-1.51 (1H, m, $CHCH_2CH(CH_3)_2$) 1.38 (9H, s, $(CH_3)_3$), 0.91 (3H, d J=6.6 Hz, $CHCH_2(CH_3)_2$), 0.89 (3H, d J=6.6 Hz, $CHCH_2(CH_3)_2$).

$^{13}$C-NMR (75 MHz in $CDCl_3$) 174.1, 172.8, 171.4, 157.5, 155.5, 133.2, 130.4, 130.3, 128.7, 117.4, 114.7, 68.7, 54.3, 52.1, 50.7, 41.3, 37.3, 28.2, 24.6, 22.7, 21.8.

HRMS (ES) 449.2662 (MH$^+$). $C_{24}H_{36}N_2O_6$ requires 449.2651.

(S)-2-[(S)-3-(4-Allyloxy-phenyl)-2-tert-butoxycarbonylamino-propionylamino]-4-methyl-pentanoic acid (2)

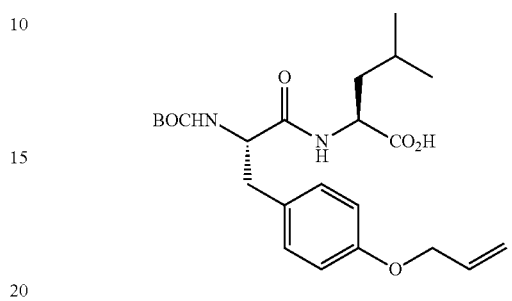

Methyl ester 1 (8.45 g, 18.8 mmol) was dissolved in THF (35 mL) and sodium hydroxide (1.13 g, 28.2 mmol) pre-dissolved in water (10 mL) was added. A further 15 mL of THF and 20 mL of methanol were added to obtain a homogenous solution. The reaction mixture was stirred at rt for 18 h before being concentrated in vacuo. The residue was partitioned between EtOAc and 1M hydrochloric acid. The aqueous phase was extracted twice more with EtOAc and the combined organic extracts were washed with brine, dried ($MgSO_4$), filtered and concentrated in vacuo to yield a white foam, 7.25 g, 89%.

$^1$H-NMR (500 MHz in $CDCl_3$) 7.10 (2H, d J=8.5 Hz, Ar—H), 6.82 (2H, d J=8.5 Hz, Ar—H), 6.58 (1H, d J=7.9 Hz, NH Leu), 6.03 (1H, tdd J=5.3 Hz, J=5.3 Hz, J=10.5 Hz, J=17.3 Hz, $CH_2CHCH_2$), 5.25-5.42 (2H, m, $CH_2CHCH_2$), 5.22 (1H, bs, NH Tyr), 4.54-4.58 (1H, m, $CHCH_2CH(CH_3)_2$), 4.48 (2H, d J=5.2 Hz, $CH_2CHCH_2$), 4.34-4.40 (1H, m, $CHCH_2Ph$), 2.96-3.02 (2H, m, $CHCH_2Ph$), 1.58-1.70 (2H, m, $CHCH_2CH(CH_3)_2$), 1.50-1.56 (1H, m, $CHCHCH_2(CH_3)_2$), 1.39 (9H, s, $C(CH_3)_3$), 0.92 (3H, d J=6.2 Hz, $CHCHCH_2(CH_3)_2$), 0.91 (3H, d J=6.2 Hz, $CHCHCH_2(CH_3)_2$).

LRMS (ES) 435.2 (MH$^+$). $C_{23}H_{34}N_2O_6$ requires 435.2.

(S)-2-{(S)-2-[(S)-3-(4-Allyloxy-phenyl)-2-tert-butoxycarbonylamino-propionylamino]-4-methyl-pentanoylamino}-pent-4-enoic acid methyl ester (3)

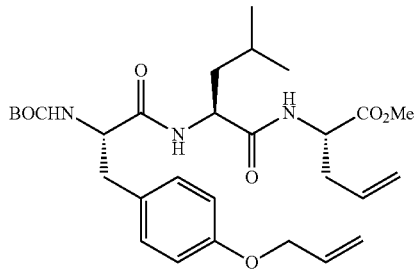

Carboxylic acid 2 (2.86 g, 6.58 mmol), HATU (2.75 g, 7.24 mmol) and (S)-allyl-glycine methyl ester hydrochloride (1.20 g, 7.24 mmol) were dissolved in DMF (30 mL). DIPEA was added (4.60 mL, 26.4 mmol) and the reaction mixture was stirred at rt for 18 h before being partitioned between EtOAc and 1M hydrochloric acid. The organic phase was washed sequentially with 1M hydrochloric acid and brine before being dried (MgSO$_4$), filtered and concentrated in vacuo. Purification was achieved using flash chromatography, eluting with a gradient of 1/3 EtOAc/(50/70) petroleum ether to 2/1 EtOAc/(50/70) petroleum ether to yield a white solid, 1.40 g, 39%. R$_f$=0.70 (1/1 EtOAc/(50/70) petroleum ether).

$^1$H-NMR (500 MHz in CDCl$_3$) 7.09 (2H, d J=8.5 Hz, Ar—H), 6.82 (2H, d J=8.5 Hz, Ar—H), 6.65 (1H, d J=7.6 Hz, NH Gly), 6.47 (1H, d J=8.1 Hz, NH Leu), 6.04 (1H, tdd J=5.3 Hz, J=5.3 Hz, J=10.5 Hz, J=17.0 Hz, OCH$_2$CHCH$_2$), 5.62-5.71 (1H, m, CHCH$_2$CHCH$_2$), 5.08-5.44 (4H, m, OCH$_2$CHCH$_2$ and CHCH$_2$CHCH$_2$), 4.99 (1H, d J=7.3 Hz, NH Tyr), 4.57-4.63 (1H, m, CHCH$_2$CH(CH$_3$)$_2$), 4.49 (2H, d J=5.2 Hz, OCH$_2$CHCH$_2$), 4.41-4.47 (1H, m, CHCH$_2$CHCH$_2$), 4.25-4.34 (1H, m, CHCH$_2$Ph), 3.73 (3H, s, CO$_2$CH$_3$); 2.96-3.05 (2H, m, CHCH$_2$Ph), 2.45-2.61 (2H, m, CHCH$_2$CHCH$_2$), 1.52-1.68 (2H, m, CHCHCH$_2$(CH$_3$)$_2$) 1.43-1.50 (1H, m, CHCHCH$_2$(CH$_3$)$_2$) 1.39 (9H, s, C(CH$_3$)$_3$), 0.90 (3H, d J=6.4 Hz, CHCHCH$_2$(CH$_3$)$_2$), 0.89 (3H, d J=6.4 Hz, CHCHCH$_2$(CH$_3$)$_2$).

$^{13}$C-NMR (75 MHz in CDCl$_3$) 171.8, 171.5, 171.3, 157.5, 155.4, 133.2, 132.2, 132.0, 130.3, 130.1, 128.5, 119.2, 119.0, 117.6, 114.8, 80.2, 68.7, 55.6, 52.3, 51.7, 40.9, 40.7, 37.0, 36.2, 28.2, 24.4, 22.8, 22.0.

HRMS (ES) 546.3180 (MH$^+$). C$_{29}$H$_{43}$N$_3$O$_7$ requires 546.3179.

(E/Z)-(7S,10S,13S)-13-tert-Butoxycarbonylamino-10-isobutyl-9,12-dioxo-2-oxa-8,11-diaza-bicyclo[13.2.2]nonadeca-1(18),4,15(19),16-tetraene-7-carboxylic acid methyl ester (4)

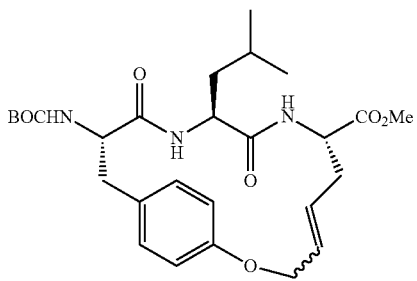

Diene 3 (1.40 g, 2.57 mmol) was dissolved in 1,1,2-trichloroethane (150 mL) under an atmosphere of argon. Chlorodicyclohexyl borane (0.257 mL, 0.257 mmol) and GSGC (0.218 g, 0.257 mmol) were added. The reaction mixture was heated at reflux in the microwave (1200 W) for 20 mins. Two further additions of GSGC (0.218 g, 0.257 mmol) were added and after each the reaction mixture was subjected to a further 20 mins heating in the microwave before being cooled and concentrated in vacuo. Purification was achieved using flash chromatography eluting with a gradient of 1/2 EtOAc/(50/70) petroleum ether to 100% EtOAc to yield a brown solid, 0.379 g, 29%. The product was obtained as a mixture of E/Z isomers. R$_f$=0.70 (2/1 EtOAc/(50/70) petroleum ether).

$^1$H-NMR for major isomer from mixture (500 MHz in CDCl$_3$) 7.01 (2H, d J=5.4 Hz, Ar—H), 6.78 (2H, d J=5.4 Hz, Ar—H), 5.87 (1H, d J=8.6 Hz, NH Gly), 5.81 (1H, d J=7.1 Hz, NH Leu), 5.40-5.58 (2H, m, OCH$_2$CHCHCH$_2$ and OCH$_2$CHCHCH$_2$), 5.34 (1H, d J=8.6 Hz, NH Tyr), 4.73 (1H, ddd J=3.2 Hz, J=8.6 Hz, J=9.2 Hz, CHCO$_2$CH$_3$), 4.55-4.68 (2H, m, OCH$_2$CHCHCH$_2$), 4.09-4.20 (2H, m, CHCH$_2$Ph and CHCH$_2$CH(CH$_3$)$_2$), 3.74 (3H, s, CO$_2$CH$_3$), 3.08 (1H, dd J=4.9 Hz, J=12.6 Hz, CHCH$_2$Ph), 2.65-2.74 (1H, m, CHCH$_2$Ph), 2.26-2.34 (2H, m, OCH$_2$CHCHCH$_2$), 1.82-1.90 (1H, m, CHCH$_2$CH(CH$_3$)$_2$), 1.52-1.58 (2H, m, CHCH$_2$CH(CH$_3$)$_2$), 1.44 (9H, s, (CH$_3$)$_3$), 0.84-0.88 (6H, m, CHCH$_2$CH(CH$_3$)$_2$).

Selected $^1$H-NMR for minor isomer from mixture: 3.77 (3H, s, CO$_2$CH$_3$), 2.48-2.52 (1H, m, CHCH$_2$Ph), 1.48 (9H, s, (CH$_3$)$_3$), 0.89-0.94 (6H, m, CH$_2$CH(CH$_3$)$_2$).

HRMS (ES) 518.2869 (MH$^+$). C$_{27}$H$_{39}$N$_3$O$_7$ requires 518.2866.

(7S,10S,13S)-13-tert-Butoxycarbonylamino-10-isobutyl-9,12-dioxo-2-oxa-8,11-diaza-bicyclo-[13.2.2]nonadeca-1(18),15(19),16-triene-7-carboxylic acid methyl ester (5)

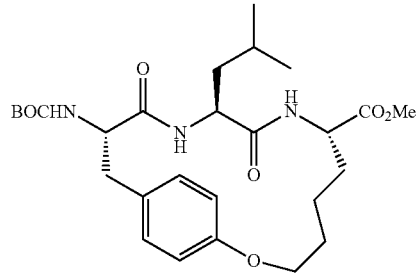

Olefin 4 (0.379 g, 0.732 mmol) was dissolved in 40 mL of EtOAc. 10% palladium on carbon catalyst was added (0.0948 g, 25%) and the reaction mixture was subjected to hydrogenation at rt and atmospheric pressure for 18 h before being filtered through celite and concentrated in vacuo to yield a brown solid, 0.341 g, 90%.

$^1$H-NMR (500 MHz in CDCl$_3$) 7.05 (2H, d J=7.8 Hz, Ar—H), 6.79 (2H, d J=7.8 Hz, Ar—H), 6.08 (1H, d J=6.1 Hz NH Gly), 5.74 (1H, d J=8.2 Hz, NH Leu), 5.22 (1H, d J=8.8 Hz, NH Tyr), 4.38-4.42 (1H, m, CHCH$_2$Ph), 4.31-4.36 (1H, m, CHCO$_2$CH$_3$), 4.12-4.28 (2H, m, OCH$_2$CH$_2$CH$_2$CH$_2$), 3.96-4.06 (1H, m, CHCH$_2$CH(CH$_3$)$_2$), 3.73 (3H, s, CO$_2$CH$_3$), 3.11 (1H, dd J=5.3 Hz, J=12.2 Hz, CHCH$_2$Ph), 2.65 (1H, dd J=12.2 Hz, J=12.2 Hz CHCH$_2$Ph), 1.68-1.74 (2H, m, OCH$_2$CH$_2$CH$_2$CH$_2$), 1.49-1.63 (3H, m, CHCH$_2$CH(CH$_3$)$_2$ and CHCH$_2$CH(CH$_3$)$_2$), 1.45 (9H, s, C(CH$_3$)$_3$), 1.20-1.40 (2H, m, OCH$_2$CH$_2$CH$_2$CH$_2$), 0.82-0.85 (6H, m, CHCH$_2$CH(CH$_3$)$_2$).

HRMS (ES) 520.3031 (MH⁺). $C_{27}H_{41}N_3O_7$ requires 520.3023.

(7S,10S,13S)-13-Amino-10-isobutyl-9,12-dioxo-2-oxa-8,11-diaza-bicyclo[13.2.2]nonadeca-1-(18),15(19),16-triene-7-carboxylic acid methyl ester hydrogen chloride salt (6)

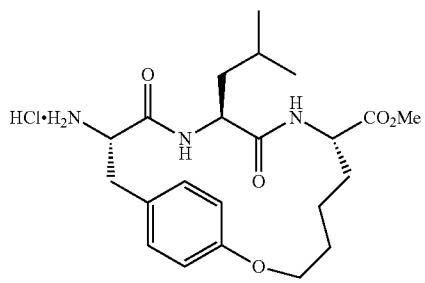

Methyl ester 5 (0.340 g, 0.654 mmol) was dissolved in 4M HCl in 1,4-dioxane (20 mL). The solution was stirred at rt for 16 h before being concentrated in vacuo to yield a brown solid, 0.232 g, 78%.

$^1$H-NMR (500 MHz in $(CD_3)_2SO$) 8.46 (2H, bs, $NH_2$), 8.32 (1H, d J=8.7 Hz NH Leu), 7.95 (1H, d J=7.8 Hz, NH Gly), 6.80 (2H, d J=8.2 Hz, Ar—H), 7.02 (2H, d J=8.2 Hz, Ar—H), 4.22-4.40 (3H, m, $CHCH_2Ph$ and $CHCH_2CH(CH_3)_2$ and $OCH_2CH_2CH_2CH_2$), 3.95-4.08 (2H, $CHCO_2CH_3$ and $OCH_2CH_2CH_2CH_2$), 3.56 (3H, s, $CO_2CH_3$), 3.12 (1H, dd J=5.9 Hz, J=12.7 Hz, $CHCH_2Ph$), 2.62 (1H, dd J=12.7 Hz, J=12.7 Hz, $CHCH_2Ph$), 1.60-1.75 (4H, m, $OCH_2CH_2CH_2CH_2$ and $OCH_2CH_2CH_2CH_2$), 1.49-1.58 (2H, m, $CHCH_2CH(CH_3)_2$) 1.44-1.48 (1H, m, $CHCH_2CH(CH_3)_2$), 1.22-1.41 (2H, m, $OCH_2CH_2CH_2CH_2$), 0.85 (3H, d J=7.3 Hz, $CHCH_2CH(CH_3)_2$), 0.84 (3H, d J=7.3 Hz, $CHCH_2CH(CH_3)_2$).

HRMS (ES) 419.2541 (MH⁺). $C_{23}H_{34}N_2O_5$ requires 419.2546.

(7S,10S,13S)-13-Benzyloxycarbonylamino-10-isobutyl-9,12-dioxo-2-oxa-8,11-diaza-bicyclo-[13.2.2]nonadeca-1(18),15(19),16-triene-7-carboxylic acid methyl ester (7)

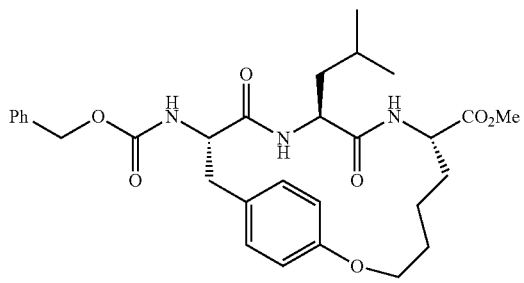 [SMILES: COC(=O)[C@@H]1CCCCOc2ccc(cc2)C[C@H](NC(=O)OCc2ccccc2)C(=O)N[C@@H](CC(C)C)C(=O)N1]

Amine 6 (4.00 g, 8.78 mmol) was dissolved in anhydrous DMF (30 mL). Benzyl chloroformate (1.88 mL, 13.2 mmol) and DIPEA (6.11 mL, 35.1 mmol) were added and the reaction mixture was stirred at rt for 18 h before being partitioned between chloroform and 1M hydrochloric acid. The aqueous phase was extracted three more times with chloroform and the combined organic extracts were dried ($MgSO_4$), filtered and concentrated in vacuo. Purification was achieved using flash chromatography, eluting with a gradient of 15% EtOAc/DCM to 50% EtOAc/DCM to yield an off-white solid, 2.10 g, 43%. $R_f$=0.43 (30% EtOAc/DCM).

$^1$H-NMR (500 MHz in $CDCl_3$) 7.31-7.38 (5H, m, Ar—H (CBZ)), 7.06 (2H, d J=7.9 Hz, Ar—H (Tyr)), 6.79 (2H, d J=7.9 Hz, Ar—H (Tyr)), 6.13 (1H, d J=6.9 Hz, NH Gly), 5.79 (1H, d J=7.9 Hz, NH Leu), 5.53 (1H, d J=8.5 Hz, NH Tyr), 5.13 (2H, s, $OCH_2Ph$), 4.51-4.57 (1H, m, $CHCH_2CH(CH_3)_2$), 4.22-4.32 (2H, m, $CHCH_2Ph$ and $OCH_2CH_2CH_2CH_2$), 4.11 (1H, ddd J=5.9 Hz, J=10.1 Hz, J=16.4 Hz, $OCH_2CH_2CH_2CH_2$), 3.95 (1H, ddd J=6.5 Hz, J=6.9 Hz, J=13.0 Hz, $CHCO_2CH_3$), 3.73 (3H, s, $CO_2CH_3$), 3.14 (1H, dd J=5.7 Hz, J=12.8 Hz, $CHCH_2Ph$), 2.67 (1H, dd J=12.8 Hz, J=12.8 Hz, $CHCH_2Ph$), 1.86-1.95 (1H, m, $CHCH_2CH(CH_3)_2$), 1.74-1.83 (2H, m, $OCH_2CH_2CH_2CH_2$), 1.22-1.58 (6H, m, $CHCH_2CH(CH_3)_2$ and $OCH_2CH_2CH_2CH_2$ and $OCH_2CH_2CH_2CH_2$), 0.88 (3H, d J=6.0 Hz, $CHCH_2CH(CH_3)_2$), 0.87 (3H, d J=6.0 Hz, $CHCH_2CH(CH_3)_2$).

$^{13}$C-NMR (75 MHz in $CDCl_3$) 172.5, 170.8, 169.7, 157.1, 155.5, 136.3, 130.1, 128.5, 128.2, 128.1, 127.9, 115.7, 66.8, 66.7, 57.1, 52.5, 51.7, 51.2, 43.3, 39.0, 31.5, 28.0, 24.5, 22.9, 22.4, 21.2.

HRMS (ES) 554.2859 (MH⁺). $C_{30}H_{39}N_3O_7$ requires 554.2866.

(7S,10S,13S)-7-Hydroxymethyl-10-isobutyl-9,12-dioxo-2-oxa-8,11-diaza-bicyclo[13.2.2]nonadeca-1(18),15(19),16-trien-13-yl)-carbamic acid benzyl ester (8)

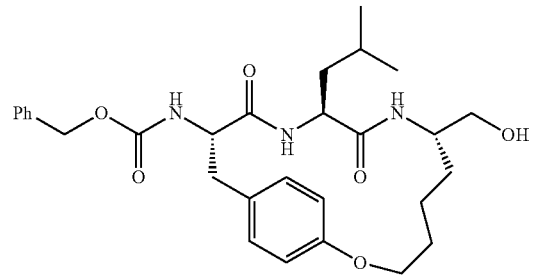 [SMILES: CC(C)C[C@@H]1NC(=O)[C@@H](NC(=O)OCc2ccccc2)Cc2ccc(cc2)OCCCC[C@@H](CO)NC1=O]

Methyl ester 7 (2.30 g, 4.15 mmol) was dissolved in anhydrous THF (40 mL) under an atmosphere of argon. The resultant solution was cooled in ice and 1M $LiAlH_4$ in diethyl ether was added (4.57 mL, 4.57 mmol). The reaction mixture was stirred in ice for 1 h and then at rt for 18 h. MeOH (30 mL) was added and the reaction mixture was stirred at rt for a further 10 mins before being concentrated in vacuo. The residue was partitioned between EtOAc and 1M aqueous $KHSO_4$. The aqueous phase was extracted twice more with chloroform and each organic extract was washed with brine before being combined, dried ($MgSO_4$), filtered and concentrated in vacuo to yield an off-white solid, 1.81 g, 83%.

$^1$H-NMR (500 MHz in $CD_3OD$) 7.68 (1H, d J=9.1 Hz, NH Gly), 7.22-7.36 (6H, m, Ar—H (CBZ) and NH Leu), 7.06 (2H, d J=7.9 Hz, Ar—H Tyr), 6.77 (2H, d J=7.9 Hz, Ar—H Tyr), 5.10 (1H, d J=12.5 Hz, $OCH_2Ph$), 5.05 (1H, d J=12.1 Hz, $OCH_2Ph$), 4.26-4.34 (2H, m, $CHCH_2Ph$ and $OCH_2CH_2CH_2CH_2$), 4.06-4.12 (1H, m, $OCH_2CH_2CH_2CH_2$), 3.96-4.02 (1H, m, $CHCH_2CH(CH_3)_2$), 3.74-3.86 (1H, m, $CHCH_2OH$), 3.30-3.33 (2H, m, $CH_2OH$), 2.98 (1H, dd J=5.4 Hz, J=12.7 Hz, CHCH$_2$Ph), 2.67 (1H, dd J=12.4 Hz, J=12.7 Hz, CHCH$_2$Ph), 1.75-1.84 (2H, m, OCH$_2$CH$_2$CH$_2$CH$_2$), 1.46-1.56 (3H, m, CHCH$_2$CH(CH$_3$)$_2$ and CHCH$_2$CH(CH$_3$)$_2$), 1.22-1.44 (4H, m, OCH$_2$CH$_2$CH$_2$CH$_2$ and OCH$_2$CH$_2$CH$_2$CH$_2$), 0.84 (3H, d J=8.8 Hz, CHCH$_2$CH(CH$_3$)$_2$), 0.83 (3H, d J=8.8 Hz, CHCH$_2$CH(CH$_3$)$_2$).

HRMS (ES) 526.2920 (MH$^+$). C$_{29}$H$_{39}$N$_3$O$_6$ requires 526.2917.

(7S,10S,13S)-7-Formyl-10-isobutyl-9,12-dioxo-2-oxa-8,11-diaza-bicyclo[13.2.2]nonadeca-1(18),15(19),16-trien-13-yl)-carbamic acid benzyl ester (9)

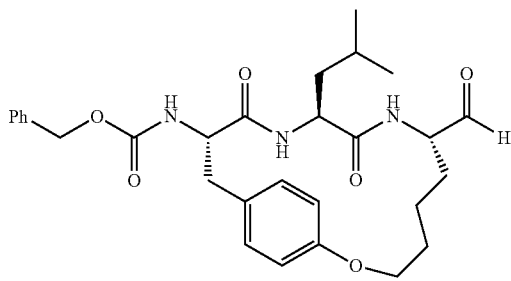 [SMILES: CC(C)C[C@@H]1NC(=O)[C@@H](NC(=O)OCc2ccccc2)Cc2ccc(cc2)OCCCC[C@@H](C=O)NC1=O]

Alcohol 8 (1.71 g, 3.25 mmol) was dissolved in DMSO (30 mL) under an atmosphere of argon. To the resultant solution DCM (15 mL) and DIPEA (2.27 mL, 13.0 mmol) were added. The reaction mixture was cooled in ice and sulfur trioxide.pyridine complex (2.07 g, 13.0 mmol) pre-dissolved in DMSO (15 mL) was added. This was stirred in ice for 2 h before being partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/2 EtOAc/(50/70) petroleum ether to EtOAc to yield a light brown solid, 0.720 g, 42%. R$_f$=0.41 (2/1 EtOAc/(50/70) petroleum ether).

This preparation was repeated, with purification by recrystallisation from MeOH, to give aldehyde 9 as white solid 1.37 g, 80%.

$^1$H-NMR (500 MHz in (CD$_3$)$_2$SO) 9.33 (1H, s, CHO), 8.05 (1H, d J=8.1 Hz, NH Leu), 7.55 (1H, d J=6.8 Hz, NH Tyr), 7.30-7.37 (5H, m, Ar—H CBZ), 7.16 (1H, d J=8.1 Hz, NH Gly), 7.02 (2H, d J=8.0 Hz, Ar—H Tyr), 6.77 (2H, d J=8.0 Hz, Ar—H Tyr), 5.06 (1H, d J=12.3 Hz, OCH$_2$Ph), 5.01 (1H, d J=12.3 Hz, OCH$_2$Ph), 4.31-4.36 (2H, m, CHCH$_2$Ph and OCH$_2$CH$_2$CH$_2$CH$_2$), 4.18-4.25 (1H, m, CHCH$_2$CH(CH$_3$)$_2$), 4.00-4.07 (2H, m, CHCHO and OCH$_2$CH$_2$CH$_2$CH$_2$), 2.86 (1H, dd J=5.6 Hz, J=12.8 Hz CHCH$_2$Ph), 2.63 (1H, dd J=12.8 Hz, J=12.8 Hz, CHCH$_2$Ph)), 1.70-1.77 (2H, m, OCH$_2$CH$_2$CH$_2$CH$_2$), 1.46-1.52 (1H, m, CHCH$_2$CH(CH$_3$)$_2$), 1.22-1.39 (6H, m, CHCH$_2$CH(CH$_3$)$_2$ and OCH$_2$CH$_2$CH$_2$CH$_2$ and OCH$_2$CH$_2$CH$_2$CH$_2$, 0.80-0.83 (6H, m, CHCH$_2$CH(CH$_3$)$_2$).

$^{13}$C-NMR (75 MHz in CDCl$_3$) 199.1, 171.1, 155.9, 137.7, 136.4, 129.3, 128.6, 128.5, 128.0, 127.9, 126.7, 66.6, 57.2, 50.2, 40.2, 38.6, 37.7, 24.8, 23.0, 21.8.

HRMS (ES) 524.2762 (MH$^+$). C$_{29}$H$_{37}$N$_3$O$_6$ requires 524.2760.

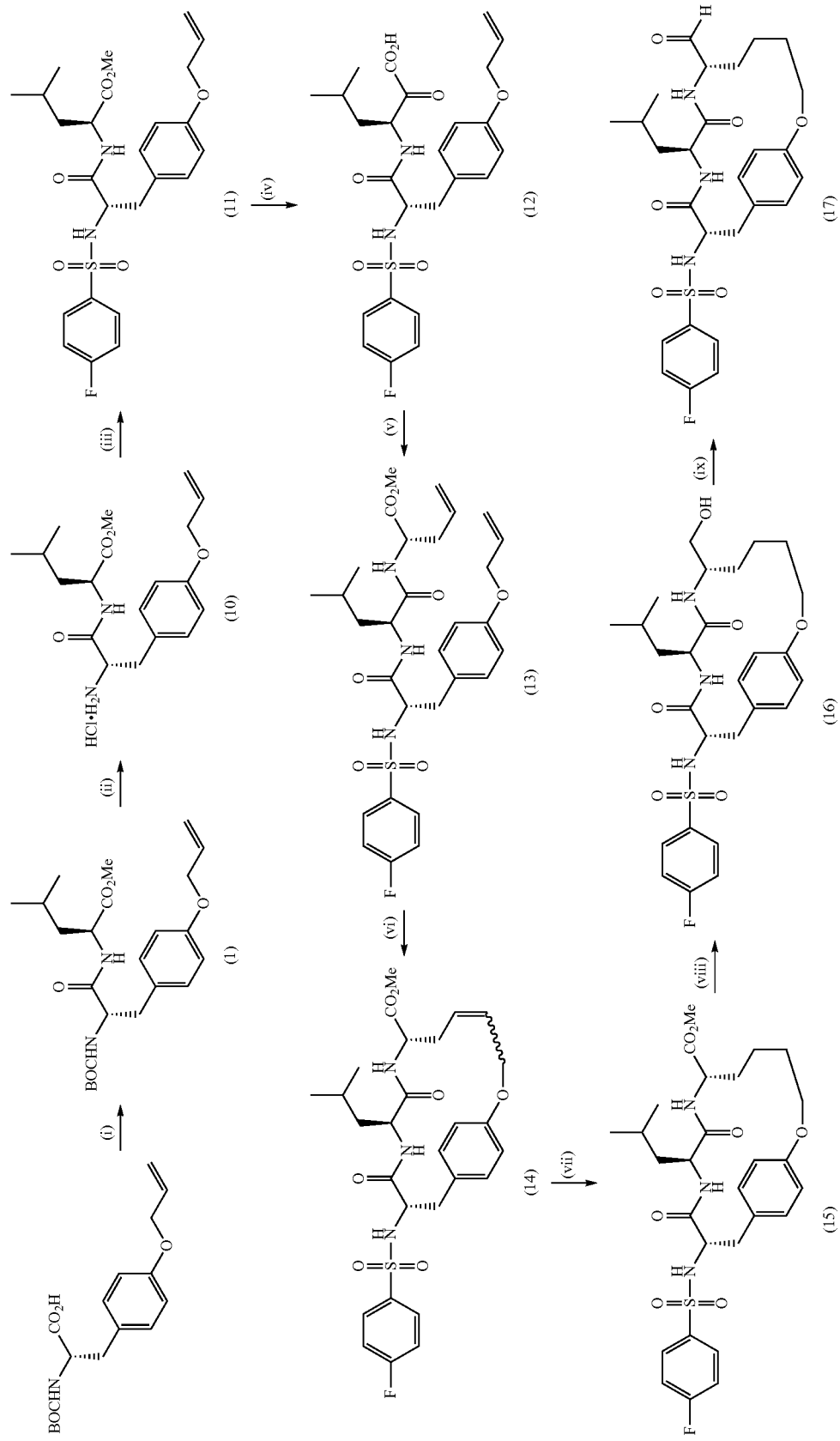
Scheme 5

Reagents and Conditions: (i) HATU, DIPEA, Leu-OMe, DMF, (80%); (ii) 4M HCl, 1,4-dioxane, (100%); (iii) 4-fluorobenzene sulfonyl chloride, DIPEA, DCM, (65%); (iv) NaOH, THF, $H_2O$, MeOH, (95%); (v) HATU, DIPEA, (s)-allyl-Gly-OMe, DMF, (89%); (vi) 3×10 mol % GSGC, 10 mol % chloro-dicyclohexyl borane, 1,1,2-TCE, microwave, (65%); (vii) $H_2$, 20 mol % Pd/C, MeOH, EtOAc, (93%); (viii) $LiAlH_4$, THF, (86%) (ix) $SO_3$.Pyr, DIPEA, DMSO, DCM (69%).

(S)-2-[(S)-3-(4-Allyloxy-phenyl)-2-amino-propionylamino]-4-methyl-pentanoic acid methyl ester hydrogen chloride salt (10)

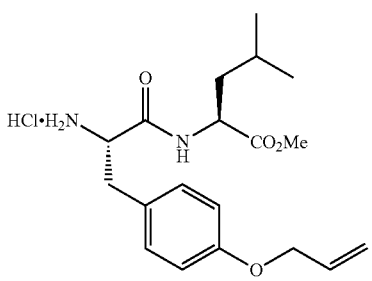

Methyl ester 1 (4.00 g, 8.92 mmol) was dissolved in 4M HCl in 1,4-dioxane (20 mL). The resultant solution was stirred at rt for 18 h before being concentrated in vacuo to yield a white solid, 3.43 g, 100%.

$^1$H-NMR (500 MHz in $CDCl_3$) 8.28 (2H, bs, $NH_2$), 7.67 (1H, d J=6.4 Hz NH Leu), 7.27 (2H, d J=8.4 Hz, Ar—H), 6.82 (2H, d J=8.4 Hz, Ar—H), 6.00 (1H, tdd J=5.2 Hz, J=5.2 Hz, J=10.3 Hz, J=16.9 Hz, $CH_2CHCH_2$), 5.22-5.40 (2H, m, $CH_2CHCH_2$), 4.57-4.64 (1H, m, $CHCH_2Ph$), 4.44 (2H, d J=5.2 Hz, $OCH_2CHCH_2$), 4.28-4.37 (1H, m, $CHCH_2CH(CH_3)_2$), 3.63 (3H, s, $CO_2CH_3$), 3.36 (1H, dd J=4.3 Hz, J=13.9 Hz, $CHCH_2Ph$), 3.20 (1H, dd J=8.2 Hz, J=13.9 Hz, $CHCH_2Ph$), 1.53-1.63 (3H, m, $CHCH_2CH(CH_3)_2$ and $CHCH_2CH(CH_3)_2$), 0.83 (3H, d J=6.7 Hz, $CHCH_2CH(CH_3)_2$), 0.82 (3H, d J=6.7 Hz, $CHCH_2CH(CH_3)_2$).

$^{13}$C-NMR (75 MHz in $CDCl_3$) 172.4, 168.2, 157.9, 133.1, 131.0, 126.2, 117.5, 114.9, 68.6, 67.0, 54.6, 52.2, 51.4, 40.1, 36.2, 24.5, 22.5, 21.9.

LRMS (ES) 349.2 ($MH^+$). $C_{19}H_{28}N_2O_6$ requires 349.2.

(S)-2-[(S)-3-(4-Allyloxy-phenyl)-2-(4-fluoro-benzenesulfonylamino)-propionylamino]-4-methyl-pentanoic acid methyl ester (11)

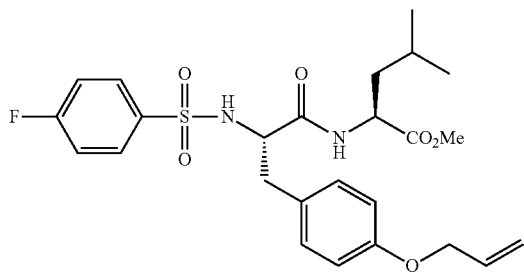

Amine 10 (3.50 g, 9.10 mmol) and 4-fluoro-benzenesulfonyl chloride (1.61 g, 8.27 mmol) were dissolved in anhydrous DCM (40 mL). DIPEA (3.17 mL, 18.2 mmol) was added and the reaction mixture was stirred at rt for 18 h before being concentrated in vacuo. The residue was partitioned between EtOAc and 1M hydrochloric acid. The organic phase was washed sequentially with 1M hydrochloric acid and brine before being dried ($MgSO_4$), filtered and concentrated in vacuo. Purification was achieved using flash chromatography, eluting with a gradient of (50/70) petroleum ether to 2/1 (EtOAc/(50/70) petroleum ether to yield a white solid, 2.70 g, 65%. $R_f$=0.81 (1/1 EtOAc/(50/70) petroleum ether).

$^1$H-NMR (500 MHz in $CDCl_3$) 7.68-7.71 (2H, m, Ar—H (4-F-Ph)), 7.06-7.11 (2H, m, Ar—H (4-F-Ph)), 6.91 (2H, d J=8.6 Hz, Ar—H (Tyr)), 6.73 (2H, d J=8.6 Hz, Ar—H (Tyr)), 6.42 (1H, d J=8.2 Hz, NH Leu), 6.05 (1H, tdd J=5.3 Hz, J=5.3 Hz, J=10.5 Hz, J=17.2 Hz, $CH_2CHCH_2$) 5.27-5.44 (2H, m, $CH_2CHCH_2$), 4.46-4.51 (3H, m, $OCH_2CHCH_2$, and $CHCH_2CH(CH_3)_2$), 3.84-3.88 (1H, m, $CHCH_2Ph$), 3.71 (3H, s, $CO_2CH_3$), 2.94 (1H, dd J=7.2 Hz, J=14.4 Hz, $CHCH_2Ph$), 2.90 (1H, dd J=6.4 Hz, J=14.4 Hz, $CHCH_2Ph$) 1.52-1.58 (1H, m, $CHCH_2CH(CH_3)_2$) 1.38-1.47 (2H, m, $CHCH_2CH(CH_3)_2$) 0.88 (6H, d J=6.2 Hz, $CHCH_2CH(CH_3)_2$).

$^{13}$C-NMR (75 MHz in $CDCl_3$) 172.5, 169.6, 157.9, 133.0, 130.2, 129.9, 129.8, 127.0, 117.8, 116.4, 116.1, 115.0, 68.7, 57.8, 52.3, 50.9, 41.4, 37.8, 24.6, 22.6, 21.8.

LRMS (ES) 507.3 ($MH^+$). $C_{25}H_{31}FN_2O_6S$ requires 507.2.

(S)-2-[(S)-3-(4-Allyloxy-phenyl)-2-(4-fluoro-benzenesulfonylamino)-propionylamino]-4-methyl-pentanoic acid (12)

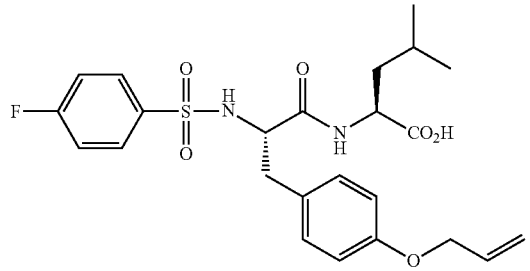 [SMILES: C=CCOc1ccc(C[C@H](NS(=O)(=O)c2ccc(F)cc2)C(=O)N[C@@H](CC(C)C)C(=O)OC)cc1]

Methyl ester 11 (2.70 g, 5.33 mmol) was dissolved in THF (30 mL). Sodium hydroxide (0.853 g, 21.3 mmol) pre-dissolved in water (10 mL) was added. Methanol (15 mL) was added to obtain a homogenous solution and this was stirred at rt for 18 h before being concentrated in vacuo. The residue was partitioned between EtOAc and 1M hydrochloric acid. The aqueous phase was extracted twice more with EtOAc and the combined organic extracts were washed with brine, dried ($MgSO_4$), filtered and concentrated in vacuo to yield a white foam, 2.50 g, 95%.

$^1$H-NMR (500 MHz in $CD_3OD$) 8.27 (1H, d, J=8.0 Hz, NH Leu), 7.60-7.63 (2H, m, Ar—H (4-F-Ph)), 7.04-7.08 (2H, m, Ar—H (4-F-Ph)) 7.02 (2H, d J=8.5 Hz, Ar—H Tyr) 6.71 (2H, d J=8.5 Hz Ar—H Tyr) 6.04 (1H, tdd J=5.2 Hz, J=5.2 Hz, J=10.5 Hz, J=17.3 Hz, $OCH_2CHCH_2$) 5.20-5.40 (2H, m, $OCH_2CHCH_2$), 4.49 (2H, d J=5.2 Hz, $OCH_2CHCH_2$), 4.22-4.27 (1H, m, $CHCH_2CH(CH_3)_2$), 3.99 (1H, dd J=4.5 Hz, J=9.5 Hz, $CHCH_2Ph$), 2.96 (1H, dd J=4.5 Hz, J=14.0 Hz, $CHCH_2Ph$), 2.65 (1H, dd J=9.5 Hz, J=14.0 Hz, $CHCH_2Ph$), 1.45-1.56 (3H, m, $CHCH_2CH(CH_3)_2$ and $CHCH_2CH(CH_3)_2$), 0.90 (3H, d J=5.8 Hz, $CHCH_2CH(CH_3)_2$), 0.84 (3H, d J=5.8 Hz, $CHCH_2CH(CH_3)_2$).

$^{13}$C-NMR (75 MHz in CDCl$_3$) 174.2, 172.0, 166.4, 157.6, 137.0, 133.7, 130.8, 130.1, 129.6, 129.4, 128.7, 116.1, 115.7, 115.4, 114.1, 68.4, 58.0, 50.6, 40.4, 37.9, 24.5, 22.0, 20.6.

LRMS (ES) 493.2 (MH$^+$). C$_{24}$H$_{29}$FN$_2$O$_6$S requires 493.2.

(S)-2-{(S)-2-[(S)-3-(4-Allyloxy-phenyl)-2-(4-fluoro-benzenesulfonylamino)-propionylamino]-4-methyl-pentanoylamino}-pent-4-enoic acid methyl ester (13)

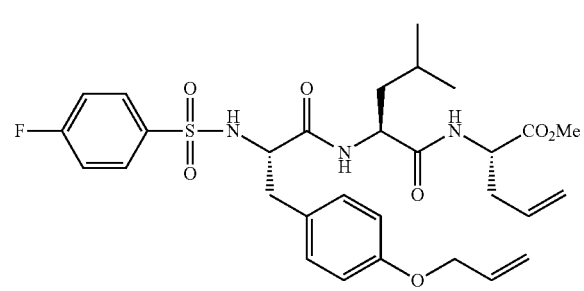 [SMILES: C=CCOc1ccc(C[C@H](NS(=O)(=O)c2ccc(F)cc2)C(=O)N[C@@H](CC(C)C)C(=O)N[C@@H](CC=C)C(=O)OC)cc1]

Carboxylic acid 12 (2.50 g, 5.08 mmol), HATU (2.13 g, 5.59 mmol) and (S)-allyl-glycine methyl ester hydrochloride (0.925 g, 5.59 mmol) were dissolved in DMF (30 mL). DIPEA was added (3.54 mL, 20.3 mmol) and the reaction mixture was stirred at rt for 18 h before being partitioned between EtOAc and 1M hydrochloric acid. The organic phase was washed sequentially with 1M hydrochloric acid and brine before being dried (MgSO$_4$), filtered and concentrated in vacuo. Purification was achieved using flash chromatography, eluting with a gradient of (50/70) petroleum ether to 2/1 EtOAc/(50/70) petroleum ether to yield a white solid, 2.70 g, 89%. R$_f$=0.38 (1/1 EtOAc/(50/70) petroleum ether).

$^1$H-NMR (500 MHz in CD$_3$OD) 7.61-7.65 (2H, m, Ar—H (4-F-Ph)), 7.06-7.10 (2H, m, Ar—H (4-F-Ph)), 6.97 (2H, d J=8.5 Hz, Ar—H Tyr), 6.69 (2H, d J=8.5 Hz, Ar—H Tyr), 6.05 (1H, tdd J=5.2 Hz, J=5.2 Hz, J=10.5 Hz, J=17.3 Hz, OCH$_2$CHCH$_2$), 5.78 (1H, tdd J=7.1 Hz, J=10.2 Hz, J=17.1 Hz, CHCH$_2$CHCH$_2$), 5.04-5.42 (4H, m, OCH$_2$CHCH$_2$ and CHCH$_2$CHCH$_2$), 4.48 (2H, d J=5.2 Hz, OCH$_2$CHCH$_2$), 4.42 (1H, dd J=5.6 Hz, J=8.0 Hz, CHCO$_2$CH$_3$), 4.32 (1H, dd J=5.0 Hz, J=9.4 Hz, CHCH$_2$CH(CH$_3$)$_2$), 3.95 (1H, dd J=4.7 Hz, J=9.5 Hz, CHCH$_2$Ph), 3.69 (3H, s, CO$_2$CH$_3$), 2.93 (1H, dd J=4.7 Hz, J=14.0 Hz, CHCH$_2$Ph), 2.63 (1H, dd J=9.5 Hz, J=14.0 Hz, CHCH$_2$Ph), 2.41-2.57 (2H, m, CHCH$_2$CHCH$_2$), 1.50-1.57 (2H, m, CHCH$_2$CH(CH$_3$)$_2$), 1.44-1.48 (1H, m, CHCH$_2$CH(CH$_3$)$_2$), 0.92 (3H, d J=6.0 Hz, CHCH$_2$CH(CH$_3$)$_2$), 0.87 (3H, d J=6.0 Hz, CHCH$_2$CH(CH$_3$)$_2$).

$^{13}$C-NMR (75 MHz in CDCl$_3$) 171.7, 171.5, 170.4, 167.3, 163.7, 157.7, 134.4, 134.3, 133.0, 132.3, 130.2, 129.9, 129.8, 127.2, 118.9, 117.7, 116.3, 116.0, 114.8, 68.6, 58.4, 52.2, 51.9, 51.9, 41.0, 37.5, 36.1, 24.6, 22.8, 21.9.

LRMS (ES) 604.3 (MH$^+$). C$_{30}$H$_{38}$FN$_3$O$_7$S requires 604.2.

(E/Z)-(7S,10S,13S)-13-(4-Fluoro-benzenesulfonylamino)-10-isobutyl-9,12-dioxo-2-oxa-8,11-diaza-bicyclo[13.2.2]nonadeca-1(18),4,15(19),16-tetraene-7-carboxylic acid methyl ester (14)

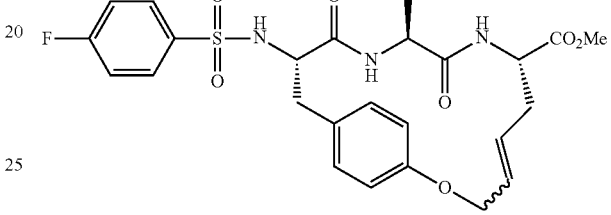

Diene 13 (1.18 g, 1.95 mmol) was dissolved in 1,1,2-trichloroethane (190 mL) under an atmosphere of argon. Chloro-dicyclohexyl borane (0.195 mL, 0.195 mmol) and GSGC (0.166 g, 0.195 mmol) were added. The reaction mixture was heated at reflux in the microwave (1200 W) for 20 mins. Two further additions of GSGC (0.166 g, 0.195 mmol) were added and after each the reaction mixture was subjected to a further 20 mins heating in the microwave. The reaction mixture was then cooled and concentrated in vacuo. Purification was achieved using flash chromatography eluting with a gradient of (50/70) petroleum ether to 100% EtOAc to yield a brown solid, 0.700 g, 63%. The product was obtained as a mixture of E/Z isomers. R$_f$=0.17 (1/1 EtOAc/(50/70) petroleum ether).

$^1$H-NMR for major isomer from mixture (500 MHz in (CD$_3$)$_2$SO) 8.18 (1H, d J=7.6 Hz, NH Tyr), 8.08 (1H, d J=8.3 Hz, NH Gly), 7.88-7.93 (2H, m, Ar—H (4-F-Ph)), 7.58 (1H, d J=7.5 Hz, NH Leu), 7.32-7.38 (2H, m, Ar—H (4-F-Ph)), 6.90 (2H, d J=7.7 Hz, Ar—H (Tyr)), 6.64 (2H, d J=7.7 Hz, Ar—H (Tyr)), 5.52-5.56 (1H, m, OCH$_2$CHCHCH$_2$), 5.39-5.46 (1H, m, OCH$_2$CHCHCH$_2$), 4.53-4.67 (2H, m, OCH$_2$CHCHCH$_2$), 4.20-4.30 (2H, m, CHCH$_2$Ph and CHCO$_2$CH$_3$), 3.78-3.85 (1H, m, CHCH$_2$CH(CH$_3$)$_2$), 3.54 (3H, s, CO$_2$CH$_3$), 2.58-2.72 (2H, m, CHCH$_2$Ph), 2.14-2.25 (2H, m, OCH$_2$CHCHCH$_2$), 1.15-1.25 (2H, m, CHCH$_2$CH(CH$_3$)$_2$), 0.99-1.05 (1H, m, CHCH$_2$CH(CH$_3$)$_2$), 0.75 (3H, d J=6.8 Hz, CHCH$_2$CH(CH$_3$)$_2$), 0.70 (3H, d J=6.8 Hz, CHCH$_2$CH(CH$_3$)$_2$).

Selected $^1$H-NMR for minor isomer from mixture: 7.15-7.22 (2H, m, Ar—H (4-F-Ph)), 7.02-7.06 (2H, m, Ar—H (Tyr)), 0.73 (3H, d J=6.8 Hz, CHCH$_2$CH(CH$_3$)$_2$), 0.69 (3H, d J=6.8 Hz, CHCH$_2$CH(CH$_3$)$_2$).

HRMS (ES) 576.2191 (MH⁺). $C_{28}H_{34}FN_3O_7S$ requires 576.2180.

(7S,10S,13S)-13-(4-Fluoro-benzenesulfonylamino)-10-isobutyl-9,12-dioxo-2-oxa-8,11-diaza-bicyclo[13.2.2]nonadeca-1(18),15(19),16-triene-7-carboxylic acid methyl ester (15)

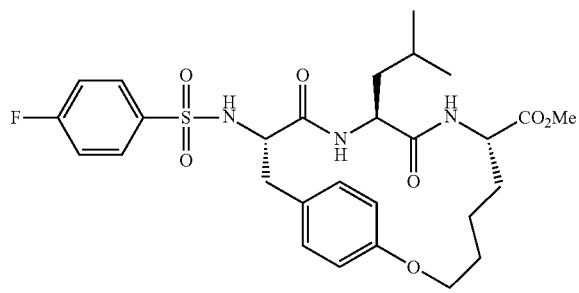 [SMILES: COC(=O)[C@@H]1CCCCOc2ccc(cc2)C[C@H](NS(=O)(=O)c2ccc(F)cc2)C(=O)N[C@@H](CC(C)C)C(=O)N1]

Olefin 14 (0.700 g, 1.22 mmol) was dissolved in a mixture of DCM (30 mL), EtOAc (10 mL) and MeOH (10 mL). 10% palladium on carbon catalyst was added (0.140 g, 20%). The reaction mixture was subjected to hydrogenation at rt and atmospheric pressure for 18 h before being filtered through celite and concentrated in vacuo to yield a brown solid, 0.667 g, 95%.

$^1$H-NMR (500 MHz in $(CD_3)_2SO$) 8.11-8.15 (2H, m, NH Tyr and NH Gly), 7.91-7.95 (1H, m, NH Leu), 7.92-7.96 (2H, m, Ar—H (4-F-Ph)), 7.33-7.37 (2H, m, Ar—H (4-F-Ph)), 6.92-6.97 (2H, m, Ar—H (Tyr)), 6.70 (2H, d J=7.9 Hz, Ar—H (Tyr)), 4.28-4.38 (2H, m, CHCOCH₃ and OCH₂CH₂CH₂CH₂), 4.11-4.21 (2H, m, CHCH₂Ph and OCH₂CH₂CH₂CH₂), 3.95-4.04 (1H, m, CHCH₂CH(CH₃)₂), 3.52 (3H, s, CO₂CH₃), 2.69-2.75 (1H, m, CHCH₂Ph), 2.54 (1H, dd J=7.1 Hz, J=12.0 Hz, CHCH₂Ph), 1.73-1.78 (2H, m, OCH₂CH₂CH₂CH₂), 1.20-1.70 (7H, m, OCH₂CH₂CH₂CH₂ and OCH₂CH₂CH₂CH₂ and CHCH₂CH(CH₃)₂ and CHCH₂CH(CH₃)₂), 0.73 (3H, d J=6.3 Hz, CHCH₂CH(CH₃)₂), 0.72 (3H, d J=6.3 Hz, CHCH₂CH(CH₃)₂).

HRMS (ES) 578.2337 (MH⁺). $C_{28}H_{36}FN_3O_7S$ requires 578.2336.

4-Fluoro-N-((7S,10S,13S)-7-hydroxymethyl-10-isobutyl-9,12-dioxo-2-oxa-8,11-diaza-bicyclo-[13.2.2]nonadeca-1(18),15(19),16-trien-13-yl)-benzenesulfonamide (16)

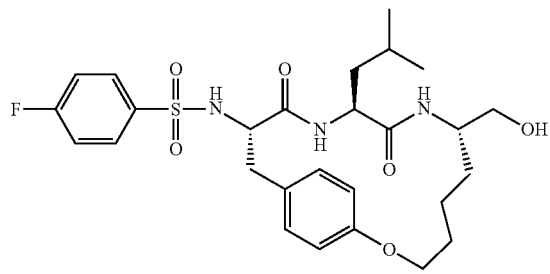 [SMILES: CC(C)C[C@@H]1NC(=O)[C@@H](NS(=O)(=O)c2ccc(F)cc2)Cc2ccc(cc2)OCCCC[C@@H](CO)NC1=O]

Methyl ester 15 (0.677 g, 1.17 mmol) was dissolved in anhydrous THF (30 mL) under an atmosphere of argon. The resultant solution was cooled in ice and 1M LiAlH₄ in diethyl ether was added (1.17 mL, 1.17 mmol). The reaction mixture was stirred in ice for 1 h and then at rt for 18 h. MeOH (30 mL) was added and the reaction mixture was stirred at rt for a further 10 mins before being concentrated in vacuo. The residue was partitioned between EtOAc and 1M aqueous KHSO₄. The aqueous phase was extracted twice more with chloroform and each organic extract was washed with brine before being combined, dried (MgSO₄), filtered and concentrated in vacuo to yield a brown solid, 0.550 g, 92%.

$^1$H-NMR (500 MHz in CD₃OD) 7.95-7.99 (2H, m, Ar—H (4-F-Ph)), 7.67 (1H, d J=8.8 Hz, NH Leu), 7.25-7.28 (2H, m, Ar—H (4-F-Ph)), 7.17 (1H, d J=7.5 Hz, NH Gly), 6.97 (2H, d J=8.0 Hz, Ar—H (Tyr)), 6.76 (2H, d J=8.0 Hz, Ar—H (Tyr)), 4.29 (1H, m, OCH₂CH₂CH₂CH₂), 4.08 (2H, m, CHCH₂Ph and OCH₂CH₂CH₂CH₂), 3.85-3.87 (2H, m, CHCH₂OH and CHCH₂CH(CH₃)₂), 3.24-3.33 (2H, m, CH₂OH), 2.88 (1H, dd J=5.5 Hz, J=12.3 Hz, CHCH₂Ph), 2.69 (1H, dd J=12.3 Hz, J=12.3 Hz, CHCH₂Ph), 1.72-1.81 (2H m, OCH₂CH₂CH₂CH₂), 1.22-1.68 (7H, m, OCH₂CH₂CH₂CH₂ and OCH₂CH₂CH₂CH₂ and CHCH₂CH(CH₃)₂ and CHCH₂CH(CH₃)₂), 0.78 (3H, d J=6.4 Hz, CHCH₂CH(CH₃)₂), 0.76 (3H, d J=6.4 Hz, CHCH₂CH(CH₃)₂).

$^{13}$C-NMR (75 MHz in CD₃OD). 171.6, 169.7, 166.6, 163.3, 157.1, 130.0, 129.8, 129.6, 127.7, 116.1, 115.8, 66.7, 64.4, 57.9, 51.8, 50.1, 43.2, 39.0, 29.7, 28.3, 24.2, 22.2, 22.1, 21.4.

HRMS (ES) 550.2369 (MH⁺). $C_{27}H_{36}FN_3O_6S$ requires 550.2387.

4-Fluoro-N-((7S,10S,13S)-7-formyl-10-isobutyl-9,12-dioxo-2-oxa-8,1'-diaza-bicyclo[13.2.2]-nonadeca-1(18),15(19),16-trien-13-yl)-benzenesulfonamide (17)

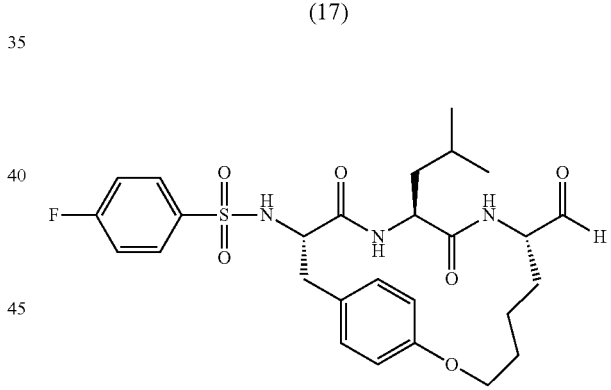

Alcohol 16 (0.57 g, 1.14 mmol) was dissolved in DMSO (12 mL) under an atmosphere of argon. To the resultant solution DCM (6 mL) and DIPEA (1.20 mL, 5.13 mmol) were added. The reaction mixture was cooled in ice and sulfur trioxide.pyridine complex (0.78 g, 4.90 mmol) pre-dissolved in DMSO (6 mL) was added. Stirring was continued in ice for 2 h before the reaction mixture was partitioned between EtOAc and 1M hydrochloric acid. The aqueous phase was extracted again with EtOAc and the combined organic extracts were dried (MgSO₄), filtered and concentrated in vacuo. Purification was achieved using flash chromatography, eluting with a gradient of (50/70) petroleum ether to EtOAc to yield a light brown solid, 0.165 g, 29%. $R_f$=0.28 (2/1 EtOAc/(50/70) petroleum ether).

$^1$H-NMR (500 MHz in $(CD_3)_2SO$) 9.29 (1H, s, CHO), 8.15 (1H, d J=8.9 Hz, NH Tyr), 8.04 (1H, d J=8.3 Hz, NH Leu), 7.93-7.97 (2H, m, Ar—H (4-F-Ph)), 7.49 (1H, d J=7.8 Hz, NH Gly), 7.33-7.38 (2H, m, Ar—H (4-F-Ph)), 6.95 (2H, d

J=7.6 Hz, Ar—H (Tyr)), 6.73 (2H, d J=7.6 Hz, Ar—H (Tyr)), 4.22-4.37 (2H, m, CHCH$_2$Ph and OCH$_2$CH$_2$CH$_2$CH$_2$), 4.17-4.24 (1H, m, CHCH$_2$CH(CH$_3$)$_2$), 3.97-4.04 (1H, m, OCH$_2$CH$_2$CH$_2$CH$_2$), 3.80-3.87 (1H, m, CHCHO), 2.72 (1H, dd J=5.2 Hz, J=12.7 Hz, CHCH$_2$Ph), 2.54-2.60 (1H, m, CHCH$_2$Ph), 1.32-1.74 (7H, m, OCH$_2$CH$_2$CH$_2$CH$_2$ and OCH$_2$CH$_2$CH$_2$CH$_2$ and CHCH$_2$CH(CH$_3$)$_2$ and CHCH$_2$CH(CH$_3$)$_2$) 0.70-0.75 (6H, m, CHCH$_2$CH(CH$_3$)$_2$).
$^{13}$C-NMR (75 MHz in (CD$_3$)$_2$SO). 201.0, 171.0, 168.4, 155.9, 130.3, 129.8, 129.7, 127.8, 116.1, 115.8, 115.5, 66.0, 56.5, 56.3, 50.5, 43.2, 26.8, 26.3, 23.8, 23.1, 22.3, 21.4.
HRMS (ES) 548.2226 (MH$^+$). C$_{27}$H$_{34}$FN$_3$O$_6$S requires 548.2230.
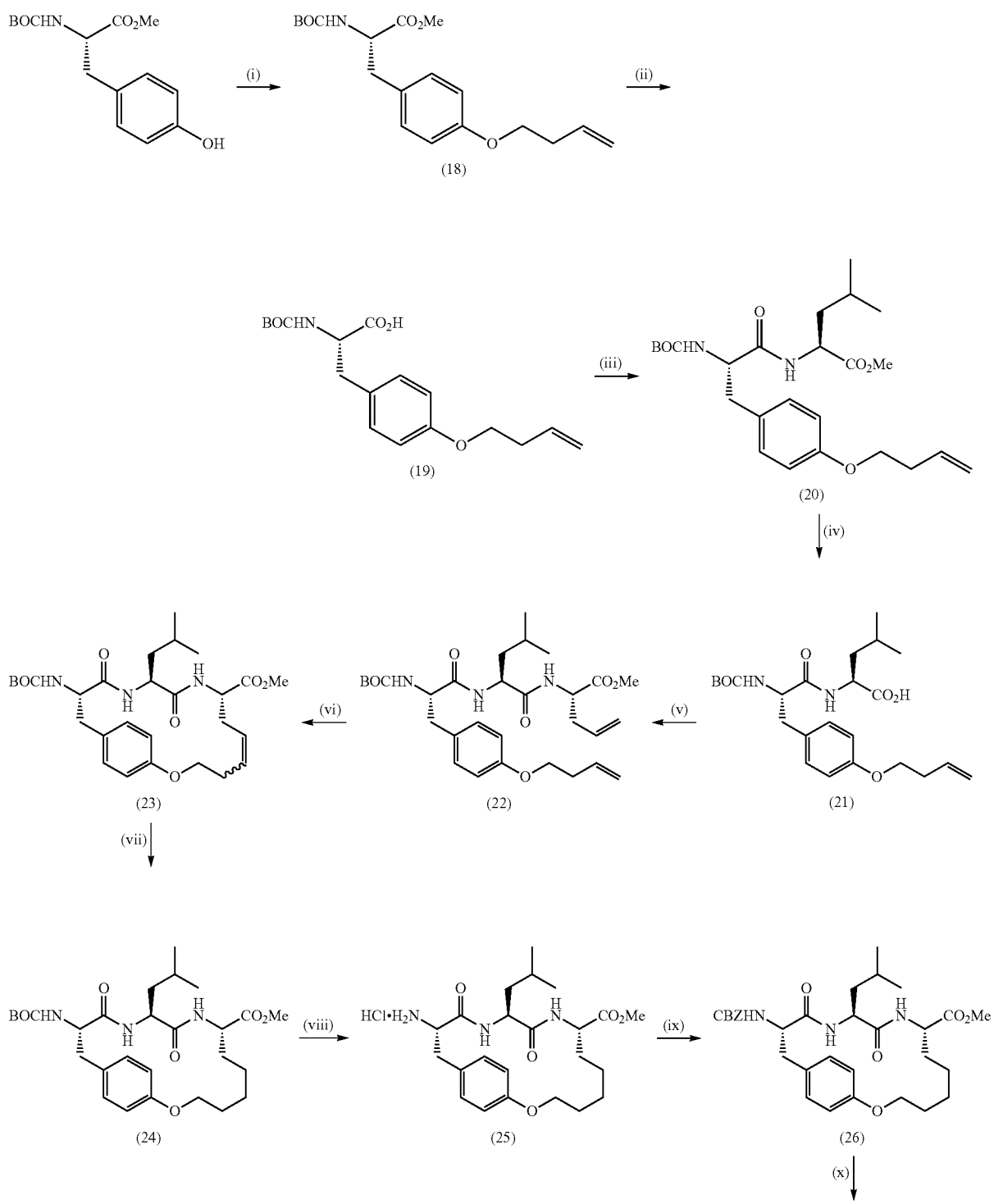
Scheme 6

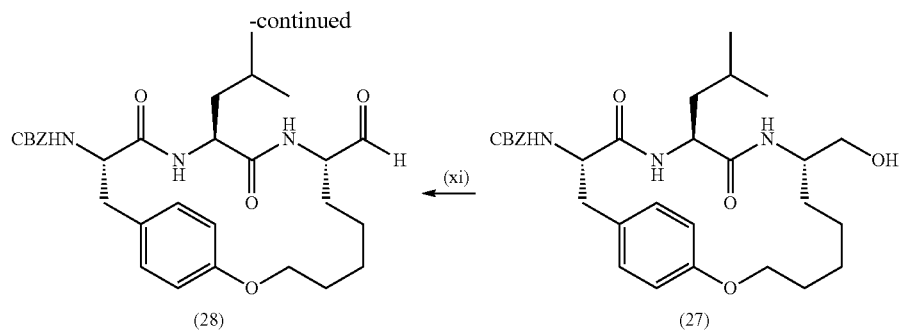

Reagents and Conditions: (i) K$_2$CO$_3$, 4-bromo-but-1-ene, DMF, (27%); (ii) NaOH, THF, H$_2$O, MeOH, (85%); (iii) HATU, DIPEA, Leu-OMe, DMF, (64%); (iv) NaOH, THF, H$_2$O, MeOH, (96%); (v) HATU, DIPEA, (s)-allyl-Gly-OMe, DMF, (84%); (vi) 3×10 mol % GSGC, 10 mol % chlorodicyclohexylborane, 1,1,2-TCE, microwave, (100%); (vii) H$_2$, 20 mol % Pd/C, MeOH, EtOAc, (26%) (viii) 4M HCl, 1,4-dioxane (100%); (ix) benzyl chloroformate, DIPEA, DMF, (69%); (x) LiAlH$_4$, THF, (72%); (xi) SO$_3$.Pyr, DIPEA, DMSO, DCM, (82%).

(S)-3-(4-But-3-enyloxy-phenyl)-2-tert-butoxycarbonylamino-propionic acid methyl ester (18)

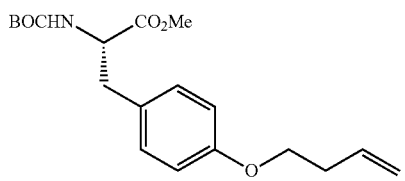

N—BOC-tyrosine methyl ester (10.0 g, 33.9 mmol) was dissolved in DMF (40 mL) and potassium carbonate (5.62 g, 40.7 mmol) and 4-bromo-1-butene (4.13 mL, 40.7 mmol) were added. The mixture was stirred at rt for 18 h before being diluted with EtOAc (120 mL) and partitioned with 1M hydrochloric acid. The organic phase was washed with hydrochloric acid and then with brine before being dried (MgSO$_4$), filtered and concentrated in vacuo. The crude material was purified by flash chromatography on silica using a gradient of EtOAc and (50/70) petroleum ether to yield a white solid, 3.20 g, 27%. R$_f$=0.82 (1/2 EtOAc/(50/70) petroleum ether).

$^1$H-NMR (500 MHz in CDCl$_3$) 7.01 (2H, d J=6.3 Hz, Ar—H), 6.82 (2H, d J=6.3 Hz, Ar—H), 5.85-5.94 (1H, m, OCH$_2$CH$_2$CHCH$_2$), 5.06-5.31 (2H, m, OCH$_2$CH$_2$CHCH$_2$), 4.95 (1H, d J=6.1 Hz, NH), 4.48-4.58 (1H, m, CHCO$_2$CH$_3$), 3.98 (2H, t J=6.4 Hz, J=6.7 Hz, J=6.7 Hz, OCH$_2$CH$_2$CHCH$_2$), 3.70 (3H, s, CHCO$_2$CH$_3$), 3.04 (1H, dd J=6.0 Hz, J=13.9 Hz, CHCH$_2$Ph), 2.98 (1H, dd J=5.0 Hz, J=13.9 Hz, CHCH$_2$Ph), 2.53 (2H, dt J=3.2 Hz, J=6.4 Hz, J=8.2 Hz, OCH$_2$CH$_2$CHCH$_2$), 1.41 (9H, s, C(CH$_3$)$_3$).

HRMS (ES) 350.1975 (MH$^+$). C$_{19}$H$_{27}$NO$_5$ requires 350.1967.

(S)-3-(4-But-3-enyloxy-phenyl)-2-tert-butoxycarbonylamino-propionic acid (19)

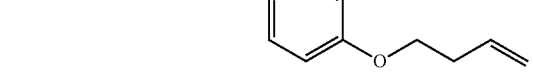

Methyl ester 18 (3.20 g, 9.16 mmol) was dissolved in THF (30 mL) and NaOH (0.552 g, 13.8 mmol) dissolved in water (10 mL) was added. Methanol (10 mL) was added to obtain a homogenous solution and this was stirred at rt for 18 h. The reaction mixture was then concentrated in vacuo and the residue was partitioned between EtOAc and 1M hydrochloric acid. The aqueous phase was extracted twice more with EtOAc and the combined organic extracts were washed with brine, dried (MgSO$_4$), filtered and concentrated in vacuo to yield a white solid, 2.60 g, 85%. m.p. 148-150° C.

$^1$H-NMR (500 MHz in CD$_3$OD) 7.11 (2H, d J=7.3 Hz, Ar—H), 6.78 (2H, d J=7.3 Hz, Ar—H), 5.91 (1H, ddt J=2.0 Hz, J=6.7 Hz, J=17.0 Hz, OCH$_2$CH$_2$CHCH$_2$), 5.05-5.16 (2H, m, OCH$_2$CH$_2$CHCH$_2$), 4.16-4.19 (1H, m, CHCO$_2$H), 3.97 (2H, t J=6.3 Hz, OCH$_2$CH$_2$CHCH$_2$), 3.09 (1H, dd J=3.9 Hz, J=13.7 Hz, CHCH$_2$Ph), 2.84 (1H, dd J=7.6 Hz, J=13.9 Hz, CHCH$_2$Ph), 2.48-2.51 (2H, m, OCH$_2$CH$_2$CHCH$_2$), 1.38 (9H, s, C(CH$_3$)$_3$).

LRMS (ES) 358.2 (MNa$^+$). C$_{18}$H$_{25}$NO$_5$Na requires 358.2.

(S)-2-[(S)-3-(4-But-3-enyloxy-phenyl)-2-tert-butoxycarbonylamino-propionylamino]-4-ethyl-pentanoic acid methyl ester (20)

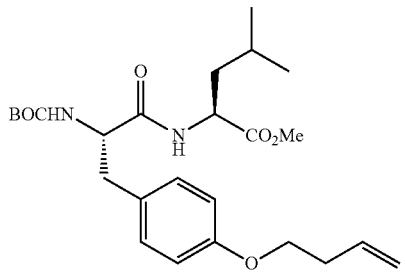

Carboxylic acid 19 (2.60 g, 7.75 mmol), HATU (3.24 g, 8.53 mmol) and leucine methyl ester hydrochloride (2.82 g, 15.5 mmol) were dissolved in DMF (40 mL). DIPEA was added (5.40 mL, 31.0 mmol) and the reaction mixture was stirred at rt for 18 h. before being partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 2.30 g, 64%. R$_f$=0.34 (1/2 EtOAc/(50/70) petroleum ether).

$^1$H-NMR (500 MHz in CDCl$_3$) 7.11 (2H, d J=8.5 Hz, Ar—H), 6.82 (2H, d J=8.5 Hz, Ar—H), 6.24 (1H, d J=7.5 Hz, NH Leu), 5.85-5.94 (1H, m, OCH$_2$CH$_2$CHCH$_2$), 5.08-5.17 (2H, m, OCH$_2$CH$_2$CHCH$_2$), 5.01 (1H, bs, NH Tyr), 4.54-4.58 (1H, m, CHCH$_2$CH(CH$_3$)$_2$), 4.27-4.32 (1H, m, CHCH$_2$Ph), 3.98 (2H, dt J=2.3 Hz, J=6.7 Hz, OCH$_2$CH$_2$CHCH$_2$), 3.69 (3H, s, CO$_2$CH$_3$), 2.95-3.05 (2H, m, CHCH$_2$Ph), 2.51-2.55 (2H, m, OCH$_2$CH$_2$CHCH$_2$), 1.53-1.60 (2H, m, CHCH$_2$CH(CH$_3$)$_2$), 1.44-1.49 (1H, m, CHCH$_2$CH(CH$_3$)$_2$), 1.42 (9H, s, C(CH$_3$)$_3$), 0.88-0.91 (6H, m, CHCH$_2$CH(CH$_3$)$_2$).

$^{13}$C-NMR (75 MHz in CDCl$_3$) 172.8, 171.0, 157.8, 134.4, 130.3, 130.2, 128.4, 116.9, 114.6, 67.1, 55.7, 52.2, 50.6, 41.5, 37.1, 33.6, 28.2, 24.6, 22.7, 21.8.

HRMS (ES) 463.2809 (MH$^+$). C$_{25}$H$_{38}$N$_2$O$_6$ requires 463.2808.

(S)-2-[(S)-3-(4-But-3-enyloxy-phenyl)-2-tert-butoxycarbonylamino-propionylamino]-4-methyl-pentanoic acid (21)

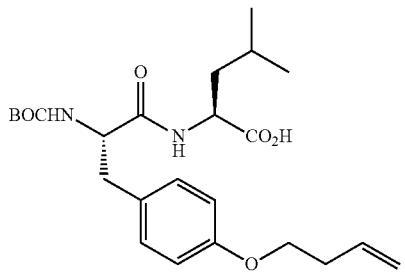

Methyl ester 20 (2.30 g, 4.97 mmol) was dissolved in THF (30 mL) and NaOH (0.298 g, 7.46 mmol) dissolved in water (10 mL) was added. Methanol (10 mL) was added to obtain a homogenous solution and this was stirred at rt for 18 h. The reaction mixture was then concentrated in vacuo and the residue was partitioned between EtOAc and 1M hydrochloric acid. The aqueous phase was extracted twice more with EtOAc and the combined organic extracts were washed with brine, dried (MgSO$_4$), filtered and concentrated in vacuo to yield a white solid, 2.14 g, 96%. m.p. 68-70° C.

$^1$H-NMR (500 MHz in CDCl$_3$) 9.41 (1H, bs, CO$_2$H), 7.09 (2H, d J=8.1 Hz, Ar—H), 6.80 (2H, d J=8.1 Hz, Ar—H), 6.70 (1H, d J=7.7 Hz, NH Leu), 5.84-5.92 (1H, m, OCH$_2$CH$_2$CHCH$_2$), 5.29 (1H, bs, NH Tyr), 5.07-5.16 (2H, m, OCH$_2$CH$_2$CHCH$_2$), 4.54-4.57 (1H, m, CHCH$_2$CH(CH$_3$)$_2$), 4.36-4.37 (1H, m, CHCH$_2$Ph), 3.95 (2H, t J=6.5 Hz, J=6.5 Hz, OCH$_2$CH$_2$CHCH$_2$), 2.93-3.02 (2H, m, CHCH$_2$Ph), 2.49-2.51 (2H, m, OCH$_2$CH$_2$CHCH$_2$) 1.50-1.69 (3H, m, CHCH$_2$CH(CH$_3$)$_2$ and CHCH$_2$CH(CH$_3$)$_2$), 1.38 (9H, s, C(CH$_3$)$_3$), 0.90-0.92 (6H, m, CHCH$_2$CH(CH$_3$)$_2$).

$^{13}$C-NMR (75 MHz in CDCl$_3$) 175.9, 171.6, 157.8, 134.4, 130.3, 130.2, 128.4, 116.9, 114.6, 67.1, 55.6, 50.8, 41.1, 37.7, 37.1, 30.6, 28.2, 24.6, 22.8, 21.8.

LRMS (ES) 449.6 (MH$^+$). C$_{24}$H$_{36}$N$_2$O$_6$ requires 449.3.

Microanalysis: C, 64.36; H, 7.92; N, 6.15. C$_{24}$H$_{36}$N$_2$O$_6$ requires C, 64.26; H, 8.09; N, 6.25.

(S)-2-{(S)-2-[(S)-3-(4-But-3-enyloxy-phenyl)-2-tert-butoxycarbonylamino-propionylamino]-4-methyl-pentanoylamino}-pent-4-enoic acid methyl ester (22)

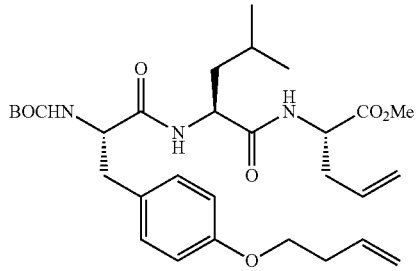

Carboxylic acid 21 (2.14 g, 4.77 mmol), HATU (2.00 g, 5.25 mmol) and (S)-allyl-glycine methyl ester hydrochloride (0.870 g, 5.25 mmol) were dissolved in DMF (30 mL). DIPEA was added (3.32 mL, 19.1 mmol) and the reaction mixture was stirred at rt for 18 h before being partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 2.24 g, 84%. R$_f$=0.32 (1/1 EtOAc/(50/70) petroleum ether). m.p. 166-168° C.

$^1$H-NMR (500 MHz in CDCl$_3$) 7.09 (2H, d J=8.4 Hz, Ar—H), 6.93 (1H, d J=7.7 Hz, NH Gly), 6.80 (2H, d J=8.4 Hz, Ar—H), 6.71 (1H, d J=7.3 Hz, NH Leu), 5.89 (1H, tdd J=6.7 Hz, J=10.1 Hz, J=17.0 Hz, OCH$_2$CH$_2$CHCH$_2$), 5.68-5.72 (1H, m, CHCH$_2$CHCH$_2$), 5.09-5.22 (4H, m, OCH$_2$CH$_2$CHCH$_2$ and CHCH$_2$CHCH$_2$), 4.54-4.60 (1H, m, CHCO$_2$CH$_3$), 4.50 (1H, ddd J=6.0 Hz, J=6.0 Hz, J=7.3 Hz, CHCH$_2$CH(CH$_3$)$_2$), 4.36-4.38 (1H, m, CHCH$_2$Ph), 3.96 (2H, t J=6.7 Hz, OCH$_2$CH$_2$CHCH$_2$), 3.73 (3H, s, CHCO$_2$CH$_3$), 2.99 (1H, dd J=6.0 Hz, J=14.0 Hz, CHCH$_2$Ph), 2.93 (1H, dd J=6.9 Hz, J=14.0 Hz, CHCH$_2$Ph), 2.45-2.58 (4H, m, CHCH$_2$CHCH$_2$ and OCH$_2$CH$_2$CHCH$_2$, 1.54-1.66 (2H, m, CHCH$_2$CH(CH$_3$)$_2$), 1.43-1.48 (1H, m, CHCH$_2$CH(CH$_3$)$_2$), 1.39 (9H, s, C(CH$_3$)$_3$), 0.86 (3H, d J=6.3 Hz, CHCH$_2$CH (CH$_3$)$_2$), 0.86 (3H, d J=6.3 Hz, CHCH$_2$CH(CH$_3$)$_2$).

$^{13}$C-NMR (75 MHz in CDCl$_3$) 171.8, 171.6, 171.5, 157.8, 134.4, 132.2, 130.3, 130.2, 128.6, 118.9, 116.9, 114.5, 79.8, 67.0, 55.6, 52.2, 51.8, 51.5, 41.1, 37.2, 36.3, 36.2, 33.6, 28.2, 24.4, 22.8, 22.2.

HRMS (ES) 560.3346 (MH$^+$). C$_{30}$H$_{45}$N$_3$O$_7$ requires 560.3336.

(E/Z)-(8S,11S,14S)-14-tert-Butoxycarbonylamino-11-isobutyl-10,13-dioxo-2-oxa-9,12-diaza-bicyclo[14.2.2]icosa-1(19),5,16(20),17-tetraene-8-carboxylic acid methyl ester (23)

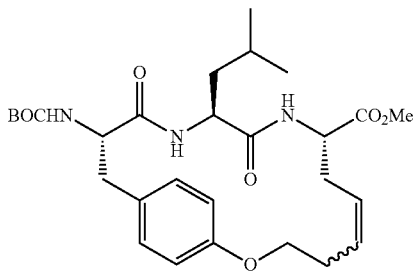

Diene 22 (2.20 g, 3.93 mmol) was dissolved in 1,1,2-trichloroethane (200 mL) under an atmosphere of argon. Chloro-dicyclohexyl borane (0.393 mL, 0.393 mmol) and GSGC (0.334 g, 0.393 mmol) were added. The reaction mixture was heated at reflux in the microwave (1200 W) for 20 mins. Two further additions of GSGC (0.334 g, 0.393 mmol) were added and after each the reaction mixture was subjected to a further 20 mins heating in the microwave. The resultant solution was allowed to cool before being concentrated in vacuo. The crude material was purified by flash chromatography on silica using a gradient of EtOAc and (50/70) petroleum ether to yield a brown solid, 2.09 g, 100%. A 1:1.9 ratio of geometric isomers was obtained. R$_f$=0.42 and 0.43 (1/1 EtOAc/(50/70) petroleum ether). m.p. 131-133° C.

$^1$H-NMR for major isomer from mixture (500 MHz in CDCl$_3$) 7.09 (2H, d J=8.1 Hz, Ar—H), 6.75 (2H, d J=8.1 Hz, Ar—H), 6.02 (1H, d J=7.8 Hz, NH Leu), 5.96 (1H, d J=8.0 Hz, NH Gly), 5.40-5.65 (2H, m, OCH$_2$CHCHCH$_2$CH$_2$ and OCH$_2$CHCHCH$_2$CH$_2$), 5.24 (1H, d J=8.3 Hz, NH Tyr), 4.93 (1H, ddd J=1.2 Hz, J=6.2 Hz, J=13.3 Hz, OCH$_2$CHCHCH$_2$CH$_2$), 4.58-4.77 (1H, m, OCH$_2$CHCHCH$_2$CH$_2$), 4.45 (1H, ddd J=3.4 Hz, J=8.6 Hz, J=8.8 Hz, CHCO$_2$CH$_3$), 4.10-4.32 (2H, m, CHCH$_2$Ph, CHCH$_2$CH(CH$_3$)$_2$), 3.74 (3H, s, CHCO$_2$CH$_3$), 3.01 (1H, dd J=4.6 Hz, J=12.8 Hz, CHCH$_2$Ph), 2.82-2.86 (1H, m, CHCH$_2$Ph), 2.37-2.48 (2H, m, OCH$_2$CHCHCH$_2$CH$_2$), 2.20-2.36 (2H, m, OCH$_2$CHCHCH$_2$CH$_2$), 1.47-1.60 (3H, m, CHCH$_2$CH(CH$_3$)$_2$ and CHCH$_2$CH(CH$_3$)$_2$), 1.45 (9H, s, C(CH$_3$)$_3$), 0.84-0.90 (6H, m, CHCH$_2$CH(CH$_3$)$_2$).

Selected $^1$H-NMR for minor isomer from mixture: 7.12 (2H, d J=8.4 Hz, Ar—H), 6.79 (2H, d J=8.4 Hz, Ar—H), 6.20 (1H, d J=7.4 Hz, NH Leu), 6.15 (1H, d J=8.6 Hz, NH Gly), 5.73 (1H, d J=7.6 Hz, NH Tyr).

HRMS (ES) 532.3034 (MH$^+$). C$_{28}$H$_{41}$N$_3$O$_7$ requires 532.3023.

(8S,11S,14S)-14-tert-Butoxycarbonylamino-11-isobutyl-10,13-dioxo-2-oxa-9,12-diaza-bicyclo[14.2.2]icosa-1(19),16(20),17-triene-8-carboxylic acid methyl ester (24)

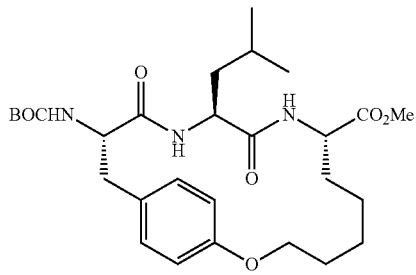

Olefin 23 (2.30 g, 4.33 mmol) was dissolved in a mixture of DCM (50 mL) and MeOH (50 mL). 10% palladium on carbon catalyst was added (0.460 g, 20%) and the reaction mixture was subjected to hydrogenation at rt and atmospheric pressure for 18 h before being filtered through celite and concentrated in vacuo to yield a brown solid, 0.600 g, 26%. m.p. 198-200° C.

$^1$H-NMR (500 MHz in CD$_3$OD) 8.13 (1H, d J=7.6 Hz, NH Leu), 7.44 (1H d J=8.3 Hz, NH Gly), 7.04 (2H, d J=8.5 Hz, Ar—H), 6.73 (2H, d J=8.5 Hz, Ar—H), 4.20-4.27 (2H, m, CHCO$_2$CH$_3$ and CHCH$_2$CH(CH$_3$)$_2$), 4.11-4.20 (2H, m, OCH$_2$CH$_2$CH$_2$CH$_2$CH$_2$ and CHCH$_2$Ph), 3.94-3.99 (1H, m, OCH$_2$CH$_2$CH$_2$CH$_2$CH$_2$), 3.65 (3H, s, CHCO$_2$CH$_3$), 2.93 (1H, dd J=4.9 Hz, J=12.6 Hz, CHCH$_2$Ph), 2.71 (1H, dd J=11.8 Hz, J=12.6 Hz, CHCH$_2$Ph), 1.63-1.74 (3H, m, OCH$_2$CH$_2$CH$_2$CH$_2$CH$_2$ and OCH$_2$CH$_2$CH$_2$CH$_2$CH$_2$), 1.51-1.60 (3H, m, CHCH$_2$CH(CH$_3$)$_2$ and CHCH$_2$CH(CH$_3$)$_2$), 1.43 (9H, s, C(CH$_3$)$_3$), 1.21-1.37 (5H, m, OCH$_2$CH$_2$CH$_2$CH$_2$CH$_2$ and OCH$_2$CH$_2$CH$_2$CH$_2$CH$_2$ and OCH$_2$CH$_2$CH$_2$CH$_2$CH$_2$), 0.86 (6H, d J=6.4 Hz, CHCH$_2$CH(CH$_3$)$_2$).

$^{13}$C-NMR (75 MHz in CD$_3$OD) 172.7, 172.1, 171.4, 157.4, 156.0, 130.0, 128.1, 114.8, 79.2, 66.3, 56.3, 51.4, 51.3, 42.6, 37.0, 31.2, 27.4, 27.3, 24.1, 23.9, 22.1, 21.6.

HRMS (ES) 534.3107 (MH$^+$). C$_{28}$H$_{43}$N$_3$O$_7$ requires 534.3179.

FTIR (KBr) 3302, 2929, 1944, 1747, 1741, 1685, 1647, 1541, 1508, 1248.

(8S,11S,14S)-14-Amino-11-isobutyl-10,13-dioxo-2-oxa-9,12-diaza-bicyclo[14.2.2]icosa-1(19),16(20),17-triene-8-carboxylic acid methyl ester hydrochloride (25)

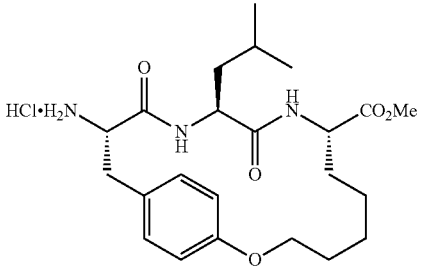

Methyl ester 24 (0.600 g, 1.12 mmol) was dissolved in 4M-HCl in 1,4-dioxane (20 mL). The resultant solution was stirred at rt for 18 h before being concentrated in vacuo to yield an off white solid, 0.528 g, 100%.

$^1$H-NMR (500 MHz in CD$_3$OD) 7.04 (2H, d J=8.1 Hz, Ar—H), 6.79 (2H, d J=8.1 Hz, Ar—H), 4.24-4.27 (1H, m, CHCO$_2$CH$_3$), 4.11-4.20 (2H, m, OCH$_2$CH$_2$CH$_2$CH$_2$CH$_2$ and CHCH$_2$CH(CH$_3$)$_2$), 4.07 (1H, dd J=4.7 Hz, J=10.9 Hz, CHCH$_2$Ph), 3.96-4.01 (1H, m, OCH$_2$CH$_2$CH$_2$CH$_2$CH$_2$), 3.64 (3H, s, CHCO$_2$CH$_3$), 3.16 (1H, dd J=4.7 Hz, J=12.5 Hz, CHCH$_2$Ph), 2.81 (1H, dd J=10.9 Hz, J=12.5 Hz, CHCH$_2$Ph), 1.69-1.79 (2H m, OCH$_2$CH$_2$CH$_2$CH$_2$CH$_2$), 1.49-1.61 (3H, m, CHCH$_2$CH(CH$_3$)$_2$ and CHCH$_2$CH(CH$_3$)$_2$), 1.34-1.47 (2H, m, OCH$_2$CH$_2$CH$_2$CH$_2$CH$_2$), 1.25-1.33 (4H, m, OCH$_2$CH$_2$CH$_2$CH$_2$CH$_2$ and OCH$_2$CH$_2$CH$_2$CH$_2$CH$_2$), 0.90 (3H, d J=6.4 Hz, CHCH$_2$CH(CH$_3$)$_2$), 0.88 (3H, d J=6.4 Hz, CHCH$_2$CH(CH$_3$)$_2$).

$^{13}$C-NMR (75 MHz in CD$_3$OD) 172.7, 171.5, 166.8, 158.1, 130.0, 125.7, 115.1, 66.4, 54.1, 51.9, 51.4, 51.3, 42.6, 36.3, 31.1, 27.3, 24.1, 24.0, 23.8, 22.0, 21.6.

HRMS (ES) 456.2444 (MNa$^+$). C$_{23}$H$_{35}$N$_3$O$_5$ requires 456.2474.

FTIR (KBr) 3327, 2931, 862, 1743, 1681, 1654, 1541, 1508.

Microanalysis: C, 58.68; H, 7.62; N, 8.63. C$_{23}$H$_{35}$N$_3$O$_5$ requires C, 58.69; H, 7.71; N, 8.93.

(8S,11S,14S)-14-Benzyloxycarbonylamino-11-isobutyl-10,13-dioxo-2-oxa-9,12-diaza-bicyclo[14.2.2]icosa-1(19),16(20),17-triene-8-carboxylic acid methyl ester (26)

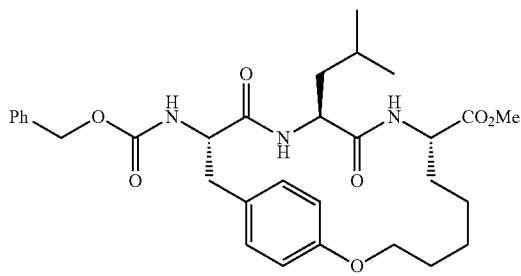 [SMILES: COC(=O)[C@@H]1CCCCCOc2ccc(cc2)C[C@H](NC(=O)OCc2ccccc2)C(=O)N[C@@H](CC(C)C)C(=O)N1]

Amine 25 (0.550 g, 1.17 mmol) was dissolved in anhydrous DMF (20 mL). Benzyl chloroformate (0.250 mL, 1.76 mmol) and DIPEA (0.815 mL, 4.68 mmol) were added and the reaction mixture was stirred at rt for 18 h before being partitioned between EtOAc and 1M hydrochloric acid. The aqueous phase was extracted twice more with EtOAc and the combined organic extracts were dried (MgSO$_4$), filtered and concentrated in vacuo. The crude material was purified by flash chromatography on silica using a gradient of EtOAc/DCM to yield an off-white solid, 0.460 g, 69%. R$_f$=0.32 (30% EtOAc/DCM). m.p. 91-93° C.

$^1$H-NMR (500 MHz in (CD$_3$)$_2$SO) 8.09 (1H, d J=7.5 Hz, NH Leu), 7.42 (1H, d J=6.9 Hz, NH Tyr), 7.30-7.36 (6H, m, NH Gly and Ar—H (CBZ)), 7.02 (2H, d J=8.3 Hz, Ar—H Tyr), 6.71 (2H, d J=8.3 Hz, Ar—H Tyr), 5.06 (1H, d J=12.7 Hz, OCH$_2$Ph), 5.01 (1H, d J=12.7 Hz, OCH$_2$Ph), 4.32-4.38 (1H, m, CHCH$_2$Ph), 4.06-4.15 (3H, m, CHCO$_2$CH$_3$ and CHCH$_2$CH(CH$_3$)$_2$ and CHCH$_2$CH$_2$CH$_2$CH$_2$CH$_2$), 3.98 (1H, td J=5.1 Hz, J=10.0 Hz, OCH$_2$CH$_2$CH$_2$CH$_2$CH$_2$), 3.57 (3H, s, CHCO$_2$CH$_3$), 2.86 (1H, dd J=5.2 Hz, J=12.1 Hz, CHCH$_2$Ph), 2.68 (1H, dd J=12.1 Hz, J=12.1 Hz, CHCH$_2$Ph), 1.61-1.68 (2H, m, OCH$_2$CH$_2$CH$_2$CH$_2$CH$_2$), 1.54-1.60 (1H, m, OCH$_2$CH$_2$CH$_2$CH$_2$CH$_2$), 1.40-1.52 (3H, m, CHCH$_2$CH(CH$_3$)$_2$ and CHCH$_2$CH(CH$_3$)$_2$), 1.16-1.36 (5H, m, OCH$_2$CH$_2$CH$_2$CH$_2$CH$_2$ and OCH$_2$CH$_2$CH$_2$CH$_2$CH$_2$ and OCH$_2$CH$_2$CH$_2$CH$_2$CH$_2$), 0.82 (3H, d J=6.5 Hz, CHCH$_2$CH(CH$_3$)$_2$), 0.80 (3H, d J=6.5 Hz, CHCH$_2$CH(CH$_3$)$_2$).

HRMS (ES) 568.3051 (MH$^+$). C$_{31}$H$_{41}$N$_3$O$_7$ requires 568.3023.

(8S,11S,14S)-8-Hydroxymethyl-11-isobutyl-10,13-dioxo-2-oxa-9,12-diaza-bicyclo-[14.2.2]icosa-1(19),16(20),17-trien-14-yl)-carbamic acid benzyl ester (27)

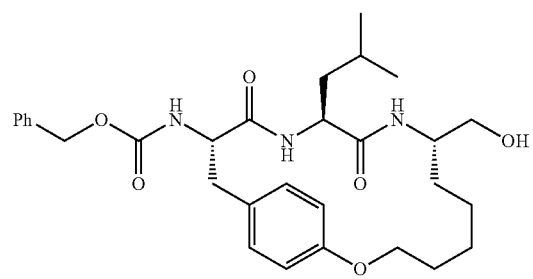 [SMILES: CC(C)C[C@@H]1NC(=O)[C@@H](NC(=O)OCc2ccccc2)Cc2ccc(cc2)OCCCCC[C@@H](CO)NC1=O]

Methyl ester 26 (0.300 g, 0.528 mmol) was dissolved in anhydrous THF (30 mL) under an atmosphere of argon. The resultant solution was cooled in ice and 1M LiAlH$_4$ in diethyl ether was added (0.581 mL, 0.581 mmol) and stirring was continued in ice for a further 1 h and then at rt for 18 h. MeOH (20 mL) was added and stirred was continued for a further 10 mins before the reaction mixture was concentrated in vacuo. The residue was partitioned between EtOAc and 1M aqueous KHSO$_4$. The aqueous phase was extracted twice more EtOAc and the combined organic extracts were washed with brine, dried (MgSO$_4$), filtered and concentrated in vacuo to yield a brown solid, 0.206 g, 72%. m.p. 208-210° C.

$^1$H-NMR (500 MHz in CD$_3$OD) 7.57 (1H, d J=9.1 Hz, NH Gly), 7.35 (1H, d J=7.3 Hz, NH Leu), 7.23-7.32 (5H, m, Ar—H (CBZ)), 7.20 (1H, d J=6.7 Hz, NH Tyr), 6.97 (2H, d J=8.2 Hz, Ar—H Tyr), 6.67 (2H, d J=8.2 Hz, Ar—H Tyr), 5.08 (1H, d J=12.2 Hz, OCH$_2$Ph), 5.02 (1H, d J=12.6 Hz, OCH$_2$Ph), 4.21 (1H, dd J=6.7 Hz, J=12.0 Hz, CHCH$_2$Ph), 4.03-4.10 (2H, m, OCH$_2$CH$_2$CH$_2$CH$_2$CH$_2$ and CHCH$_2$CH(CH$_3$)$_2$), 3.90-3.97 (1H, m, OCH$_2$CH$_2$CH$_2$CH$_2$CH$_2$), 3.56-3.58 (1H, m, CHCH$_2$OH), 3.28 (2H, d J=5.4 Hz, CHCH$_2$OH), 2.87 (1H, dd J=5.0 Hz, J=12.0 Hz, CHCH$_2$Ph), 2.68 (1H, dd J=12.0 Hz, J=12.0 Hz, CHCH$_2$Ph), 1.57-1.70 (2H, m, OCH$_2$CH$_2$CH$_2$CH$_2$CH$_2$), 1.32-1.47 (4H, m, OCH$_2$CH$_2$CH$_2$CH$_2$CH$_2$ and CHCH$_2$CH(CH$_3$)$_2$ and CHCH$_2$CH(CH$_3$)$_2$), 1.14 (5H, m, OCH$_2$CH$_2$CH$_2$CH$_2$CH$_2$ and OCH$_2$CH$_2$CH$_2$CH$_2$CH$_2$ and OCH$_2$CH$_2$CH$_2$CH$_2$CH$_2$), 0.76 (6H, d J=6.6 Hz, CHCH$_2$CH(CH$_3$)$_2$).

HRMS (ES) 540.3061 (MH$^+$). C$_{30}$H$_{41}$N$_3$O$_6$ requires 540.3073.

Microanalysis: C, 65.76; H, 7.33; N, 7.29. $C_{30}H_{41}N_3O_6 \cdot \frac{1}{2}H_2O$ requires C, 65.67; H, 7.72; N, 7.66.

(8S,11S,14S)-8-Formyl-11-isobutyl-10,13-dioxo-2-oxa-9,12-diaza-bicyclo[14.2.2]icosa-1(19),16(20),17-trien-14-yl)-carbamic acid benzyl ester (28)

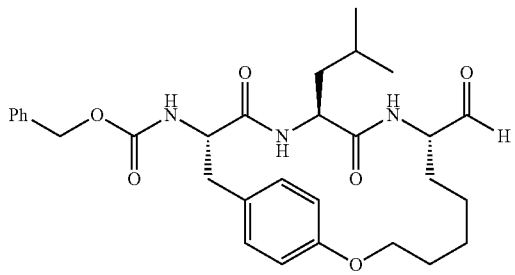 [SMILES: CC(C)C[C@@H]1NC(=O)[C@@H](NC(=O)OCc2ccccc2)Cc2ccc(cc2)OCCCCC[C@@H](C=O)NC1=O]

Alcohol 27 (0.200 g, 0.369 mmol) was dissolved in DMSO (5 mL) under an atmosphere of argon. The resultant solution was cooled in ice before DCM (5 mL), DIPEA (0.257 mL, 1.48 mmol) and sulfur trioxide.pyridine complex (0.235 g, 1.48 mmol) pre-dissolved in DMSO (5 mL) were added. The reaction mixture was stirred at 0° C. for 2 h before being partitioned between EtOAc and 1M hydrochloric acid. The aqueous phase was extracted again with EtOAc and the combined organic extracts were dried ($MgSO_4$), filtered and concentrated in vacuo to afford an off white solid, 0.269 g, 90%. m.p. 112-113° C.

$^1$H-NMR (500 MHz in $CDCl_3$) 9.49 (1H, s, CHO), 7.31-7.39 (5H, m, Ar—H (CBZ)), 7.07 (2H, d J=7.9 Hz, Ar—H (Tyr)), 6.76 (2H, d J=7.9 Hz, Ar—H (Tyr)), 6.23 (1H, d J=7.5 Hz, NH Leu), 6.09 (1H, d J=6.8 Hz, NH Gly), 5.64 (1H, d J=8.8 Hz, NH Tyr), 5.12 (2H, s, $OCH_2Ph$), 4.39 (1H, ddd J=5.4 Hz, J=6.8 Hz, J=7.4 Hz, CHCHO), 4.26-4.36 (1H, m, $CHCH_2Ph$), 4.07-4.22 (1H, m, $OCH_2CH_2CH_2CH_2CH_2$), 4.03 (1H, ddd J=5.1 Hz, J=7.5 Hz, J=10.2 Hz, $CHCH_2CH(CH_3)_2$), 3.09 (1H, dd J=4.9 Hz, J=12.6, $CHCH_2Ph$), 2.77 (1H, dd J=11.2 Hz, J=12.6 Hz, $CHCH_2Ph$), 1.70-1.82 (3H, m, $OCH_2CH_2CH_2CH_2CH_2$ and $CHCH_2CH(CH_3)_2$), 1.39-1.62 (3H, m, $OCH_2CH_2CH_2CH_2CH_2$ and $CHCH_2CH(CH_3)_2$), 1.14 (5H, m, $OCH_2CH_2CH_2CH_2CH_2$ and $OCH_2CH_2CH_2CH_2CH_2$ and $OCH_2CH_2CH_2CH_2CH_2$), 0.88 (3H, d J=5.4 Hz, $CHCH_2CH(CH_3)_2$), 0.86 (3H, d J=5.4 Hz, $CHCH_2CH(CH_3)_2$).

HRMS (ES) 538.2918 (MH$^+$). $C_{30}H_{39}N_3O_6$ requires 538.2917.

Microanalysis: C, 64.10; H, 7.22; N, 7.17. $C_{30}H_{39}N_3O_6 \cdot 1\frac{1}{2}H_2O$ requires C, 63.81; H, 7.22; N, 7.44.

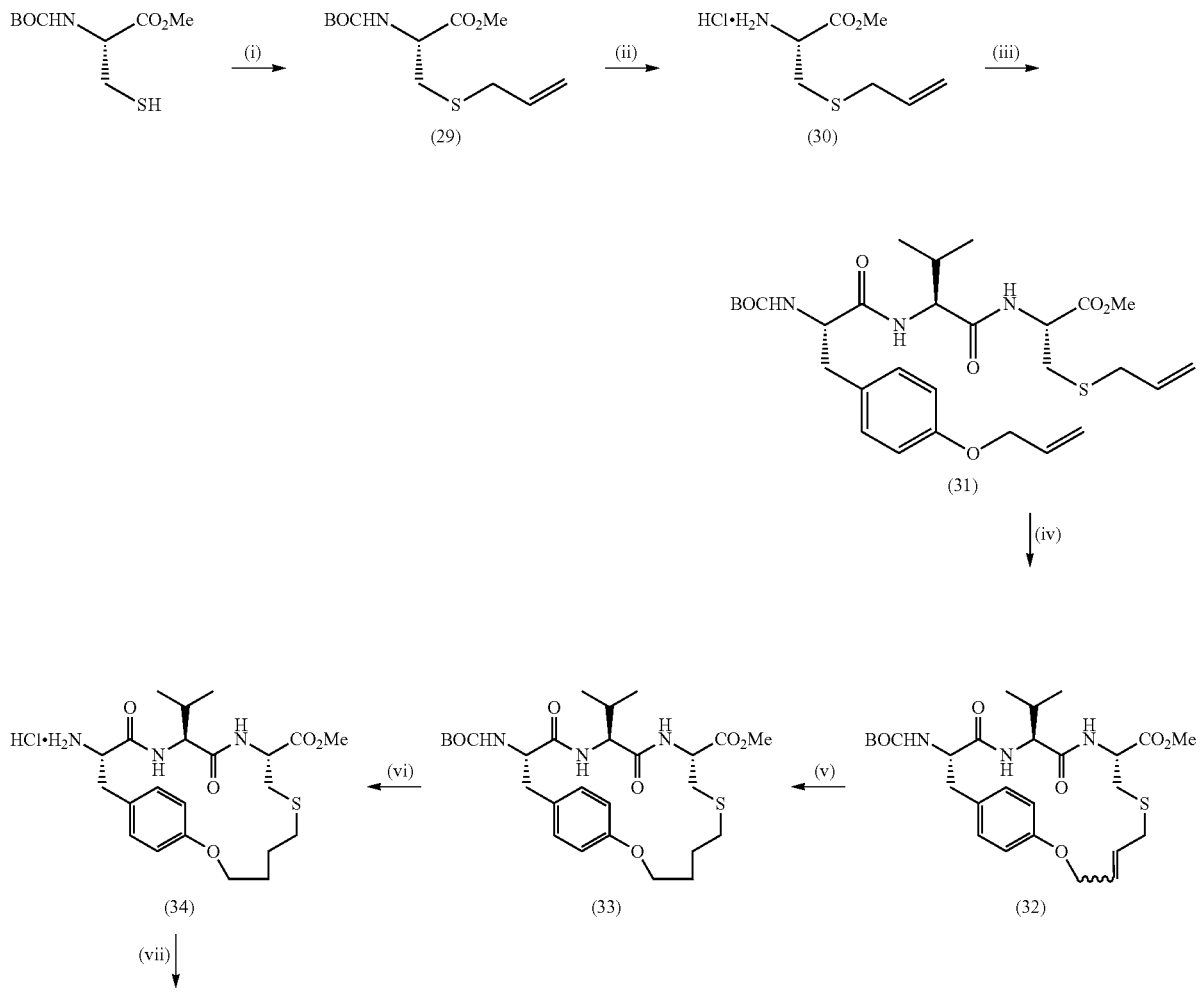

Scheme 7

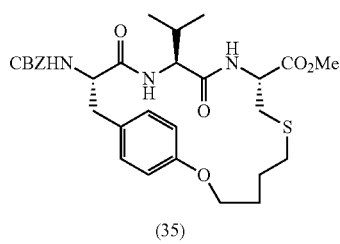 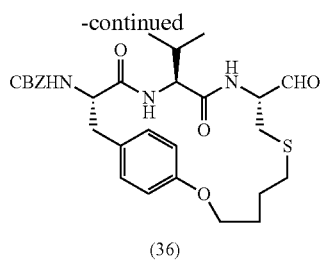

(35) (viii)→ (36)

Reagents and Conditions: (i) Et₃N, allyl bromide, DCM, (55%); (ii) HCl(g), Et₂O, (100%); (iii) HATU, DIPEA, 43, DMF, (97%); (iv) 3×10 mol % GSGC, 1,1,2-TCE, microwave, (72%); (v) H₂, 20 mol % Pd/C, MeOH, EtOAc (44%) (vi) 4M HCl, 1,4-dioxane, (100%); (vii) benzyl chloroformate, DIPEA, DMF, (18%); (viii) DIBAL-H, DCM, (17%).

(R)-3-Allylsulfanyl-2-tert-butoxycarbonylamino-propionic acid methyl ester (29)

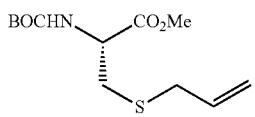

N—BOC-cysteine methyl ester (obtained from Sigma-Aldrich, Auckland, New Zealand) (5.00 g, 21.2 mmol) was dissolved in anhydrous DCM (30 mL) under an atmosphere of argon. Triethylamine (3.26 mL, 23.3 mmol) and allyl bromide (2.02 mL, 23.3 mmol) were added. The reaction mixture was stirred at rt for eighteen h before being concentrated in vacuo. The residue was partitioned between EtOAc and 1M hydrochloric acid. The organic phase was washed with brine, dried (MgSO₄), filtered and concentrated in vacuo. The crude material was purified by flash chromatography on silica using a gradient of EtOAc and (50/70) petroleum ether to yield a white solid, 3.22 g, 55%. $R_f$=0.19 (1/5 (EtOAc/(50/70) petroleum ether).

¹H-NMR (500 MHz in CDCl₃) 5.65 (1H, tdd J=7.1 Hz, J=10.1 Hz, J=17.1 Hz, CH₂CHCH₂), 5.34 (1H, d J=8.1 Hz, NH), 5.03-5.10 (2H, m, CH₂CHCH₂), 4.41-4.43 (1H, m, CHCO₂CH₃), 3.76 (3H, s, CHCO₂CH₃), 3.05-3.09 (2H, d J=5.7 Hz, CH₂CHCH₂), 2.86 (1H, dd J=4.5 Hz, J=14.8 Hz, CHCH₂S), 2.77 (1H, dd J=8.1 Hz, J=14.8 Hz, CHCH₂S), 1.41 (9H, s, C(CH₃)₃).

LRMS (ES) 276.1 (MH⁺). C₁₂H₂₁NO₄S requires 276.1.

(R)-3-Allylsulfanyl-2-amino-propionic acid methyl ester hydrochloride (30)

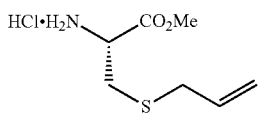

Methyl ester 29 (3.20 g, 11.6 mmol) was dissolved in 4M hydrogen chloride in 1,4-dioxane (40 mL). The resultant solution was stirred at rt for 18 h before being concentrated in vacuo to yield a white solid, 2.46 g, 100%.

¹H-NMR (500 MHz in CD₃OD) 5.78 (1H, tdd J=7.2 Hz, J=10.0 Hz, J=17.1 Hz, CH₂CHCH₂), 5.13-5.21 (2H, m, CH₂CHCH₂), 4.23 (1H, dd J=4.4 Hz, J=8.1 Hz, CHCO₂CH₃), 3.75 (3H, s, CHCO₂CH₃), 3.17-3.21 (2H, d J=7.2 Hz, CH₂CHCH₂), 3.07 (1H, dd J=4.4 Hz, J=14.8 Hz, CHCH₂S), 2.89 (1H, dd J=8.1 Hz, J=14.8 Hz, CHCH₂S).

¹³C-NMR (75 MHz in CD₃OD) 177.5, 170.2, 133.4, 52.6, 52.0, 34.1, 30.0.

LRMS (ES) 176.0 (MH⁺). C₇H₁₃NO₂S requires 176.1.

(R)-2-{(S)-2-[(S)-3-(4-Allyloxy-phenyl)-2-tert-butoxycarbonylamino-propionylamino]-3-methyl-butyrylamino}-3-allylsulfanyl-propionic acid methyl ester (31)

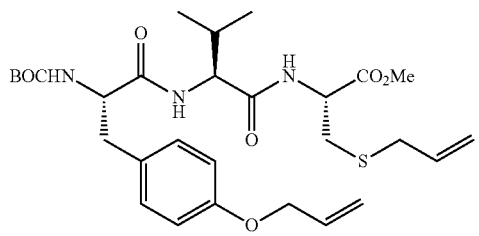

Carboxylic acid 43 (1.50 g, 3.57 mmol), HATU (2.71 g, 3.92 mmol) and amine 30 (0.831 g, 3.92 mmol) were dissolved in DMF (20 mL). DIPEA was added (2.49 mL, 14.3 mmol) and the reaction mixture was stirred at rt for 18 h before being partitioned between EtOAc and 1M hydrochloric acid. The organic phase was washed sequentially with 1M hydrochloric acid and brine before being dried (MgSO₄), filtered and concentrated in vacuo. The crude material was purified by flash chromatography on silica using a gradient of EtOAc and (50/70) petroleum ether to yield a white solid, 2.00 g, 97%. $R_f$=0.34 (1/1 EtOAc/(50/70) petroleum ether).

¹H-NMR (500 MHz in CD₃OD) 7.17 (2H, d J=8.4 Hz, Ar—H), 6.82 (2H, d J=8.4 Hz, Ar—H), 6.05 (1H, tdd J=5.3 Hz, J=10.6 Hz, J=17.4 Hz, OCH₂CHCH₂), 5.73-5.82 (1H, m, SCH₂CHCH₂), 5.06-5.41 (4H, m, OCH₂CHCH₂ and SCH₂CHCH₂), 4.54-4.61 (1H, m, CHCO₂CH₃), 4.49-4.53 (2H, m, OCH₂CHCH₂), 4.22-4.36 (2H, m, CHCH₂Ph and CHCH(CH₃)₃), 3.76 (3H, s, CHCO₂CH₃), 3.15-3.21 (2H, m, SCH₂CHCH₂), 2.74-3.04 (4H, m, CHCH₂Ph and CHCH₂SCH₂CHCH₂), 2.02-2.09 (1H, m, CHCH(CH₃)₃), 1.39 (9H, s, C(CH₃)₃), 0.96 (3H, d J=6.7 Hz, CHCH(CH₃)₃), 0.94 (3H, d J=6.7 Hz, CHCH(CH₃)₃).

HRMS (ES) 578.2892 (MH+). C29H43N3O7S requires 578.2900.

(E/Z)-(9R,12S,15S)-15-tert-Butoxycarbonylamino-12-isopropyl-11,14-dioxo-2-oxa-7-thia-10,13-diaza-bicyclo[15.2.2]henicosa-1(20),4,17(21),18-tetraene-9-carboxylic acid methyl ester (32)

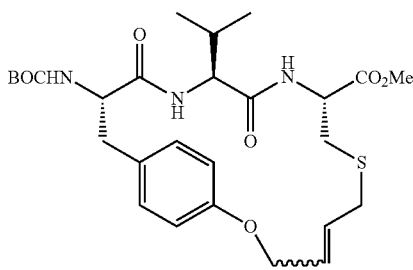

Diene 31 (1.00 g, 1.73 mmol) was dissolved in 1,1,2-trichloroethane (100 mL) under an atmosphere of argon. GSGC (0.147 g, 0.173 mmol) was added and the reaction mixture was heated at reflux in the microwave (1200 W) for 20 mins. Two further additions of GSGC (0.147 g, 0.173 mmol) were added and after each the reaction mixture was subjected to a further 20 mins heating in the microwave. The resultant solution was allowed to cool before being concentrated in vacuo. The crude material was purified by flash chromatography on silica using a gradient of EtOAc and (50/70) petroleum ether to yield a brown solid, 0.685 g, 72%. A 1:1.7 ratio of geometric isomers was obtained. $R_f$=0.25 and 0.23 (1/1 EtOAc/(50/70) petroleum ether).

$^1$H-NMR for major isomer from mixture (500 MHz in (CD$_3$)OD) 7.03 (2H, d J=8.7 Hz, Ar—H), 6.81 (2H, d J=8.7 Hz, Ar—H), 5.67-5.81 (2H, m, OCH$_2$CHCHCH$_2$) and OCH$_2$CHCHCH$_2$), 4.62-4.70 (2H, m, OCH$_2$CH$_2$CH$_2$CH$_2$S), 4.58 (1H, dd J=5.4 Hz, J=14.5 Hz, CHCO$_2$CH$_3$), 4.44-4.51 (1H, m, CHCH$_2$Ph), 4.18-4.29 (1H, m, CHCH(CH$_3$)$_2$), 3.69 (3H, s, CHCO$_2$CH$_3$), 3.08-3.22 (2H, m, OCH$_2$CH$_2$CH$_2$CH$_2$S), 3.06-3.11 (1H, m, CHCH$_2$Ph), 2.86-2.97 (1H, m, CHCH$_2$Ph), 2.67-2.86 (1H, m, CHCH$_2$S), 2.56-2.64 (1H, m, CHCH$_2$S), 1.81-1.89 (1H, m, CHCH(CH$_3$)$_2$), 1.42 (9H, s, C(CH$_3$)$_3$), 0.94 (3H, d J=6.9 Hz, CHCH(CH$_3$)$_2$), 0.92 (3H, d J=6.9 Hz, CHCH(CH$_3$)$_2$).

Selected $^1$H-NMR for minor isomer from mixture: 7.11 (2H, d J=8.0 Hz, Ar—H), 6.75 (2H, d J=8.0 Hz, Ar—H), 0.85 (3H, d J=6.5 Hz, CHCH(CH$_3$)$_2$), 0.80 (3H, d J=6.5 Hz, CHCH(CH$_3$)$_2$).

HRMS (ES) 550.2599 (MH+). C27H39N3O7S requires 550.2587.

(9R,12S,15S)-15-tert-Butoxycarbonylamino-12-isopropyl-11,14-dioxo-2-oxa-7-thia-10,13-diaza-bicyclo[15.2.2]henicosa-1(20),17(21),18-triene-9-carboxylic acid methyl ester (33)

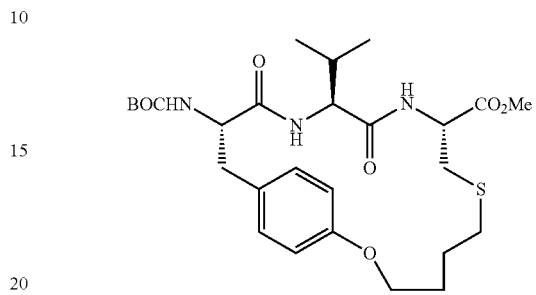

Olefin 32 (0.700 g, 1.27 mmol) was dissolved in a mixture of EtOAc (50 mL) and MeOH (20 mL). 10% palladium on carbon catalyst was added (0.140 g, 20%) and the reaction mixture was subjected to hydrogenation at rt and atmospheric pressure for 18 h. The mixture was filtered through celite and concentrated in vacuo to yield a brown solid, 0.309 g, 44%.

$^1$H-NMR (500 MHz in (CD$_3$)OD 7.03 (2H, d J=8.2 Hz, Ar—H), 6.76 (2H, d J=8.2 Hz, Ar—H), 4.58 (1H, dd J=6.0 Hz, J=14.4 Hz, CHCO$_2$CH$_3$), 4.18-4.31 (3H, m, CHCH$_2$Ph and OCH$_2$CH$_2$CH$_2$CH$_2$S), 3.98-4.02 (2H, m, OCH$_2$CH$_2$CH$_2$CH$_2$S and CHCH(CH$_3$)$_2$), 3.84-3.89 (1H, m, OCH$_2$CH$_2$CH$_2$CH$_2$S), 3.70 (3H, s, CHCO$_2$CH$_3$), 2.84-3.03 (2H, m, CHCH$_2$Ph), 2.71-2.85 (2H, m, CHCH$_2$S), 1.97-2.13 (1H, m, CHCH(CH$_3$)$_2$), 1.80-1.91 (2H, m, OCH$_2$CH$_2$CH$_2$CH$_2$S), 1.73-1.79 (2H, m, OCH$_2$CH$_2$CH$_2$CH$_2$S), 1.42 (9H, s, C(CH$_3$)$_3$), 0.94 (3H, d J=6.7 Hz, CHCH(CH$_3$)$_2$), 0.82 (3H, d J=6.7 Hz, CHCH(CH$_3$)$_2$).

HRMS (ES) 552.2739 (MH+). C27H41N3O7S requires 552.2743.

(9R,12S,15S)-15-Amino-12-isopropyl-11,14-dioxo-2-oxa-7-thia-10,13-diaza-bicyclo-[15.2.2]-henicosa-1(20),17(21),18-triene-9-carboxylic acid methyl ester hydrochloride (34)

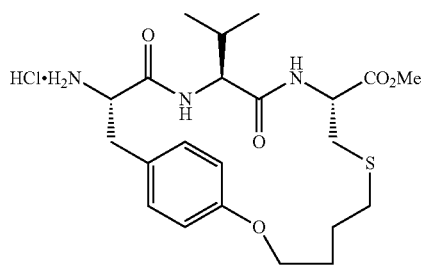

Methyl ester 33 (0.300 g, 0.544 mmol) was dissolved in 4M HCl in 1,4-dioxane (20 mL). The resultant solution was stirred at rt for 18 h before being concentrated in vacuo to yield an off white solid, 0.265 g, 100%.

$^1$H-NMR (500 MHz in (CD$_3$)$_2$SO) 8.66 (2H, bs, NH$_2$), 8.54 (1H, d J=7.3 Hz, NH), 8.18 (1H, d J=8.9 Hz, NH), 6.98

(2H, d J=8.3 Hz, Ar—H), 6.78 (2H, d J=8.3 Hz, Ar—H), 4.38-4.42 (1H, m, CHCO₂CH₃), 4.02-4.28 (4H, m, CHCH₂Ph and OCH₂CH₂CH₂CH₂S and OCH₂CH₂CH₂CH₂S), 3.89-3.95 (1H, m, CHCH(CH₃)₂), 3.84-3.88 (1H, m, OCH₂CH₂CH₂CH₂S), 3.55 (3H, s, CHCO₂CH₃), 3.06-3.14 (2H, m, CHCH₂Ph), 2.71-2.90 (2H, m, CHCH₂S), 1.93-1.98 (1H, m, CHCH(CH₃)₂), 1.60-1.75 (4H, m, OCH₂CH₂CH₂CH₂S and OCH₂CH₂CH₂CH₂S), 0.88 (3H, d J=7.1 Hz, CHCH(CH₃)₂), 0.87 (3H, d J=7.1 Hz, CHCH(CH₃)₂).

LRMS (ES) 452.3 (MH⁺). $C_{22}H_{33}N_3O_5$ requires 452.2.

(9R,12S,15S)-15-Benzyloxycarbonylamino-12-isopropyl-11,14-dioxo-2-oxa-7-thia-10,13-diaza-bicyclo[15.2.2]henicosa-1(20),17(21),18-triene-9-carboxylic acid methyl ester (35)

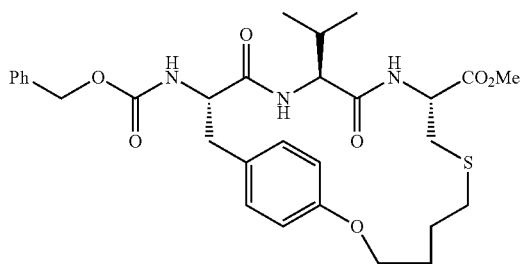 [SMILES: COC(=O)[C@@H]1CSCCCCOc2ccc(cc2)C[C@H](NC(=O)OCc2ccccc2)C(=O)N[C@@H](C(C)C)C(=O)N1]

Amine 34 (0.200 g, 0.410 mmol) was dissolved in anhydrous DMF (10 mL). Benzyl chloroformate (0.0877 mL, 0.615 mmol) and DIPEA (0.286 mL, 1.64 mmol) were added. The resultant reaction mixture was stirred at rt for 18 h before being partitioned between EtOAc and 1M hydrochloric acid. The aqueous phase was extracted twice more with EtOAc and the combined organic extracts were dried (MgSO₄), filtered and concentrated in vacuo. The crude material was purified by flash chromatography on silica using a gradient of EtOAc/DCM to yield an off-white solid, 0.0430 g, 18%. $R_f$=0.44 (30% EtOAc/DCM).

¹H-NMR (500 MHz in (CD₃OD)) (compound exists as a mixture of rotamers) 7.17-7.50 (5H, m, Ar—H (CBZ)), 6.94-7.18 (2H, m, Ar—H (Tyr)), 6.62-6.84 (2H, m, Ar—H (Tyr)), 5.02 (1H, d J=10.6 Hz, OCH₂Ph), 4.98 (1H, d J=10.6 Hz, OCH₂Ph), 4.32-4.49 (1H, m, CHCO₂CH₃), 4.14-4.33 (5H, m, CHCH₂Ph and OCH₂CH₂CH₂CH₂S and OCH₂CH₂CH₂CH₂S), 3.80-3.94 (1H, m, CHCH(CH₃)₂), 3.70 (3H, s, CHCO₂CH₃), 2.88-3.12 (2H, m, CHCH₂Ph), 2.65-2.90 (2H, m, CHCH₂S), 2.02-2.10 (1H, m, CHCH(CH₃)₂), 1.55-1.65 (4H, m, OCH₂CH₂CH₂CH₂S and OCH₂CH₂CH₂CH₂S), 0.86-0.91 (6H, m, CHCH(CH₃)₂).

HRMS (ES) 586.2566 (MH⁺). $C_{30}H_{39}N_3O_7S$ requires 586.2587.

(9R,12S,15S)-9-Formyl-12-isopropyl-11,14-dioxo-2-oxa-7-thia-10,13-diaza-bicyclo-[15.2.2]henicosa-1(20),17(21),18-trien-15-yl)-carbamic acid benzyl ester (36)

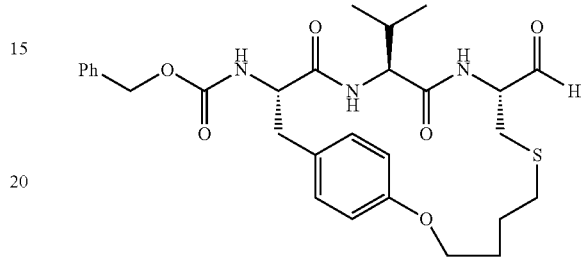

Methyl ester 35 (0.0430 g, 0.0734 mmol) was dissolved in anhydrous DCM under an atmosphere of argon. The resultant solution was cooled to −78° C. and a 1M solution of DIBAL-H in hexanes (0.403 mL, 0.404 mmol) was added dropwise. The mixture was stirred at −78° C. for three h and super-dry methanol (1:1 ratio with DCM initially added), precooled to −78° C., was added dropwise. Stirring was continued at −78° C. for a further twenty five min before the cooling bath was removed and 1M hydrochloric acid was added. The organic layer was separated from the resulting white precipitate, diluted with EtOAc and allowed to partition. The organic phase was washed sequentially with 1M hydrochloric acid, saturated aqueous NaHCO₃ and brine before being dried (MgSO₄), filtered and concentrated in vacuo. The crude material was purified by flash chromatography on silica using EtOAc to yield a brown solid, 0.00660 g, 17%. $R_f$=0.51 (EtOAc).

¹H-NMR (500 MHz in (CD₃)₂SO) 9.39 (1H, s, CHO), 7.70 (1H, d J=9.1 Hz, NH Cys), 7.66 (1H, d J=8.1 Hz, NH Val), 7.12-7.43 (5H, m, Ar—H (CBZ)), 7.05 (2H, d J=7.8 Hz, Ar—H (Tyr)), 6.78 (2H, d J=7.8 Hz, Ar—H (Tyr)), 6.62 (1H, d J=8.3 Hz, NH), 5.03 (2H, s, OCH₂Ph), 4.20-4.32 (3H, m, CHCO₂CH₃ and OCH₂CH₂CH₂CH₂S), 4.05-4.15 (3H, m, CHCH₂Ph and OCH₂CH₂CH₂CH₂S), 3.85 (1H, dd J=6.5 Hz, J=8.1 Hz, CHCH(CH₃)₂), 2.78-2.90 (2H, m, CHCH₂Ph), 2.54-2.70 (2H, m, CHCH₂S), 1.94-2.00 (1H, m, CHCH(CH₃)₂), 1.21-1.71 (4H, m, OCH₂CH₂CH₂CH₂S and OCH₂CH₂CH₂CH₂S), 0.82-0.88 (6H, m, CHCH(CH₃)₂).

HRMS (ES) 586.2480 (MH⁺). $C_{29}H_{37}N_3O_6S$ requires 556.2481.

Scheme 8

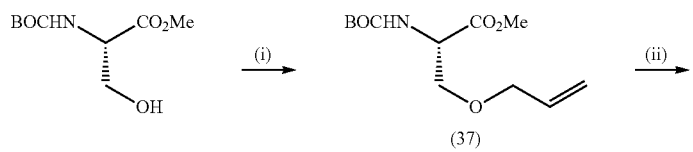

(37)

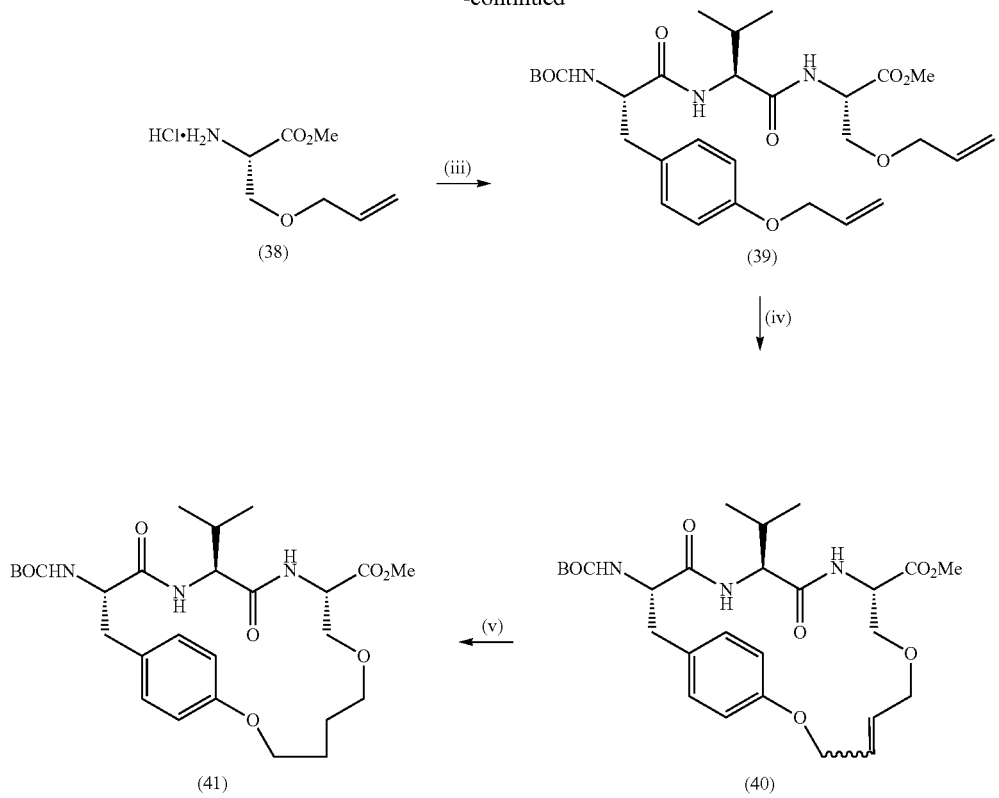

Reagents and Conditions: (i) a) allyl alcohol, ethyl chloroformate, Et₃N, Et₂O b) allyl palladium chloride, PPh₃, THF (21%); (ii) 4M HCl, 1,4-dioxane, (87%); (iii) HATU, DIPEA, 43, DMF, (62%); (iv) 3×10 mol % GSGC, 1,1,2-TCE, microwave, (23%); (v) H₂, 20 mol % Pd/C, MeOH, EtOAc (100%).

(S)-3-Allyloxy-2-tert-butoxycarbonylamino-propionic acid methyl ester (37)

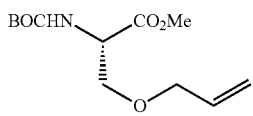

Allyl alcohol (1.97 mL, 29.0 mmol) was dissolved in diethyl ether (20 mL). This was cooled in ice before ethyl chloroformate (0.304 mL, 31.9 mmol) and triethylamine (0.445 mL, 31.9 mmol) were added. After stirring in ice for 20 mins the resultant white precipitate was removed by suction filtration. The filtrate was concentrated in vacuo and the residue dissolved in THF (4 mL). To the resultant solution a solution of allyl palladium chloride dimer (0.0849 g, 0.232 mmol) and triphenylphosphine (0.266 g, 1.02 mmol) in THF (3 mL) was added. The mixture was stirred at rt for twenty min and to this was added a solution of N-Boc-serine methyl ester (obtained from GL Biochem (Shanghai) Ltd., Shanghai, China) (5.00 g, 2.32 mmol) in THF (20 mL). The reaction mixture was stirred at rt for a further 18 h before being concentrated in vacuo. The crude material was purified by flash chromatography on silica using a gradient of EtOAc and (50/70) petroleum ether to yield a yellow oil, 1.25 g, 21%. $R_f$=0.27 (1/6 EtOAc/(50/70) petroleum ether).

¹H-NMR (500 MHz in CDCl₃) 5.64 (1H, tdd J=5.5 Hz, J=5.5 Hz, J=11.0 Hz, J=16.0 Hz, OCH₂CHCH₂), 5.37 (1H, d J=8.6 Hz, NH), 4.97-5.12 (2H, m, OCH₂CHCH₂), 4.21-4.24 (1H, m, CHCO₂CH₃), 3.74-3.80 (2H, m, OCH₂CHCH₂), 3.65 (1H, dd J=3.2 Hz, J=9.4 Hz, CHCH₂OCH₂CHCH₂), 3.55 (3H, s, CHCO₂CH₃), 3.46 (1H, dd J=3.4 Hz, J=9.4 Hz, CHCH₂OCH₂CHCH₂), 1.26 (9H, s, C(CH₃)₃).

¹³C-NMR (75 MHz in CD₃OD) 173.3, 171.4, 133.6, 118.6, 66.6, 53.1, 30.5, 26.7.

LRMS (ES) 260.2 (MH⁺). C₁₂H₂₁NO₅ requires 260.1.

(S)-3-Allyloxy-2-amino-propionic acid methyl ester hydrochloride (38)

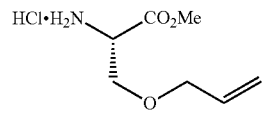

Methyl ester 37 (1.00 g, 3.86 mmol) was dissolved in 4M hydrogen chloride in 1,4-dioxane (40 mL). The resultant solution was stirred at rt for 18 h before being concentrated in vacuo to afford a white solid, 0.656 g, 87%. m.p. 87-89° C.

¹H-NMR (500 MHz in CD₃OD) 5.84-5.92 (1H, m, OCH₂CHCH₂), 5.19-5.31 (2H, m, OCH₂CHCH₂), 4.27 (1H, dd J=3.2 Hz, J=4.6 Hz, CHCO₂CH₃), 3.99-4.09 (2H, m, OCH₂CHCH₂), 3.85-3.91 (1H, m, CHCH₂OCH₂), 3.83 (3H, s, CHCO₂CH₃), 3.79 (1H, dd J=3.2 Hz, J=10.6 Hz, CHCH₂OCH₂).

LRMS (ES) 160.1 (MH⁺). C₇H₁₃NO₃ requires 160.1.

(S)-3-Allyloxy-2-{(S)-2-[(S)-3-(4-allyloxy-phenyl)-2-tert-butoxycarbonylamino-propionylamino]-3-methyl-butyrylamino}-propionic acid methyl ester (39)

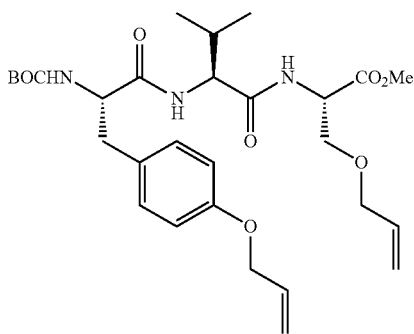

Carboxylic acid 43 (1.29 g, 3.07 mmol), HATU (1.28 g, 3.38 mmol) and amine 38 (0.660 g, 3.38 mmol) were dissolved in DMF (20 mL). DIPEA was added (2.14 mL, 12.3 mmol) and the reaction mixture was stirred at rt for 18 h before being partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 1.07 g, 62%. R$_f$=0.46 (1/1 EtOAc/(50/70) petroleum ether). m.p. 109-111° C.

$^1$H-NMR (500 MHz in CD$_3$OD) 7.12 (2H, d J=8.0 Hz, Ar—H), 6.82 (2H, d J=8.0 Hz, Ar—H), 6.04 (1H, tdd J=5.3 Hz, J=5.3 Hz, J=10.4 Hz, J=17.1 Hz, PhOCH$_2$CHCH$_2$), 5.87 (1H, dddd J=5.5 Hz, J=5.6 Hz, J=11.0 Hz, J=16.0 Hz, CH$_2$OCH$_2$CHCH$_2$), 5.13-5.40 (4H, m, PhOCH$_2$CHCH$_2$ and CH$_2$OCH$_2$CHCH$_2$), 4.59 (1H, dd J=3.2 Hz, J=4.7 Hz, CHCO$_2$CH$_3$), 4.46-4.53 (2H, m, PhOCH$_2$CHCH$_2$), 4.25-4.32 (2H, m, CHCH$_2$Ph and CHCH(CH$_3$)$_2$), 4.02 (1H, dd J=5.5 Hz, J=13.0 Hz, CH$_2$OCH$_2$CHCH$_2$), 3.97 (1H, dd J=5.6 Hz, J=13.0 Hz, CH$_2$OCH$_2$CHCH$_2$), 3.83 (1H, dd J=4.7 Hz, J=9.8 Hz, CH$_2$OCH$_2$CHCH$_2$), 3.72 (3H, s, CHCO$_2$CH$_3$), 3.67 (1H, dd J=3.8 Hz, J=8.7 Hz, CH$_2$OCH$_2$CHCH$_2$), 102 (1H, dd J=5.5 Hz, J=13.9 Hz, CHCH$_2$Ph), 2.75 (1H, dd J=8.9 Hz, J=13.9 Hz, CHCH$_2$Ph), 1.95-2.06 (1H, m, CHCH(CH$_3$)$_2$), 1.37 (9H, s, C(CH$_3$)$_3$), 0.98 (3H, d J=6.7 Hz, CHCH(CH$_3$)$_2$), 0.94 (3H, d J=6.7 Hz, CHCH(CH$_3$)$_2$).

HRMS (ES) 562.3121 (MH$^+$). C$_{29}$H$_{43}$N$_3$O$_8$ requires 562.3128.

(E/Z)-(9S,12S,15S)-15-tert-Butoxycarbonylamino-12-isopropyl-11,14-dioxo-2,7-dioxa-10,13-diaza-bicyclo[15.2.2]henicosa-1(20),4,17(21),18-tetraene-9-carboxylic acid methyl ester (40)

Diene 39 (1.06 g, 1.89 mmol) was dissolved in 1,1,2-trichloroethane (150 mL) under an atmosphere of argon. To the resultant solution GSGC (0.160 g, 0.189 mmol) was added. The reaction mixture was heated at reflux in the microwave (1200 W) for 20 mins. Two further additions of GSGC (0.160 g, 0.189 mmol) were added and after each the reaction mixture was subjected to a further 20 mins heating in the microwave. After cooling the reaction mixture was concentrated in vacuo and the crude material was purified by flash chromatography on silica using a gradient of EtOAc and (50/70) petroleum ether to yield a brown solid, 0.233 g, 23%. A 1:4.7 ratio of geometric isomers was obtained. R$_f$=0.28 and 0.27 (1/1 EtOAc/(50/70) petroleum ether).

$^1$H-NMR for major isomer from mixture (500 MHz in CDCl$_3$) 7.09 (2H, d J=8.4 Hz, Ar—H), 6.77 (2H, d J=8.4 Hz, Ar—H), 6.27 (1H, d J=8.3 Hz, NH Val), 6.24 (1H, d J=8.3 Hz, NH Ser), 5.73 (1H, ddd J=6.5 Hz, J=6.7 Hz, J=7.5 Hz, PhOCH$_2$CHCHCH$_2$), 5.62 (1H, td J=6.1 Hz, J=6.1 Hz, J=7.5 Hz, PhOCH$_2$CHCHCH$_2$), 5.40 (1H, d J=8.6 Hz, NH Tyr), 4.76 (1H, ddd J=4.0 Hz, J=4.3 Hz, J=8.3 Hz, CHCO$_2$CH$_3$), 4.67-4.61 (2H, m, PhOCH$_2$CHCHCH$_2$), 4.36 (1H, ddd J=4.2 Hz, J=8.6 Hz, J=9.6 Hz, CHCH$_2$Ph), 4.13 (1H, dd J=6.7 Hz, J=13.6 Hz, CH$_2$OCH$_2$CHCHCH$_2$), 4.09 (1H, dd J=6.5 Hz, J=13.6 Hz, CH$_2$OCH$_2$CHCHCH$_2$), 3.80 (1H, dd J=7.7 Hz, J=8.3 Hz, CHCH(CH$_3$)$_2$), 3.78 (3H, s, CHCO$_2$CH$_3$), 3.58 (1H, dd J=4.3 Hz, J=9.1 Hz, CH$_2$OCH$_2$CHCHCH$_2$), 3.51 (1H, dd J=4.0 Hz, J=9.1 Hz, CH$_2$OCH$_2$CHCHCH$_2$), 3.07 (1H, dd J=9.6 Hz, J=13.7 Hz, CHCH$_2$Ph), 2.91 (1H, dd J=4.2 Hz, J=13.7 Hz, CHCH$_2$Ph), 1.99-2.08 (1H, m, CHCH(CH$_3$)$_2$), 1.46 (9H, s, C(CH$_3$)$_3$), 0.88 (3H, d J=6.7 Hz, CHCH(CH$_3$)$_2$), 0.88 (3H, d J=6.7 Hz, CHCH(CH$_3$)$_2$).

Selected $^1$H-NMR for minor isomer from mixture: 6.80 (2H, d J=8.5 Hz, Ar—H), 4.33-4.25 (1H, m, CHCH$_2$Ph), 3.01 (1H, dd J=4.3 Hz, J=12.9 Hz, CHCH$_2$Ph), 0.85 (3H, d J=6.8 Hz, CHCH(CH$_3$)$_2$), 0.82 (3H, d J=6.5 Hz, CHCH(CH$_3$)$_2$).

HRMS (ES) 534.2820 (MH$^+$). C$_{27}$H$_{39}$N$_3$O$_8$ requires 534.2815.

(9S,12S,15S)-15-tert-Butoxycarbonylamino-12-isopropyl-11,14-dioxo-2,7-dioxa-10,13-diaza-bicyclo[15.2.2]henicosa-1(20),17(21),18-triene-9-carboxylic acid methyl ester (41)

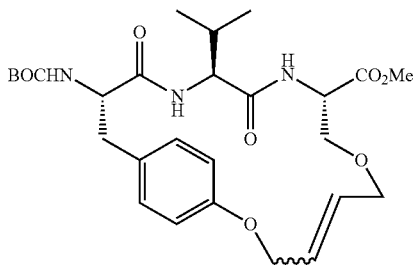

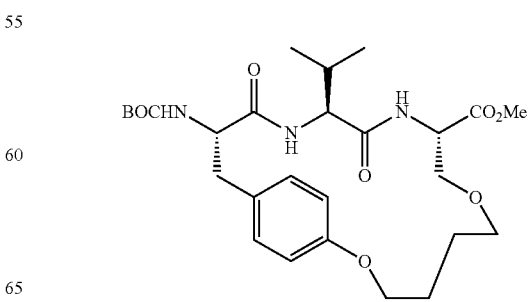

Olefin 40 (0.200 g, 0.375 mmol) was dissolved in a mixture of EtOAc (20 mL) and MeOH (20 mL). 10% palladium on carbon catalyst was added (0.0400 g, 20%) and the reaction mixture was subjected to hydrogenation at rt and atmospheric pressure for 18 h. The mixture was filtered through celite and concentrated in vacuo to yield a brown solid, 0.200 g, 100%.

$^1$H-NMR (500 MHz in CD$_3$OD) 7.05 (2H, d J=8.3 Hz, Ar—H), 6.75 (2H, d J=8.3 Hz, Ar—H), 4.60 (1H, dd J=3.9 Hz, J=6.3 Hz, CHCO$_2$CH$_3$), 4.21-4.36 (2H, m, CHCH$_2$Ph and PhOCH$_2$CH$_2$CH$_2$CH$_2$), 4.02-4.17 (3H, m, CHCH(CH$_3$)$_2$ and PhOCH$_2$CH$_2$CH$_2$CH$_2$ and CH$_2$OCH$_2$CH$_2$CH$_2$CH$_2$), 3.86-3.93 (1H, m, CH$_2$OCH$_2$CH$_2$CH$_2$CH$_2$), 3.69 (3H, s, CHCO$_2$CH$_3$), 3.47-3.55 (2H, m, CH$_2$OCH$_2$CH$_2$CH$_2$CH$_2$), 2.80-2.91 (2H, m, CHCH$_2$Ph), 1.92-2.05 (1H, m, CHCH(CH$_3$)$_2$), 1.71-1.90 (1H, m, PhOCH$_2$CH$_2$CH$_2$CH$_2$), 1.55-1.71 (3H, m, PhOCH$_2$CH$_2$CH$_2$CH$_2$ and PhOCH$_2$CH$_2$CH$_2$CH$_2$), 1.44 (9H, s, C(CH$_3$)$_3$), 0.87 (3H, d J=6.4 Hz, CHCH(CH$_3$)$_2$), 0.86 (3H, d J=6.4 Hz, CHCH(CH$_3$)$_2$).

HRMS (ES) 536.2979 (MH$^+$). C$_{27}$H$_{41}$N$_3$O$_8$ requires 536.2972.

Scheme 9

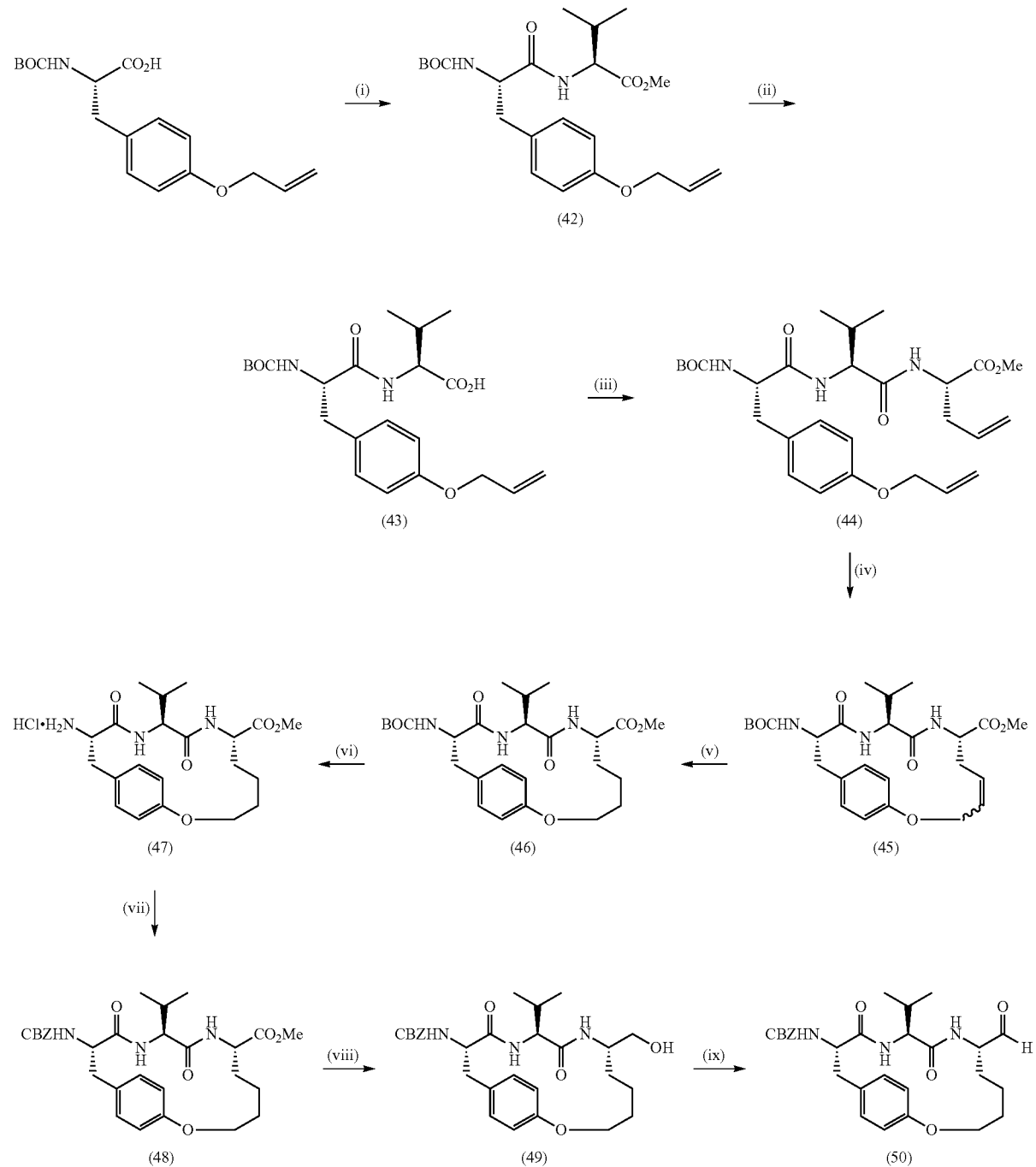

Reagents and Conditions: (i) HATU, DIPEA, Val-OMe, DMF, (69%); (ii) NaOH, THF, H$_2$O, MeOH; (97%); (iii) HATU, DIPEA, (s)-allyl-Gly-OMe, DMF, (83%); (iv) 3×10 mol % GSGC, 10 mol % chloro-dicyclohexyl borane, 1,1,2-TCE, microwave, (12%); (v) H$_2$, 20 mol % Pd/C, MeOH, EtOAc, (100%); (vi) 4M HCl, 1,4-dioxane, (100%); (vii) benzyl chloroformate, DIPEA, DMF, (70%); (viii) LiAlH$_4$, THF, (90%); (ix) SO$_3$.Pyr, DIPEA, DMSO, DCM, (81%).

(S)-2-[(S)-3-(4-Allyloxy-phenyl)-2-tert-butoxycarbonylamino-propionylamino]-3-methyl-butyric acid methyl ester (42)

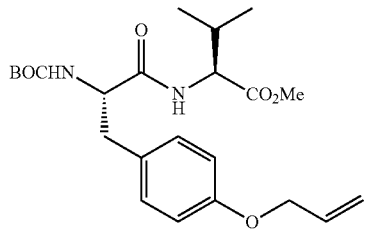

N—BOC—O-allyl-tyrosine (5.0 g, 16.3 mmol), HATU (17.9 mmol) and valine methyl ester hydrochloride (32.6 mmol) were dissolved in anhydrous DMF (25 mL). DIPEA (22.7 mL, 65 mmol) was added and the reaction mixture was stirred at rt for 18 h before being partitioned between EtOAc and 1M hydrochloric acid. The organic phase was then washed sequentially with 1M hydrochloric acid and brine before being dried (MgSO$_4$), filtered and concentrated in vacuo. Purification was achieved using flash chromatography, eluting with a gradient of (50/70) petroleum ether to EtOAc to yield a white solid, 6.08 g, 69%. R$_f$=0.29 (1/2 EtOAc/(50/70) petroleum ether). m.p. 74-76° C.

$^1$H-NMR (500 MHz in CDCl$_3$) 7.09 (2H, d J=6.5 Hz, Ar—H), 6.80 (2H, d J=6.5 Hz, Ar—H), 6.47 (1H, bs, NH Val), 5.97-6.05 (1H, m, OCH$_2$CHCH$_2$), 5.01-5.40 (2H, m, OCH$_2$CHCH$_2$), 5.12 (1H, bs, NH Tyr), 4.47-4.49 (2H, m, OCH$_2$CHCH$_2$), 4.37-4.46 (1H, m, CHCH$_2$Ph), 4.30-4.34 (1H, m, CHCH(CH$_3$)$_2$), 3.66 (3H, s, CO$_2$CH$_3$), 3.01-3.04 (2H, m, CHCH$_2$Ph), 2.04-2.11 (1H, m, CHCH(CH$_3$)$_2$), 1.39 (9H, s, C(CH$_3$)$_3$), 0.85 (3H, d J=6.8 Hz, CHCH(CH$_3$)$_2$), 0.82 (3H, d J=6.8 Hz, CHCH(CH$_3$)$_2$).

$^{13}$C-NMR (75 MHz in CDCl$_3$) 174.7, 171.9, 157.5, 133.2, 130.3, 128.6, 117.6, 114.8, 68.7, 57.2, 37.0, 31.0, 28.2, 18.8, 17.6.

HRMS (ES) 435.2501 (MH$^+$). C$_{23}$H$_{34}$N$_2$O$_6$ requires 435.2495.

Microanalysis: C, 62.58; H, 7.66; N, 6.58. C$_{23}$H$_{34}$N$_2$O$_6$ requires C, 62.84; H, 7.67; N, 6.66.

(S)-2-[(S)-3-(4-Allyloxy-phenyl)-2-tert-butoxycarbonylamino-propionylamino]-3-methyl-butyric acid (43)

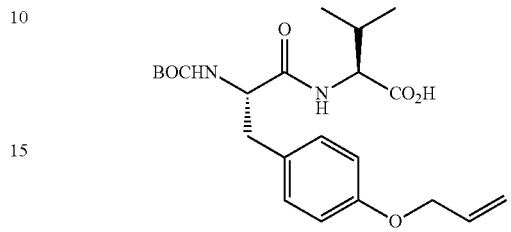

Methyl ester 42 (4.90 g, 11.3 mmol) was dissolved in THF (35 mL) and sodium hydroxide (17 mmol) pre-dissolved in water (10 mL) was added. A further 15 mL of THF and 20 mL of methanol were added to obtain a homogenous solution. The reaction mixture was stirred at rt for 18 h before being concentrated in vacuo. The residue was partitioned between EtOAc and 1M hydrochloric acid. The aqueous phase was extracted twice more with EtOAc and the combined organic extracts were washed with brine, dried (MgSO$_4$), filtered and concentrated in vacuo to yield a white foam, 4.60 g, 97%.

$^1$H-NMR (500 MHz in CDCl$_3$) 7.11 (2H, d J=8.3 Hz, Ar—H), 6.83 (2H, d J=8.3 Hz, Ar—H), 6.64 (1H, d J=8.2 Hz, NH Val), 5.98-6.07 (1H, m, OCH$_2$CHCH$_2$), 5.00-5.39 (2H, m, OCH$_2$CHCH$_2$), 5.19 (1H, bs, NH Tyr), 4.51 (3H, m, CHCH$_2$Ph and OCH$_2$CHCH$_2$), 4.36-4.40 (1H, m, CHCH (CH$_3$)$_2$), 2.97-3.02 (2H, m, CHCH$_2$Ph), 2.16-2.23 (1H, m, CHCH(CH$_3$)$_2$), 1.40 (9H, s, C(CH$_3$)$_3$), 0.88-0.93 (6H, m, CHCH(CH$_3$)$_2$).

LRMS (ES) 421.3 (MH$^+$). C$_{22}$H$_{32}$N$_2$O$_6$ requires 421.2.

(S)-2-{(S)-2-[(S)-3-(4-Allyloxy-phenyl)-2-tert-butoxycarbonylamino propionylamino]-3-methylbutyrylamino}-pent-4-enoic acid methyl ester (44)

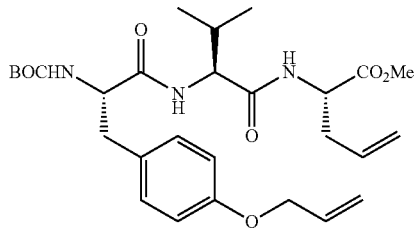

Carboxylic acid 43 (1.00 g, 2.38 mmol), HATU (2.62 mmol) and (S)-allyl-glycine methyl ester hydrochloride (2.62 mmol) were dissolved in DMF (30 mL). DIPEA was added (9.52 mmol) and the reaction mixture was stirred at rt for 18 h before being partitioned between EtOAc and 1M hydrochloric acid. The organic phase was washed sequentially with 1M hydrochloric acid and brine before being dried (MgSO$_4$), filtered and concentrated in vacuo. Purification was achieved using flash chromatography, eluting with a gradient of EtOAc and (50/70) petroleum ether to yield a white solid, 1.05 g, 83%. R$_f$=0.48 (1/1 EtOAc/(50/70) petroleum ether). m.p. 106-108° C.

¹H-NMR (500 MHz in CDCl₃) 7.09 (2H, d J=8.6 Hz, Ar—H), 6.82 (2H, d J=8.6 Hz, Ar—H), 6.61 (1H, d J=8.4 Hz, NH Val), 6.56 (1H, d J=6.8 Hz, NH Gly), 6.03 (1H, tdd J=5.3 Hz, J=10.6 Hz, J=17.2 Hz, OCH₂CHCH₂), 5.62-5.71 (1H, m, CHCH₂CHCH₂), 5.10-5.41 (4H, m, OCH₂CHCH₂ and CHCH₂CHCH₂), 5.05 (1H, d J=5.5 Hz, NH Tyr), 4.58-4.62 (1H, m, CHCH₂CHCH₂), 4.48-4.50 (2H, m, OCH₂CHCH₂), 4.30-4.33 (1H, m, CHCH₂Ph), 4.25 (1H, dd J=6.5 Hz, J=8.4 Hz, CHCH(CH₃)₂), 3.73 (3H, s, CO₂CH₃), 2.96-3.05 (2H, m, CHCH₂Ph), 2.46-2.59 (2H, m, CHCH₂CHCH₂), 2.07-2.14 (1H, m, CHCH(CH₃)₂), 1.39 (9H, s, C(CH₃)₃), 0.90 (3H, d J=6.8 Hz, CHCH(CH₃)₂), 0.86 (3H, d J=6.8 Hz, CHCH(CH₃)₂).

¹³C-NMR (75 MHz in CDCl₃) 171.7, 171.4, 170.4, 157.6, 133.2, 132.2, 130.0, 128.6, 119.3, 117.6, 114.9, 68.7, 58.4, 52.3, 51.7, 36.2, 30.7, 28.2, 19.0.

HRMS (ES) 532.3010 (MH⁺). $C_{28}H_{42}N_3O_7$ requires 532.3023.

Microanalysis: C, 63.10; H, 7.76; N, 7.90. $C_{28}H_{42}N_3O_7$ requires C, 63.26; H, 7.77; N, 7.90.

(E)-(7S,10S,13S)-13-tert-Butoxycarbonylamino-10-isopropyl-9,12-dioxo-2-oxa-8,11-diazabicyclo[13.2.2]nonadeca-1(18),4,15(19),16-tetraene-7-carboxylic acid methyl ester (45)

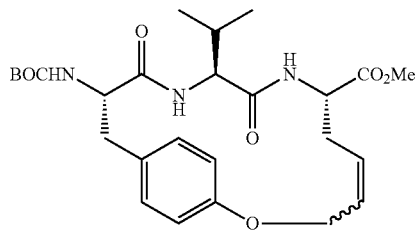

Diene 44 (1.80 g, 3.39 mmol) was dissolved in anhydrous 1,1,2-trichloroethane (0.01M) under an atmosphere of argon. GSGC (0.10 equiv) was added. The mixture was heated at reflux for one hour. Two further additions of GSGC (0.10 equiv) were added and after each the reaction mixture was subjected to one h and eighteen h of reflux respectively. This was then cooled and concentrated in vacuo. The crude material was purified by flash chromatography on silica using a gradient of EtOAc and (50/70) petroleum ether to yield a brown solid, 0.205 g, 12%. $R_f$=0.24 (1/1 EtOAc/(50/70) petroleum ether). m.p. 105-107° C.

¹H-NMR (500 MHz in CDCl₃) 7.05 (2H, d J=8.6 Hz, Ar—H), 6.75 (2H, d J=8.6 Hz, Ar—H), 5.74-5.75 (2H, m, NH Val and NH Gly), 5.43-5.56 (2H, m, OCH₂CHCHCH₂ and OCH₂CHCHCH₂), 5.32 (1H, d J=8.7 Hz, NH Tyr), 4.76 (1H, ddd J=3.4 Hz, J=9.2 Hz, J=10.1 Hz, CHCO₂CH₃), 4.58-4.64 (2H, m, OCH₂CHCHCH₂), 4.21 (1H, ddd J=5.2 Hz, J=8.7 Hz, J=11.6 Hz, CHCH₂Ph), 3.99 (1H, dd J=4.8 Hz, J=7.5 Hz, CHCH(CH₃)₂), 3.75 (3H, s, CHCO₂CH₃), 3.13 (1H, dd J=5.2 Hz, J=12.5 Hz, CHCH₂Ph), 2.66-2.75 (2H, m, CHCH₂Ph and OCH₂CHCHCH₂), 2.26-2.32 (1H, m, OCH₂CHCHCH₂), 2.07-2.14 (1H, m, CHCH(CH₃)₂), 1.45 (9H, s, C(CH₃)₃), 0.81-0.83 (6H, m, CHCH(CH₃)₂).

HRMS (ES) 504.2718 (MH⁺). $C_{26}H_{37}N_3O_7$ requires 504.2710.

(7S,10S,13S)-13-tert-Butoxycarbonylamino-10-isopropyl-9,12-dioxo-2-oxa-8,11-diazabicyclo[13.2.2]nonadeca-1(18),15(19),16-triene-7-carboxylic acid methyl ester (46)

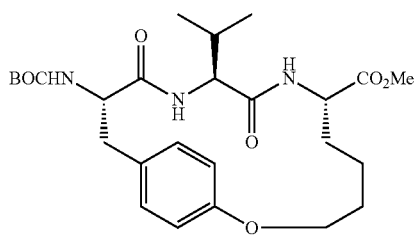

Olefin 45 (1.36 g, 2.70 mmol) was dissolved in 40 mL of EtOAc. 10% palladium on carbon catalyst was added (25%) and the reaction mixture was subjected to hydrogenation at rt and atmospheric pressure for 18 h before being filtered through celite and concentrated in vacuo to yield a brown solid, 1.36 g, 100%. m.p. 225-228° C.

¹H-NMR (500 MHz in CDCl₃) 7.05 (2H, d J=8.0 Hz, Ar—H), 6.78 (2H, d J=8.0 Hz, Ar—H), 6.23 (1H, d J=7.1 Hz, NH Val), 5.90 (1H, d J=8.2 Hz, NH Gly), 5.29 (1H, d J=8.6 Hz, NH Tyr), 4.56 (1H, dt J=3.9 Hz, J=8.2 Hz, CHCO₂CH₃), 4.21-4.30 (2H, m, CHCH₂Ph, OCH₂CH₂CH₂CH₂) 4.09-4.13 (1H, m, OCH₂CH₂CH₂CH₂), 3.84-3.86 (1H, m, CHCH(CH₃)₂), 3.72 (3H, s, CHCO₂CH₃), 3.10 (1H, dd J=5.4 Hz, J=12.2 Hz, CHCH₂Ph), 2.67 (1H, dd J=12.2 Hz, J=12.2 Hz, CHCH₂Ph), 1.95-2.02 (1H, m, CHCH(CH₃)₂), 1.86-1.92 (1H, m, OCH₂CH₂CH₂CH₂), 1.80 (1H, m, OCH₂CH₂CH₂CH₂), 1.49-1.57 (2H, m, OCH₂CH₂CH₂CH₂ and OCH₂CH₂CH₂CH₂), 1.44 (9H, s, C(CH₃)₃), 1.25-1.35 (2H, m, OCH₂CH₂CH₂CH₂), 0.87 (3H, d J=6.6 Hz, CHCH(CH₃)₂), 0.81 (3H, d J=6.6 Hz, CHCH(CH₃)₂).

¹³C-NMR (75 MHz in CDCl₃) 172.7, 170.3, 169.8, 156.9, 155.1, 130.0, 128.4, 115.9, 79.6, 66.8, 57.6, 56.8, 52.3, 51.0, 38.4, 32.3, 31.7, 28.2, 21.7, 18.2, 18.1.

HRMS (ES) 506.2871 (MH⁺). $C_{26}H_{40}N_3O_7$ requires 506.2866.

(7S,10S,13S)-13-Amino-10-isopropyl-9,12-dioxo-2-oxa-8,11-diaza-bicyclo[13.2.2]nonadeca-1-(18),15(19),16-triene-7-carboxylic acid methyl ester hydrogen chloride salt (47)

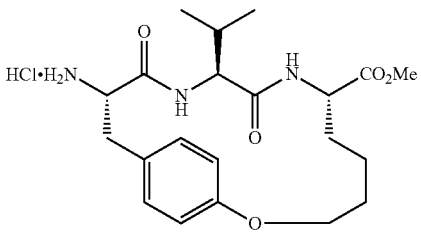

Methyl ester 46 (0.4 g) was dissolved in 4M HCl in 1,4-dioxane (10 mL). The solution was stirred at rt for 16 h before being concentrated in vacuo to yield a brown solid, 0.38 g, 100%.

(7S,10S,13S)-13-Benzyloxycarbonylamino-10-isobutyl-9,12-dioxo-2-oxa-8,11-diaza-bicyclo-[13.2.2]nonadeca-1(18),15(19),16-triene-7-carboxylic acid methyl ester (48)

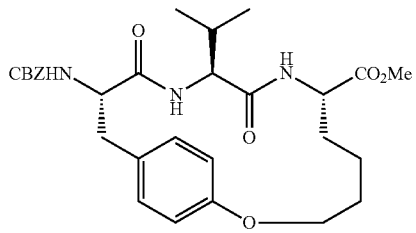

Amine 47 (65 mg) was dissolved in anhydrous DMF (30 mL). Benzyl chloroformate (0.29 mL) and DIPEA (0.75 mL) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 15% EtOAc/DCM to 50% EtOAc/DCM to yield an off-white solid, 54 mg, 70%. R$_f$=0.33 (30% EtOAc/DCM).

(7S,10S,13S)-7-Hydroxymethyl-10-isobutyl-9,12-dioxo-2-oxa-8,11-diaza-bicyclo[13.2.2]-nona-deca-1(18),15(19),16-trien-13-yl)-carbamic acid benzyl ester (49)

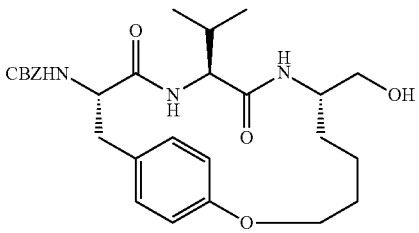

Methyl ester 48 (47 mg) was dissolved in anhydrous THF (40 mL) under an atmosphere of argon. The resultant solution was cooled in ice and 1M LiAlH$_4$ in diethyl ether was added (87 μL). The reaction mixture was stirred in ice for 1 h and then at rt for 18 h. MeOH (10 mL) was added and the reaction mixture was stirred at rt for a further 10 mins before being concentrated in vacuo. The residue was partitioned between EtOAc and 1M aqueous KHSO$_4$. The aqueous phase was extracted twice more with chloroform and each organic extract was washed with brine before being combined, dried (MgSO$_4$), filtered and concentrated in vacuo to yield an off-white solid, 40 mg, 90%.

(7S,10S,13S)-7-Formyl-10-isobutyl-9,12-dioxo-2-oxa-8,11-diaza-bicyclo[13.2.2]nonadeca-1(18),15(19),16-trien-13-yl)-carbamic acid benzyl ester (50)

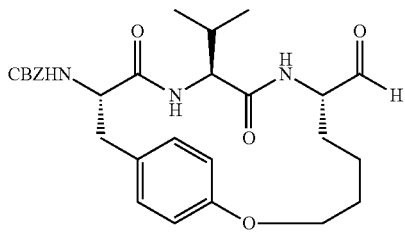

Alcohol 49 (35 mg) was dissolved in DMSO (6, mL) under an atmosphere of argon. To the resultant solution DCM (3 mL) and DIPEA (0.55 ml) were added. The reaction mixture was cooled in ice and sulfur trioxide-pyridine complex (0.5 g) pre-dissolved in DMSO (15 mL) was added. This was stirred in ice for 2 h before being partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/2 EtOAc/(50/70) petroleum ether to EtOAc to yield a light brown solid, 28 mg, 81%. R$_f$=0.61 (2/1 EtOAc/(50/70) petroleum ether).

Scheme 10

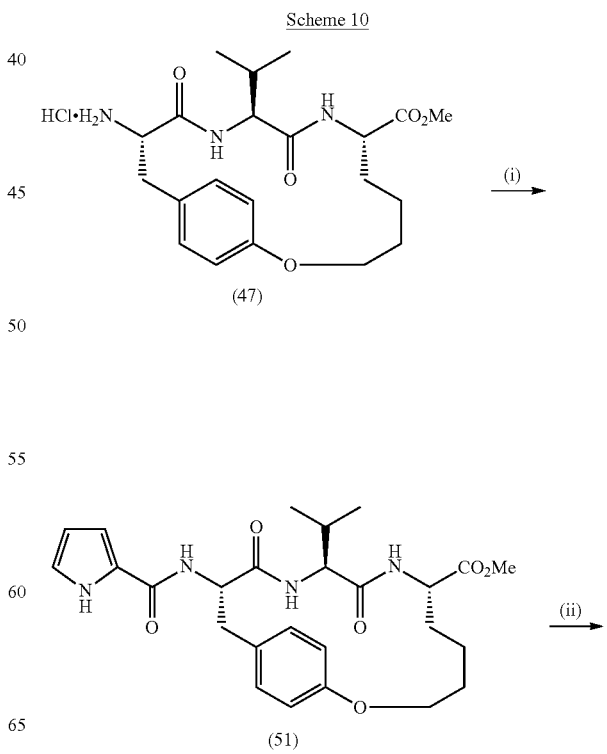

-continued

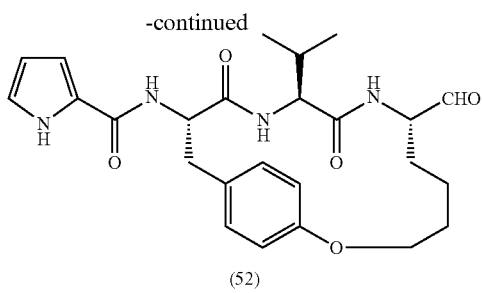

(52)

Reagents and Conditions: (i) 1H-pyrrole-carboxylic acid, DIPEA, DMF, (55%); (ii) DIBAL, DCM, (33%).

(7S,10S,13S)-10-Isopropyl-9,12-dioxo-13-[(1H-pyrrole-2-carbonyl)-amino]-2-oxa-8,11-diaza-bicyclo[13.2.2]nonadeca-1(18),15(19),16-triene-7-carboxylic acid methyl ester (51)

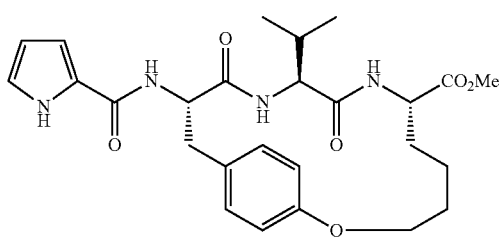 [SMILES: COC(=O)[C@@H]1CCCCOc2ccc(cc2)C[C@H](NC(=O)c2ccc[nH]2)C(=O)N[C@@H](C(C)C)C(=O)N1]

Amine 47 (0.37 g) was dissolved in anhydrous DMF (5 mL). 1H-pyrrole-carboxylic acid (0.11 g), DIPEA (0.72 mL), EDC (0.25 g) and HOBt (0.2 g) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 20% EtOAc/(50/70) petroleum ether to EtOAc to yield an off-white solid, 279 mg, 55%. R$_f$=0.15 (20% EtOAc/(50/70) petroleum ether).

1H-Pyrrole-2-carboxylic acid ((7S,10S,13S)-7-formyl-10-isopropyl-9,12-dioxo-2-oxa-8,11-diaza-bicyclo[13.2.2]nonadeca-1(18),15(19),16-trien-13-yl)-amide (52)

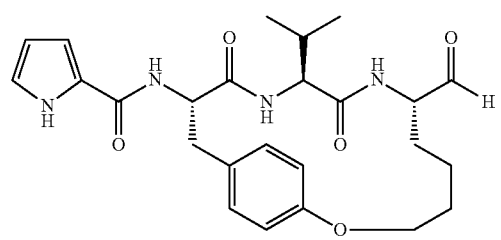 [SMILES: CC(C)[C@@H]1NC(=O)[C@@H](NC(=O)c2ccc[nH]2)Cc2ccc(cc2)OCCCC[C@@H](C=O)NC1=O]

Ester 51 (45 mg) was dissolved in DCM (6 mL) under an atmosphere of argon. The reaction was cooled to −78° C. To the resultant solution DIBAL (0.5 mL) was added dropwise. This was stirred for 2 h before being allowed to warm to rt overnight. The reaction mixture was partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 14 mg, 33%. R$_f$=0.25 (1/1 EtOAc/(50/70) petroleum ether).

Scheme 11

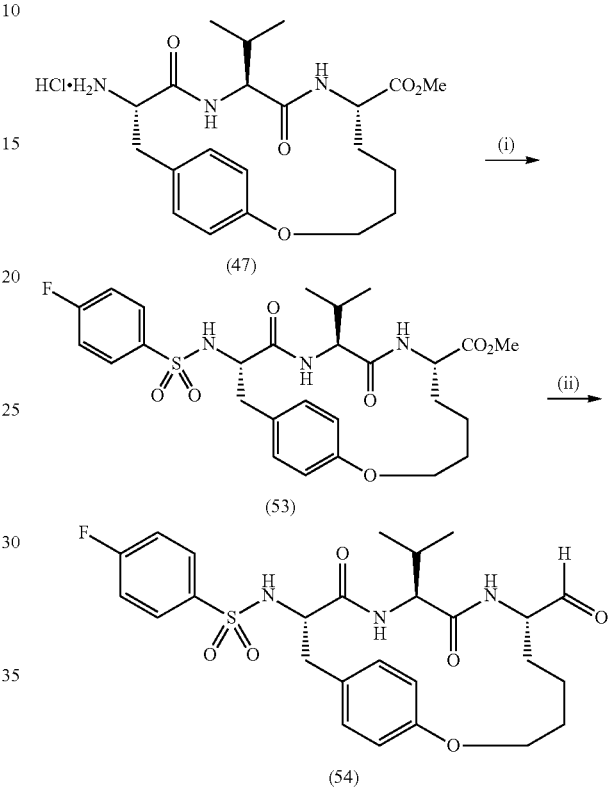

Reagents and Conditions: (i) 4F-benzene-sulfonyl chloride, DIPEA, DMF, (36%); (ii) DIBAL, DCM, (17%).

(7S,10S,13S)-13-(4-Fluoro-benzenesulfonylamino)-10-isopropyl-9,12-dioxo-2-oxa-8,1'-diaza-bicyclo[13.2.2]nonadeca-1(18),15(19),16-triene-7-carboxylic acid methyl ester (53)

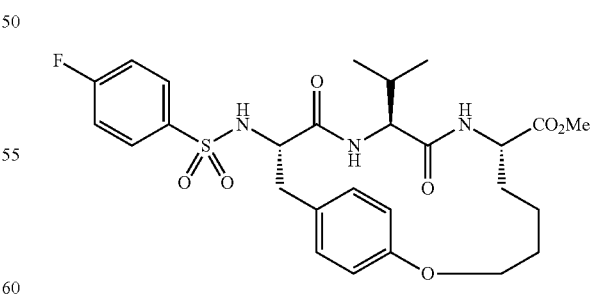

Amine 47 (200 mg) was dissolved in anhydrous DMF (5 mL). 4F-benzene-sulfonyl chloride (96 mg) and DIPEA (0.175 mL) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 109 mg, 39%. R$_f$=0.15 (1/1 EtOAc/(50/70) petroleum ether).

4-Fluoro-N-((7S,10S,13S)-7-formyl-10-isopropyl-9,12-dioxo-2-oxa-8,11-diaza-bicyclo[13.2.2]nonadeca-1(18),15(19),16-trien-13-yl)-benzenesulfonamide (54)

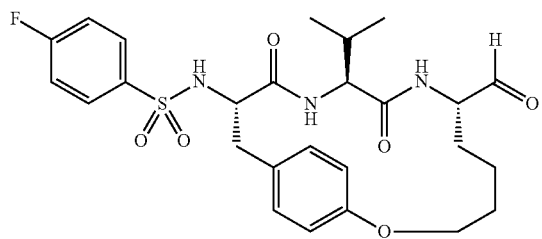 [SMILES: CC(C)[C@@H]1NC(=O)[C@@H](NS(=O)(=O)c2ccc(F)cc2)Cc2ccc(cc2)OCCCC[C@@H](C=O)NC1=O]

Ester 53 (100 mg) was dissolved in DCM (6 mL) under an atmosphere of argon. The reaction was cooled to −78° C. To the resultant solution DIBAL (0.98 mL) was added dropwise. This was stirred for 2 h before being allowed to warm to rt overnight. The reaction mixture was partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 16 mg, 17%. R$_f$=0.35 (1/1 EtOAc/(50/70) petroleum ether).

Scheme 12

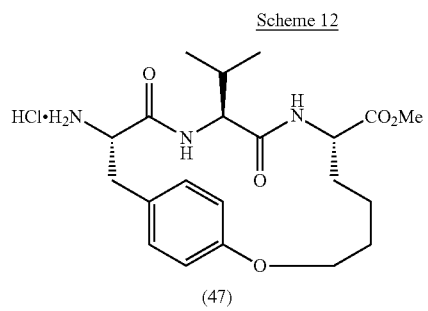

(47)

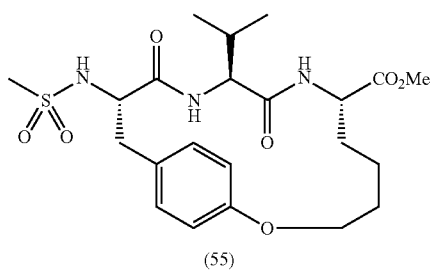

(55)

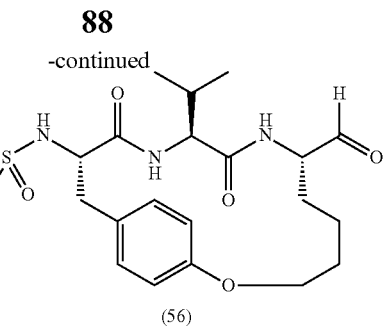

(56)

Reagents and Conditions: (i) methane-sulfonyl chloride, DIPEA, DMF, (17%); (ii) DIBAL, DCM, (19%).

(7S,10S,13S)-10-Isopropyl-13-methanesulfony-lamino-9,12-dioxo-2-oxa-8,11-diaza-bicyclo[13.2.2]nonadeca-1(18),15(19),16-triene-7-carboxylic acid methyl ester (55)

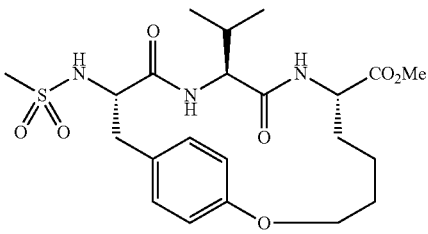 [SMILES: COC(=O)[C@@H]1CCCCOc2ccc(cc2)C[C@H](NS(C)(=O)=O)C(=O)N[C@@H](C(C)C)C(=O)N1]

Amine 47 (200 mg) was dissolved in anhydrous DMF (5 mL). Methane-sulfonyl chloride (39 μL) and DIPEA (0.175 mL) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 40 mg, 17%. R$_f$=0.12 (1/1 EtOAc/(50/70) petroleum ether).

N-((7S,10S,13S)-7-Formyl-10-isopropyl-9,12-dioxo-2-oxa-8,11-diaza-bicyclo[13.2.2]nonadeca-1(18),15(19),16-trien-13-yl)-methanesulfonamide (56)

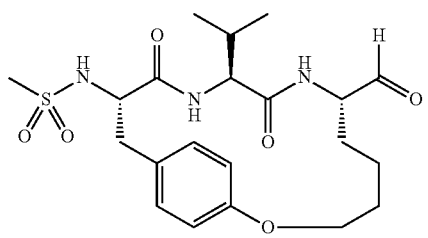 [SMILES: CC(C)[C@@H]1NC(=O)[C@@H](NS(C)(=O)=O)Cc2ccc(cc2)OCCCC[C@@H](C=O)NC1=O]

Ester 55 (40 mg) was dissolved in DCM (6 mL) under an atmosphere of argon. The reaction was cooled to −78° C. To the resultant solution DIBAL (0.46 mL) was added dropwise. This was stirred for 2 h before being allowed to warm to rt overnight. The reaction mixture was partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 7 mg, 19%. R$_f$=0.25 (1/1 EtOAc/(50/70) petroleum ether).

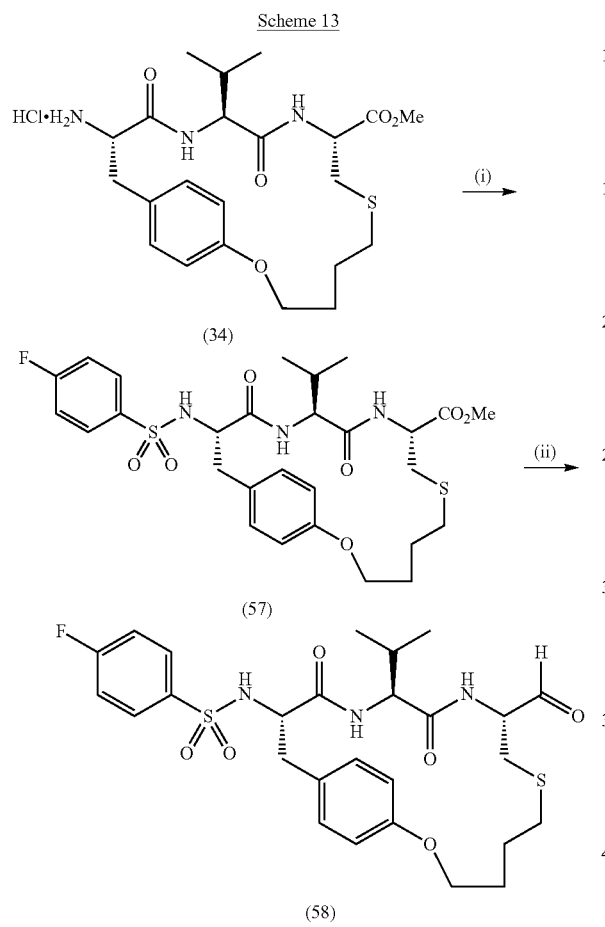

Reagents and Conditions: (i) 4F-benzene-sulfonyl chloride, DIPEA, DMF, (18%); (ii) DIBAL, DCM, (9%).

(9R,12S,15S)-15-(4-Fluoro-benzenesulfonylamino)-12-isopropyl-11,14-dioxo-2-oxa-7-thia-10,13-diaza-bicyclo[15.2.2]henicosa-1(20),17(21),18-triene-9-carboxylic acid methyl ester (57)

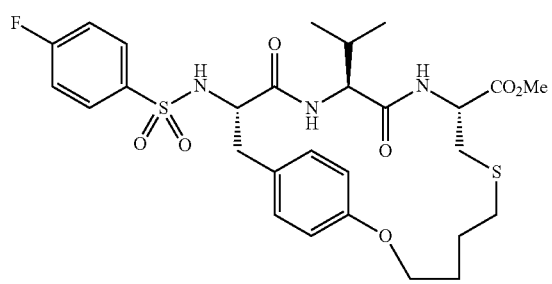 [SMILES: COC(=O)[C@@H]1CSCCCCOc2ccc(cc2)C[C@H](NS(=O)(=O)c2ccc(F)cc2)C(=O)N[C@@H](C(C)C)C(=O)N1]

Amine 34 (208 mg) was dissolved in anhydrous DMF (5 mL). 4F-benzene-sulfonyl chloride (75 mg) and DIPEA (0.16 mL) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 50 mg, 18%. R$_f$=0.2 (1/1 EtOAc/(50/70) petroleum ether).

4-Fluoro-N-((9R,12S,15S)-9-formyl-12-isopropyl-11,14-dioxo-2-oxa-7-thia-10,13-diaza-bicyclo[15.2.2]henicosa-1(20),17(21),18-trien-15-yl)-benzenesulfonamide (58)

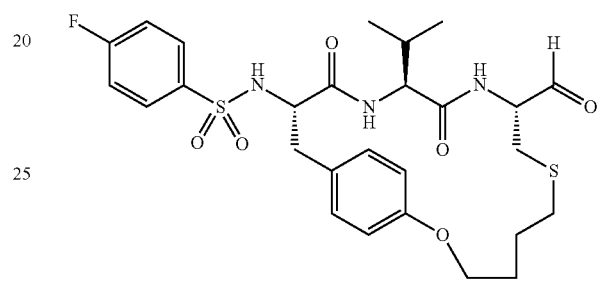

Ester 57 (47 mg) was dissolved in DCM (6 mL) under an atmosphere of argon. The reaction was cooled to −78° C. To the resultant solution DIBAL (0.42°mL) was added dropwise. This was stirred for 2 h before being allowed to warm to rt overnight. The reaction mixture was partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 9 mg, 20%. R$_f$=0.45 (1/1 EtOAc/(50/70) petroleum ether).

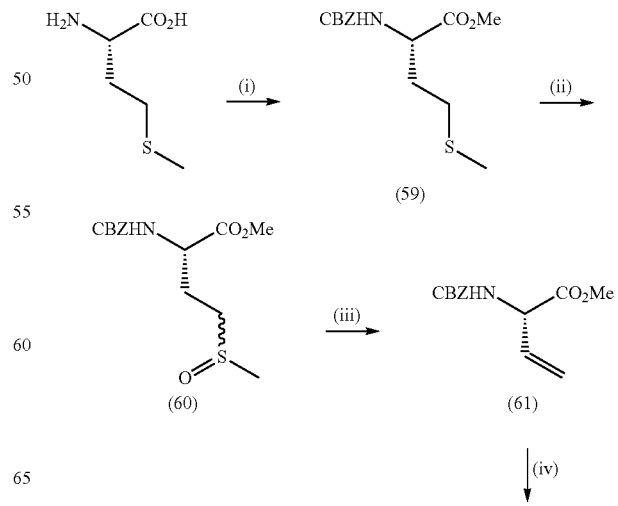

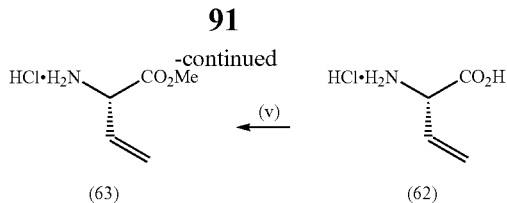

Reagents and Conditions: (i) benzyl chloroformate, NaHCO₃, EtOAc, H₂O, (98%); (ii) NaIO₄, H₂O, MeOH, (100%); (iii) thermal elimination (kugelrohr), (20%); (iv) 6M HCl$_{(aq)}$, (71%); (v) SOCl₂, MeOH, (100%).

(S)-2-Benzyloxycarbonylamino-4-methylsulfanyl-butyric acid methyl ester (59)

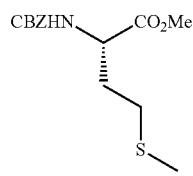

L-methionine (3.70 g, 18.5 mmol) was dissolved in a biphasic mixture of EtOAc (75 mL) and water (75 mL). This was cooled in ice and sodium hydrogen bicarbonate (7.78 g, 5 equiv) and benzyl chloroformate (2.98 mL, 1.1 equiv) were added. This was stirred in ice for one h and then at rt for a further eighteen h before the mixture was allowed to partition. The organic phase was washed sequentially with 1M hydrochloric acid, saturated aqueous sodium hydrogen bicarbonate and brine before being dried (MgSO₄), filtered and concentrated in vacuo to afford a yellow oil, 5.40 g, 98%.

¹H-NMR (500 MHz in CDCl₃) 7.29 (5H, m, Ar—H), 5.79 (1H, d J=7.9 Hz, NH), 5.08 (2H, s, CH₂Ph), 4.43-4.47 (1H, m, CHCO₂CH₃), 3.70 (3H, s, CHCO₂CH₃), 2.49 (2H, dd J=7.4 Hz, J=7.4 Hz, CHCH₂CH₂S), 2.11 (1H, ddd J=7.2 Hz, J=12.8 Hz, J=14.4 Hz, CHCH₂CH₂S), 2.04 (3H, s, SCH₃), 1.93 (1H, ddd J=7.1 Hz, J=7.1 Hz, J=14.4 Hz, CHCH₂CH₂S).

LRMS (ES) 298.1 (MH⁺). C₁₄H₁₉NO₄S requires 298.1.

(S)-2-Benzyloxycarbonylamino-4-methanesulfinyl-butyric acid methyl ester (60)

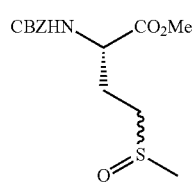

Sulfide 59 (5.40 g, 18.2 mmol) was dissolved in methanol (60 mL). This was cooled in ice and a solution of sodium metaperiodate (4.08 g, 1.05 equiv) in water (25 mL) was added dropwise over 10 mins. This was stirred in ice for 1 h and then at rt for a further 2 h. The resultant white precipitate was removed by filtration under vacuum, the residue washed with methanol and the filtrate concentrated in vacuo. The resultant colourless oil was partitioned between DCM and water. The aqueous phase was extracted twice more with DCM, methanol added to the combined organic extracts to obtain an homogenous solution and this was dried (MgSO₄), filtered and concentrated in vacuo to afford a yellow oil, 5.69 g, 100%. This was obtained as a 1:1 mixture of diastereoisomers.

¹H-NMR (500 MHz in CDCl₃) 7.30-7.35 (5H, m, Ar—H), 6.00-6.08 (1H, m, NH), 5.10 (2H, s, CH₂Ph), 4.44-4.50 (1H, m, CHCO₂CH₃), 3.75 (3H, s, CHCO₂CH₃), 2.67-2.77 (2H, m, CHCH₂CH₂S), 2.53-2.54 (3H, m, SCH₃), 2.32-2.40 (1H, m, CHCH₂CH₂S), 2.09-2.19 (1H, m, CHCH₂CH₂S).

¹³C-NMR (75 MHz in CDCl₃) 172.6, 156.0, 136.2, 128.6, 128.4, 128.3, 128.1, 128.0, 69.9, 53.5, 53.0, 52.4, 31.6, 29.8, 15.3.

LRMS (ES) 314.1 (MH⁺). C₁₄H₁₉NO₅S requires 314.1.

(S)-2-Benzyloxycarbonylamino-but-3-enoic acid methyl ester (61)

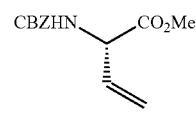

Sulfoxide 60 (5.69 g, 18.2 mmol) was placed in a round bottomed flask in a kugelrohr. This was directly connected to a low vacuum diaphragm pump and heated/distilled at 140° C. The distillate was purified by flash chromatography on silica using a gradient of EtOAc and (50/70) petroleum ether to yield a colourless oil, 0.905 g, 20%. R$_f$=0.24 (1/7 EtOAc/(50/70) petroleum ether).

¹H-NMR (500 MHz in CDCl₃) 7.31-7.35 (5H, m, Ar—H), 5.86-5.93 (1H, m, CHCH₂), 5.61 (1H, d J=6.3 Hz, NH), 5.01-5.39 (2H, m, CHCH₂), 5.11 (2H, s, CH₂Ph), 4.91-4.96 (1H, m, CHCO₂CH₃), 3.74 (3H, s, CHCO₂CH₃).

¹³C-NMR (75 MHz in CDCl₃) 170.9, 155.5, 136.1, 132.2, 128.5, 128.2, 128.1, 127.5, 126.9, 117.7, 67.1, 56.1, 52.7.

LRMS (ES) 250.1 (MH⁺). C₁₃H₁₆NO₄ requires 250.1.

(S)-2-Benzyloxycarbonylamino-but-3-enoic acid methyl ester (62)

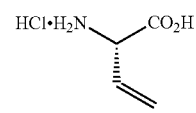

Olefin 61 (0.905 g, 3.61 mmol) was suspended in 6M hydrochloric acid (20 mL). This was heated at reflux for 2 h, cooled and partitioned with DCM. The aqueous phase was washed again with DCM before being concentrated in vacuo to afford a white solid. This was recrystallised from acetone to afford a white solid, 0.350 g, 71%.

$^1$H-NMR (500 MHz in (CD$_3$)$_2$SO) 8.32 (2H, bs, NH$_2$), 6.02-6.11 (1H, m, CHCH$_2$), 5.50-5.75 (2H, m, CHCH$_2$), 4.68-4.73 (1H, m, CHCO$_2$H).

(S)-2-Amino-but-3-enoic acid methyl ester hydrochloride (63)

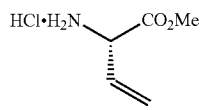

Carboxylic acid 62 (0.350 g, 2.56 mmol) was suspended in methanol (10 mL). This was cooled in ice and 20% (v/v) thionyl chloride was added portionwise. The solution was stirred in ice for 1 h and then at rt for 18 h before being concentrated in vacuo to afford a white solid, 0.388 g, (100%).

$^1$H-NMR (500 MHz in CDCl$_3$) 8.70 (2H, bs, NH$_2$), 6.06-6.13 (1H, m, CHCH$_2$), 5.52-5.73 (2H, m, CHCH$_2$), 4.79-4.82 (1H, m, CHCO$_2$CH$_3$), 3.83 (3H, s, CHCO$_2$CH$_3$).

(S)-2-((S)-2-{(S)-3-(4-Allyloxy-phenyl)-2-[(tert-butoxy-hydroxy-methyl)-amino]-propionylamino}-3-methyl-butyrylamino)-but-3-enoic acid methyl ester (64)

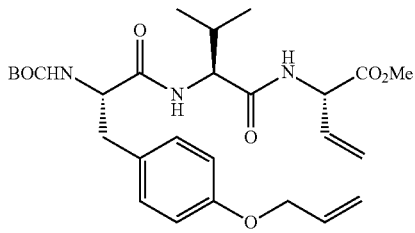

Acid 43 (1.03 g, 2.45 mmol), amine 63 (1.1 equiv) and HATU (1.1 equiv) were dissolved in anhydrous DMF (0.10-0.50M relative to acid). DIPEA was added (4 equiv) and the reaction mixture stirred at rt for 18 h. This was partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 0.964 g, 76%. R$_f$=0.46 (1/1 EtOAc/(50/70) petroleum ether). m.p. 104-106° C.

Scheme 15

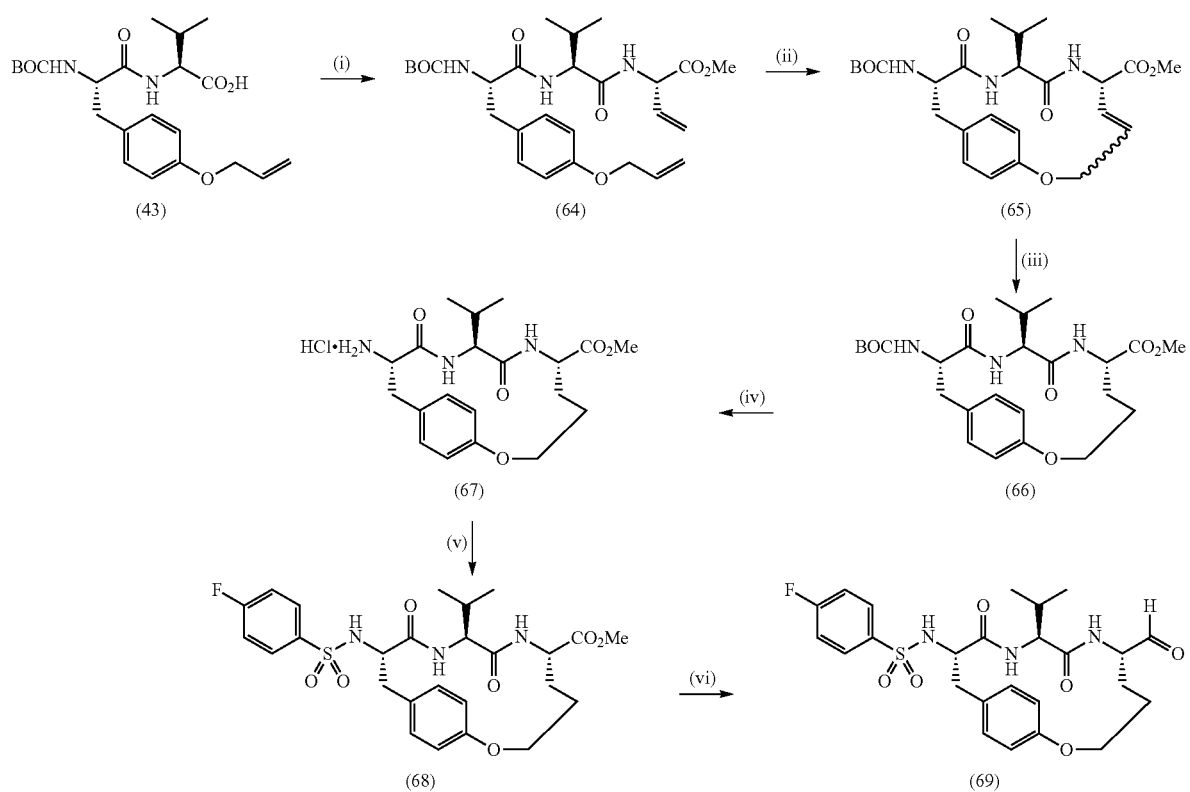

Reagents and Conditions: (i) HATU, DIPEA, (S)-2-amino-but-3-enoic acid methyl ester hydrochloride (63), DMF, (76%); (ii) 3×10 mol % GSGC, 10 mol % chloro-dicyclohexyl borane, 1,1,2-TCE, microwave, (32%); H$_2$, 20 mol % Pd/C, MeOH, EtOAc, (52%); (iv) 4M HCl, 1,4-dioxane, (100%); (v) 4F-benzyl sulfonyl chloride, DIPEA, DMF, (17%); (vi) DIBAL, THF, (40%).

¹H-NMR (500 MHz in CDCl₃) 7.08 (2H, d J=8.2 Hz, Ar—H), 6.82 (2H, d J=8.2 Hz, Ar—H), 6.62 (1H, d J=7.5 Hz, NH), 6.53 (1H, d J=8.5 Hz, NH), 6.42 (1H, d J=8.3 Hz, NH), 6.07 (1H, tdd J=5.3 Hz, J=10.6 Hz, J=17.2 Hz, OCH₂CHCH₂), 5.90-5.97 (1H, m, CHCHCHCH₂), 5.05-5.42 (4H, m, OCH₂CHCH₂ and CHCHCH₂), 4.95-5.00 (1H, m, CHCO₂CH₃), 4.49-4.51 (2H, m, OCH₂CHCH₂), 4.25-4.38 (2H, m, CHCH₂Ph and CHCH(CH₃)₂), 3.74 (3H, s, CHCO₂CH₃), 3.01-3.05 (2H, m, CHCH₂Ph), 2.04-2.11 (1H, m, CHCH(CH₃)₂), 1.45 (9H, s, C(CH₃)₃), 0.89 (3H, d J=7.1 Hz, CHCH(CH₃)₂), 0.87 (3H, d J=7.1 Hz, CHCH(CH₃)₂).

HRMS (ES) 518.2878 (MH⁺). C₂₇H₃₉N₃O₇ requires 518.2866.

Microanalysis: C, 62.37; H, 7.64; N, 8.11. C₂₇H₃₉N₃O₇ requires C, 62.65; H, 7.59; N, 8.12.

(E/Z)-(6S,9S,12S)-12-tert-Butoxycarbonylamino-9-isopropyl-8,11-dioxo-2-oxa-7,10-diazabicyclo[12.2.2]octadeca-1(17),4,14(18),15-tetraene-6-carboxylic acid methyl ester (65)

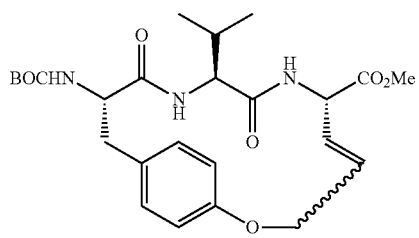

The diene 64 (0.830 g, 1.60 mmol) was dissolved in anhydrous 1,1,2-trichloroethane (0.01M) under an atmosphere of argon. GSGC (0.10 equiv) was added. The mixture was heated at reflux in the microwave (1200 W) for 20 min. Two further additions of GSGC (0.10 equiv) were added and after each the reaction mixture was subjected to a further 20 min heating in the microwave. This was then cooled and concentrated in vacuo. The crude material was purified by flash chromatography on silica using a gradient of EtOAc and (50/70) petroleum ether to yield a brown solid, 0.251 g, 32%. A 1:3.8 ratio of geometric isomers was obtained. R_f=0.32 and 0.35 (2/1 EtOAc/(50/70) petroleum ether).

¹H-NMR for major isomer from mixture (500 MHz in CDCl₃) 6.95 (2H, d J=8.1 Hz, Ar—H), 6.78 (2H, d J=8.1 Hz, Ar—H), 5.84 (1H, d J=8.0 Hz, NH Tyr), 5.38-5.47 (2H, m, OCH₂CHCH and OCH₂CHCHCH), 4.91-4.94 (1H, m, CHCO₂CH₃), 4.61-4.73 (2H, m, OCH₂CHCHCH), 4.04-4.13 (2H, m, CHCH₂Ph and CHCH(CH₃)₂), 3.78 (3H, s, CHCO₂CH₃), 3.03 (1H, dd J=5.1 Hz, J=12.5 Hz, CHCH₂Ph), 2.68 (1H, dd J=12.5 Hz, J=12.5 Hz, CHCH₂Ph), 1.92-1.97 (1H, m, CHCH(CH₃)₂), 1.45 (9H, s, C(CH₃)₃), 0.81-0.85 (6H, m, CHCH(CH₃)₂).

Selected ¹H-NMR for minor isomer from mixture: 7.19 (2H, d J=8.3 Hz, Ar—H), 4.22-4.30 (2H, m, CHCH₂Ph and CHCH(CH₃)₂), 3.74 (3H, s, CHCO₂CH₃)

HRMS (ES) 490.2546 (MH⁺). C₂₅H₃₅N₃O₇ requires 490.2553.

(6S,9S,12S)-12-tert-Butoxycarbonylamino-9-isopropyl-8,11-dioxo-2-oxa-7,10-diaza-bicyclo-[12.2.2]octadeca-1(17),14(18),15-triene-6-carboxylic acid methyl ester (66)

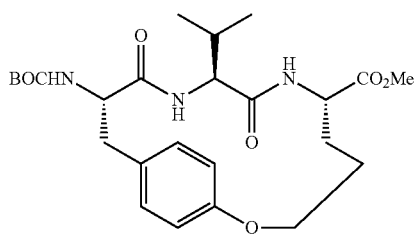

The olefin 65 (0.251 g, 0.513 mmol) was dissolved in methanol and 20% (w/w) of 10% palladium on carbon catalyst was added. The mixture was subjected to hydrogenation at rt and atmospheric pressure for 18 h. The mixture was filtered through celite and concentrated in vacuo to afford a brown solid, 0.131 g, 52%.

¹H-NMR (500 MHz in CDCl₃) 6.96 (2H, d J=8.2 Hz, Ar—H), 6.71 (2H, d J=8.2 Hz, Ar—H), 6.15 (1H, d J=7.1 Hz, NH Val), 5.93 (1H, d J=8.2 Hz, NH Gly), 5.28 (1H, d J=8.6 Hz, NH Tyr), 4.53-4.55 (1H, m, CHCO₂CH₃), 4.23-4.31 (1H, m, OCH₂CH₂CH₂CH) 4.05-4.22 (2H, m, CHCH₂Ph and OCH₂CH₂CH₂CH), 3.82-3.84 (1H, m, CHCH(CH₃)₂), 3.76 (3H, s, CHCO₂CH₃), 3.12 (1H, dd J=5.2 Hz, J=12.5 Hz, CHCH₂Ph), 2.62 (1H, dd J=12.5 Hz, J=12.5 Hz, CHCH₂Ph), 2.02-2.08 (1H, m, CHCH(CH₃)₂), 1.86-1.92 (1H, m, OCH₂CH₂CH₂CH), 1.80 (1H, m, OCH₂CH₂CH₂CH), 1.49-1.57 (2H, m, OCH₂CH₂CH₂CH and OCH₂CH₂CH₂CH), 1.47 (9H, s, C(CH₃)₃), 0.89 (3H, d J=6.8 Hz, CHCH(CH₃)₂), 0.86 (3H, d J=6.8 Hz, CHCH(CH₃)₂).

HRMS (ES) 492.2700 (MH⁺). C₂₅H₃₇N₃O₇ requires 492.2710.

(6S,9S,12S)-12-Amino-9-isopropyl-8,11-dioxo-2-oxa-7,10-diaza-bicyclo[12.2.2]octadeca-1(17),14(18),15-triene-6-carboxylic acid methyl ester hydrogen chloride salt (67)

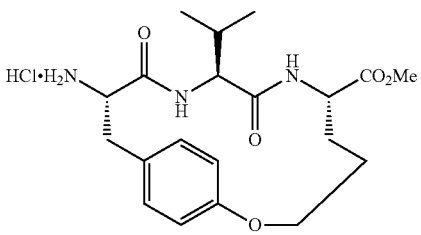

Methyl ester 66 (0.2 g) was dissolved in 4M HCl in 1,4-dioxane (10 mL). The solution was stirred at rt for 16 h before being concentrated in vacuo to yield a brown solid, 0.17 g, 100%.

(6S,9S,12S)-12-(4-Fluoro-benzenesulfonylamino)-9-isopropyl-8,11-dioxo-2-oxa-7,10-diaza-bicyclo[12.2.2]octadeca-1(17),14(18),15-triene-6-carboxylic acid methyl ester (68)

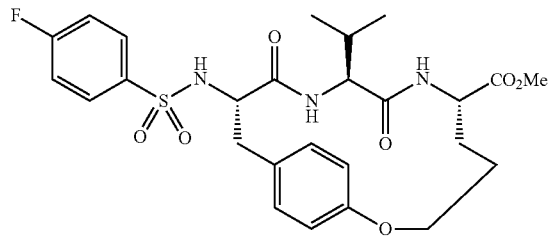 [SMILES: COC(=O)[C@@H]1CCCOc2ccc(cc2)C[C@H](NS(=O)(=O)c2ccc(F)cc2)C(=O)N[C@@H](C(C)C)C(=O)N1]

Amine 67 (170 mg) was dissolved in anhydrous DMF (5 mL). 4F-benzene-sulfonyl chloride (85 mg) and DIPEA (0.15 mL) were added and the reaction mixture was stirred at rt for 18 h before being partitioned between chloroform and 1M hydrochloric acid. The aqueous phase was extracted three more times with chloroform and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 40 mg, 17%. R$_f$=0.2 (1/1 EtOAc/(50/70) petroleum ether).

4-Fluoro-N-((6S,9S,12S)-6-formyl-9-isopropyl-8,11-dioxo-2-oxa-7,10-diaza-bicyclo[12.2.2]octadeca-1(17),14(18),15-trien-12-yl)-benzenesulfonamide (69)

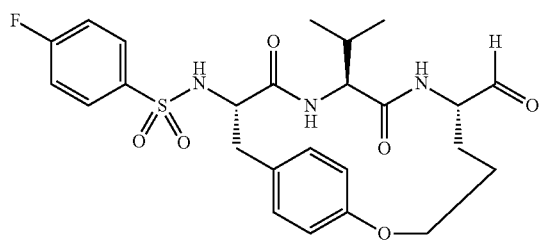 [SMILES: CC(C)[C@@H]1NC(=O)[C@@H](NS(=O)(=O)c2ccc(F)cc2)Cc2ccc(cc2)OCCC[C@@H](C=O)NC1=O]

Ester 68 (39 mg) was dissolved in DCM (6 mL) under an atmosphere of argon. The reaction was cooled to −78° C. To the resultant solution DIBAL (0.39 mL) was added dropwise. This was stirred for 2 h before being allowed to warm to rt overnight. The reaction mixture was partitioned between EtOAc and 1M hydrochloric acid. The aqueous phase was extracted again with EtOAc and the combined organic extracts were dried (MgSO$_4$), filtered and concentrated in vacuo. Purification was achieved using flash chromatography, eluting with a gradient of 1/1 EtOAc/(50/70) petroleum ether to EtOAc to yield a light brown solid, 15 mg, 40%. R$_f$=0.25 (1/1 EtOAc/(50/70) petroleum ether).

Scheme 16

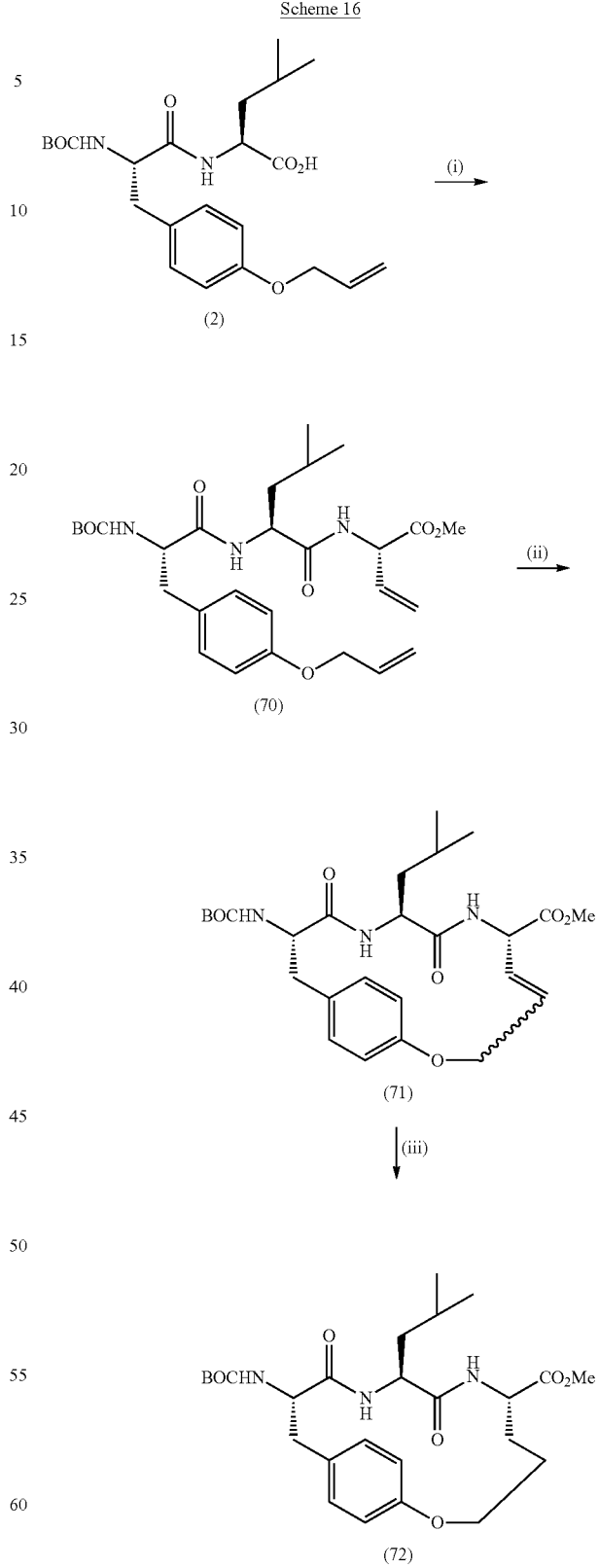

Reagents and Conditions: (i) HATU, DIPEA, (S)-2-amino-but-3-enoic acid methyl ester hydrochloride (63), DMF, (83%); (ii) 3×10 mol % GSGC, 10 mol % chloro-dicyclohexyl borane, 1,1,2-TCE, microwave, (48%); (iii) H₂, 20 mol % Pd/C, MeOH, EtOAc, (53%).

2S-{2S-[3S-(4-Allyloxyphenyl)-2-tert-butoxycarbo-nylaminopropionylamino]-4-methylpentanoy-lamino}-but-3-enoic acid methyl ester (70)

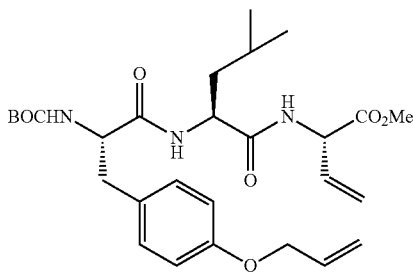

Acid 2 (5.11 g, 11.8 mmol), amine 63 (1.1 equiv) and HATU (1.1 equiv) were dissolved in anhydrous DMF (0.10-0.50M relative to acid). DIPEA was added (4 equiv) and the reaction mixture stirred at rt for 18 h. This was partitioned between EtOAc and 1M hydrochloric acid. The organic phase was washed sequentially with 1M hydrochloric acid and brine before being dried (MgSO₄), filtered and concentrated in vacuo. The crude material was purified by flash chromatography on silica using a gradient of EtOAc and (50/70) petroleum ether to yield a white solid, 5.18 g, 83%. $R_f$=0.5 (1/1 EtOAc/(50/70) petroleum ether). m.p. 102-104° C.

¹H-NMR (500 MHz in CDCl₃) 7.08 (2H, d J=8.4 Hz, o-Tyr), 6.96 (1H, d J=6.3 Hz, vinylGly NH), 6.81 (2H, d J=8.5 Hz, m-Tyr), 6.49 (2H, d J=7.0 Hz, Leu NH), 6.03 (1H, ddd J=5.3, J=10.5, J=22.4 Hz, allyl CH), 5.88 (1H, ddd J=5.5, J=10.3, J=17.0 Hz, vinyl CH), 5.42-5.22 (4H, m, allyl CH₂ and vinyl CH₂), 5.11-5.02 (2H, m, vinylGly α-H, Tyr NH), 4.61-4.40 (3H, m, Leu α-H and OCH₂CHCH₂), 4.32 (1H, m, Tyr α-H), 3.76 (3H, s, OCH₃), 2.97 (2H, m, Tyr CH₂), 1.66 (1H, m, Leu CH₂), 1.57 (1H, m, Leu CH), 1.48 (1H, m, Leu CH₂), 1.39 (9H, s C(CH₃)₃), 0.90 (6H, dd J=4.5, J=6.2 Hz, Leu CH₃).

¹³C NMR (75 MHz in CDCl₃) 171.7, 171.4, 170.5, 157.5, 155.7, 133.2, 131.6, 130.2, 128.6, 117.9, 117.5, 114.7, 80.0, 68.8, 55.7, 55.6, 54.4, 52.6, 51.6, 40.9, 37.1, 28.2, 24.5, 22.7, 22.1.

HRMS (ES) 532.3027 (MH⁺). $C_{28}H_{42}N_3O_7$ requires 532.3023.

(E/Z)-12S-tert-Butoxycarbonylamino-9S-isobutyl-8,11-dioxo-2-oxa-7,10-diazabicyclo[12.2.2]octadeca-1(17),4,14(18),15-tetraene-6S-carboxylic acid methyl ester (71)

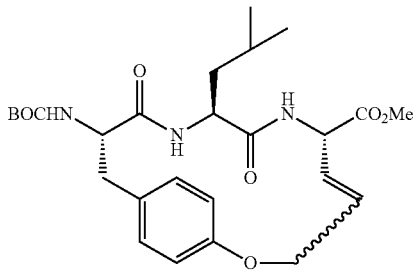

The diene 70 (1.06 g, 2.0 mmol) was dissolved in anhydrous 1,1,2-trichloroethane (0.01M) under an atmosphere of argon. GSGC (0.10 equiv) was added. The mixture was heated at reflux in the microwave (1200 W) for 20 mins. Two further additions of GSGC (0.10 equiv) were added and after each the reaction mixture was subjected to a further 20 mins heating in the microwave. This was then cooled and concentrated in vacuo. The crude material was purified by flash chromatography on silica using a gradient of EtOAc and (50/70) petroleum ether to yield a white solid, 488 mg, 48%. m.p. 237-241° C. A >19:1 ratio of geometric isomers was obtained. $[\alpha]_D$=+1.6 (c 1, CHCl₃)

¹H NMR (500 MHz in CDCl₃) 7.17 (1H, d J=8.2 Hz, Ar—H), 6.87 (2H, dd J=5.3, J=13.9 Hz, Ar—H), 6.72 (1H, d J=7.3 Hz, NH), 6.60 (1H, dd J=2.4, J=8.4 Hz, Ar—H), 5.88 (1H, d J=8.7 Hz, Leu NH), 5.72 (1H, ddd J=4.1, J=7.9, J=15.4 Hz, OCH₂CHCHCH), 5.49 (1H, d J=8.8 Hz, Tyr NH), 5.42 (1H, dd J=8.7, J=15.3 Hz, OCH₂CHCHCH), 4.89 (1H, t J=8.0 Hz, Gly Hα), 4.67 (2H, m, OCH₂CHCHCH), 4.40 (1H, dd J=8.0, J=15.0 Hz, Leu Hα), 4.15 (1H, m, Tyr Hα), 3.78 (3H, s, OCH₃), 3.03 (1H, dd J=4.7, J=12.6 Hz, CHCH₂Ph), 2.69 (1H, t J=12.3 Hz, CHCH₂Ph), 1.57-1.39 (12H, m, CHCH₂CH(CH₃)₂, CHCH₂CH(CH₃)₂, C(CH₃)₃), 0.87 (6H, t J=5.7 Hz, CHCH₂CH(CH₃)₂).

¹³C NMR (75 MHz in CDCl₃) 170.7, 170.1, 155.3, 155.1, 130.8, 130.0, 129.5, 129.4, 128.8, 119.4, 115.9, 79.6, 67.0, 57.3, 53.9, 52.8, 50.9, 42.8, 38.7, 28.3, 24.6, 22.7, 22.6.

HRMS (ES) 504.2727. $C_{26}H_{38}N_3O_7$ requires 504.2710.

12S-tert-Butoxycarbonylamino-9S-isobutyl-8,11-dioxo-2-oxa-7,10-diazabicyclo[12.2.2]octadeca-1(17),14(18),15-triene-6S-carboxylic acid methyl ester (72)

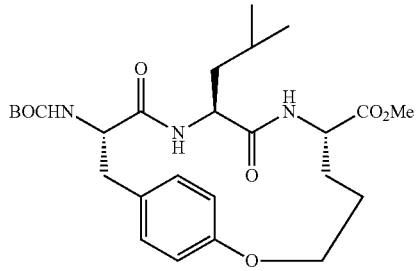

The olefin 71 (450 mg, 0.89 mmol) was dissolved in methanol and 20% (w/w) of 10% palladium on carbon catalyst was added. The mixture was subjected to hydrogenation at rt and atmospheric pressure for 18 h. The mixture was filtered through celite and concentrated in vacuo to afford a brown solid, 241 mg, 53%. m.p. 229-231° C. $[\alpha]_D$=+20.8 (c 1, CHCl₃).

¹H NMR (500 MHz in CDCl₃) 7.20 (1H, d J=7.4 Hz, m-Tyr), 6.95 (1H, dd J=2.2, J=8.3 Hz, o-Tyr), 6.88 (1H, dd J=2.6, J=8.4 Hz, o-Tyr), 6.69 (1H, dd J=2.6, J=8.3 Hz, m-Tyr), 6.11 (1H, d J=6.6 Hz, Gly NH), 5.94 (1H, d J=7.8 Hz, Leu NH), 5.32 (1H, d J=8.6 Hz, Tyr NH), 4.48 (1H, dd J=5.8, J=10.3 Hz, Gly α-H), 4.31 (1H, m, OCH₂CH₂CH₂CH), 4.23-4.03 (3H, m, Tyr α-H, OCH₂CH₂CH₂CH, Leu α-H), 3.76 (3H, s, OCH₃), 3.14 (1H, dd J=5.5, J=12.5 Hz, CHCH₂Ph), 2.62 (1H, t J=12.1 Hz, CHCH₂Ph), 2.15 (1H, m, OCH₂CH₂CH₂CH), 1.92 (1H, m, OCH₂CH₂CH₂CH), 1.68 (1H, m, OCH₂CH₂CH₂CH), 1.53-1.31 (12H, m, CHCH₂CH(CH₃)₂, C(CH₃)₃, CHCH₂CH(CH₃)₂), 1.23 (1H, m, OCH₂CH₂CH₂CH), 0.87 (6H, d J=6.5 Hz, CHCH₂CH(CH₃)₂).

$^{13}$C NMR (75 MHz in CDCl$_3$) 171.8, 170.2, 169.8, 155.7, 154.3, 129.9, 129.2, 128.7, 118.4, 115.0, 79.1, 65.4, 56.6, 52.2, 51.3, 51.1, 43.0, 38.7, 28.0, 26.7, 24.2, 22.4, 22.3, 20.8.

HRMS (ES) 506.2880 (MH$^+$). C$_{26}$H$_{40}$N$_3$O$_7$ requires 506.2866.

hexyl borane, 1,1,2-TCE, microwave, (40%); (iii) H$_2$, 20 mol % Pd/C, MeOH, EtOAc, (100%).

2S-{2S-[3S-(4-Allyloxyphenyl)-2-tert-butoxycarbonylaminopropionylamino]-4-methylpentanoylamino}-3-allylsulfanylpropionic acid methyl ester (73)

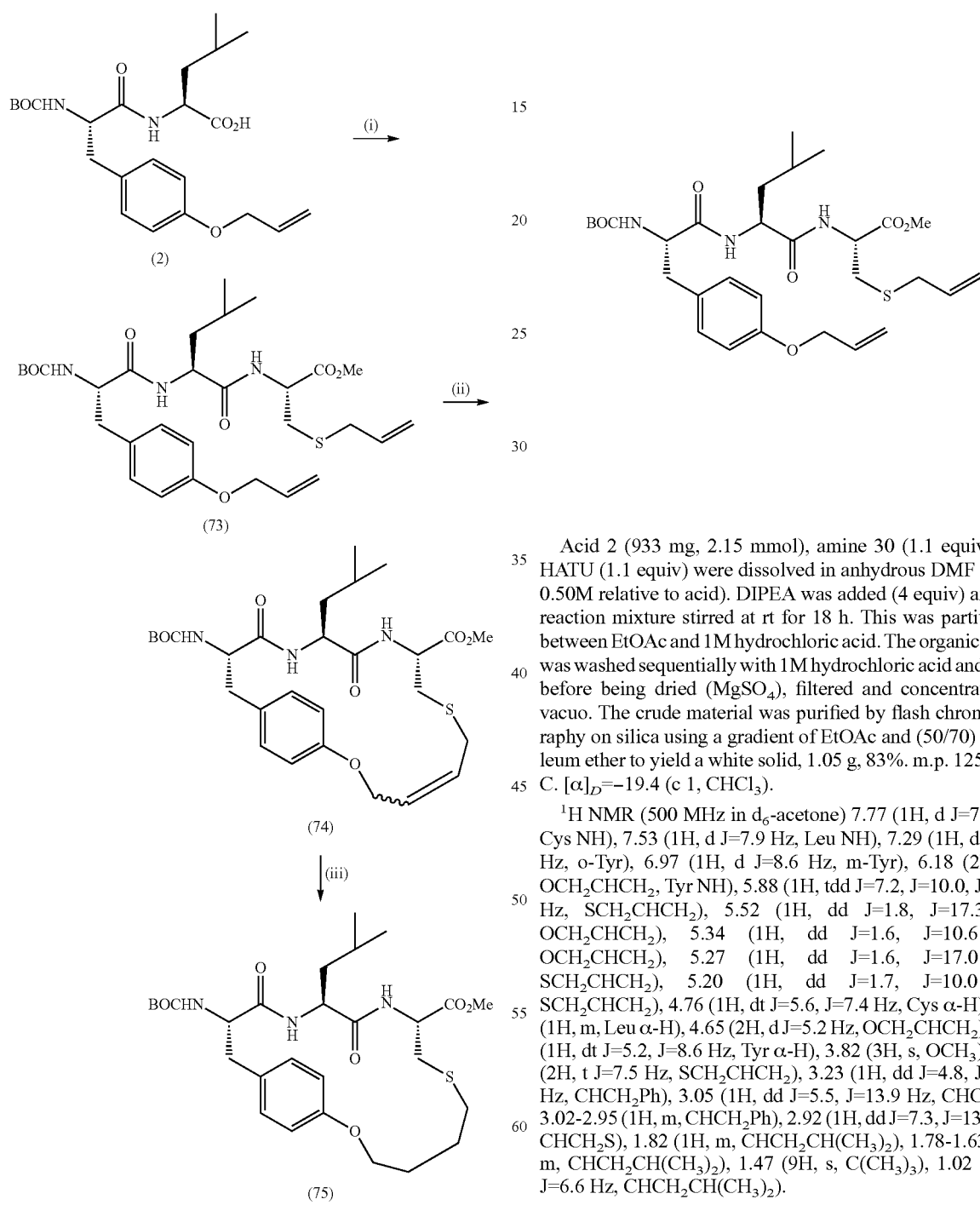

Acid 2 (933 mg, 2.15 mmol), amine 30 (1.1 equiv) and HATU (1.1 equiv) were dissolved in anhydrous DMF (0.10-0.50M relative to acid). DIPEA was added (4 equiv) and the reaction mixture stirred at rt for 18 h. This was partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 1.05 g, 83%. m.p. 125-126° C. [α]$_D$=−19.4 (c 1, CHCl$_3$).

$^1$H NMR (500 MHz in d$_6$-acetone) 7.77 (1H, d J=7.8 Hz, Cys NH), 7.53 (1H, d J=7.9 Hz, Leu NH), 7.29 (1H, d J=8.5 Hz, o-Tyr), 6.97 (1H, d J=8.6 Hz, m-Tyr), 6.18 (2H, m, OCH$_2$CHCH$_2$, Tyr NH), 5.88 (1H, tdd J=7.2, J=10.0, J=17.1 Hz, SCH$_2$CHCH$_2$), 5.52 (1H, dd J=1.8, J=17.3 Hz, OCH$_2$CHCH$_2$), 5.34 (1H, dd J=1.6, J=10.6 Hz, OCH$_2$CHCH$_2$), 5.27 (1H, dd J=1.6, J=17.0 Hz, SCH$_2$CHCH$_2$), 5.20 (1H, dd J=1.7, J=10.0 Hz, SCH$_2$CHCH$_2$), 4.76 (1H, dt J=5.6, J=7.4 Hz, Cys α-H), 4.69 (1H, m, Leu α-H), 4.65 (2H, d J=5.2 Hz, OCH$_2$CHCH$_2$), 4.46 (1H, dt J=5.2, J=8.6 Hz, Tyr α-H), 3.82 (3H, s, OCH$_3$), 3.29 (2H, t J=7.5 Hz, SCH$_2$CHCH$_2$), 3.23 (1H, dd J=4.8, J=13.9 Hz, CHCH$_2$Ph), 3.05 (1H, dd J=5.5, J=13.9 Hz, CHCH$_2$S), 3.02-2.95 (1H, m, CHCH$_2$Ph), 2.92 (1H, dd J=7.3, J=13.9 Hz, CHCH$_2$S), 1.82 (1H, m, CHCH$_2$CH(CH$_3$)$_2$), 1.78-1.63 (2H, m, CHCH$_2$CH(CH$_3$)$_2$), 1.47 (9H, s, C(CH$_3$)$_3$), 1.02 (6H, t J=6.6 Hz, CHCH$_2$CH(CH$_3$)$_2$).

$^{13}$C NMR (75 MHz in d$_6$-acetone) 172.1, 171.6, 171.1, 157.6, 155.6, 134.4, 134.2, 130.6, 130.1, 117.2, 116.5, 114.6, 78.7, 68.5, 56.1, 52.3, 51.9, 51.4, 41.6, 37.1, 34.6, 32.0, 27.9, 24.5, 22.8, 21.5.

Reagents and Conditions: (i) HATU, DIPEA, 30, DMF, (83%); (ii) 3×10 mol % GSGC, 10 mol % chloro-dicyclo- HRMS (ES) 614.2850 (MNa$^+$). C$_{30}$H$_{45}$N$_3$O$_7$SNa requires 614.2876.

(E/Z)-15S-tert-Butoxycarbonylamino-12S-isobutyl-11,14-dioxo-2-oxa-2-thia-10,13-diaza-bicyclo[15.2.2]heneicosa-1(20),4,17(21),18-tetraene-9R-carboxylic acid methyl ester (74)

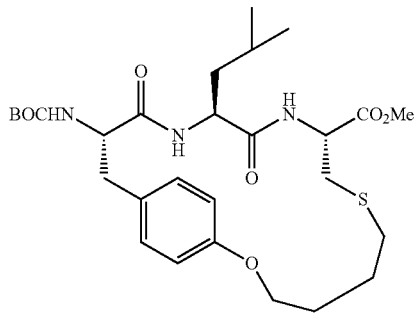

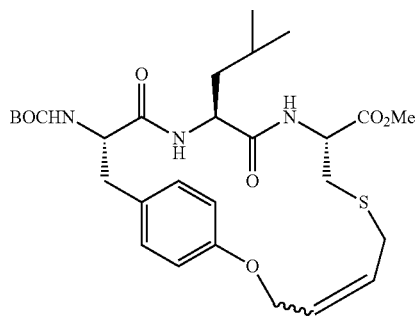

The diene 73 (503 mg, 0.85 mmol) was dissolved in anhydrous 1,1,2-trichloroethane (0.01M) under an atmosphere of argon. GSGC (0.10 equiv) was added. The mixture was heated at reflux in the microwave (1200 W) for 20 mins. Two further additions of GSGC (0.10 equiv) were added and after each the reaction mixture was subjected to a further 20 mins heating in the microwave. This was then cooled and concentrated in vacuo. The crude material was purified by flash chromatography on silica using a gradient of EtOAc and (50/70) petroleum ether to yield a white solid, 197 mg, 40%. m.p. 228-231° C. A >19:1 ratio of geometric isomers was obtained. [α]$_D$=−16.1 (c 1, CHCl$_3$).

$^1$H NMR (500 MHz in CDCl$_3$) 7.10 (2H, d J=8.2 Hz, Ar—H), 6.80 (2H, d J=8.3 Hz, Ar—H), 6.53 (1H, d J=7.8 Hz, Cys NH), 5.90 (1H, d J=7.1 Hz, Leu NH), 5.66 (2H, s, OCH$_2$CHCHCH$_2$S and OCH$_2$CHCHCH$_2$S), 5.37 (1H, d J=7.9 Hz, Tyr NH), 4.72 (1H, d J=14.6 Hz, OCH$_2$CHCHCH$_2$S), 4.60 (2H, m, OCH$_2$CHCHCH$_2$S and Cys α-H), 4.31 (1H, m, Leu α-H), 4.26 (1H, m, Tyr α-H), 3.78 (3H, s OCH$_3$), 3.19 (1H, dd J=5.6, J=15.5 Hz, OCH$_2$CHCHCH$_2$S), 3.07 (1H, d J=12.6 Hz, OCH$_2$CHCHCH$_2$S), 2.94 (2H, m, CHCH$_2$Ph), 2.74-2.50 (2H, m, CHCH$_2$S), 1.53 (2H, m, CHCH$_2$CH(CH$_3$)$_2$ and CHCH$_2$CH(CH$_3$)$_2$), 1.45 (10H, s, C(CH$_3$)$_3$ and CHCH$_2$CH(CH$_3$)$_2$), 0.86 (3H, d J=6.0 Hz, CHCH$_2$CH(CH$_3$)$_2$), 0.84 (d, 3H, J=5.7 Hz, CHCH$_2$CH(CH$_3$)$_2$).

$^{13}$C NMR (75 MHz in CDCl$_3$) 170.8, 170.7, 170.4, 156.4, 154.7, 129.8, 129.4, 128.6, 128.2, 114.7, 79.2, 66.9, 55.3, 51.9, 51.1, 50.9, 40.5, 37.4, 32.4, 30.8, 28.0, 23.9, 22.5, 21.6.

HRMS (ES) 564.2752 (MH$^+$). C$_{28}$H$_{42}$N$_3$O$_7$S requires 564.2743.

15S-tert-Butoxycarbonylamino-12S-isobutyl-11,14-dioxo-2-oxa-2-thia-10,13-diaza-bicyclo[15.2.2]heneicosa-1(20),17(21),18-triene-9R-carboxylic acid methyl ester (75)

The olefin 74 (188 mg, 0.334 mmol) was dissolved in methanol and 20% (w/w) of 10% palladium on carbon catalyst was added. The mixture was subjected to hydrogenation at rt and atmospheric pressure for 18 h. The mixture was filtered through celite and concentrated in vacuo to afford a white solid, 188 mg, 100%. m.p. 210-211° C. [α]$_D$=+29.5 (c 1, CHCl$_3$).

$^1$H NMR (500 MHz in CDCl$_3$) 7.10 (2H, d J=7.8 Hz, o-Tyr), 6.79 (2H, d J=7.9 Hz, m-Tyr), 6.24 (1H, d J=6.6 Hz, Cys NH), 6.06 (1H, d J=7.2 Hz, Leu NH), 5.33 (1H, d J=7.0 Hz, Tyr NH), 4.58 (1H, m, Cys α-H), 4.32-4.13 (3H, m, Leu α-H, Tyr α-H, OCH$_2$CH$_2$CH$_2$CH$_2$S), 4.05 (1H, m, OCH$_2$CH$_2$CH$_2$CH$_2$S), 3.76 (3H, s, OCH$_3$), 3.01 (1H, dd J=3.8, J=12.5 Hz, CHCH$_2$Ph), 2.82 (2H, m, CHCH$_2$Ph, CHCH$_2$S), 2.67 (1H, dd J=3.8, J=11.7 Hz, CHCH$_2$S), 2.56 (2H, m, OCH$_2$CH$_2$CH$_2$CH$_2$S), 1.92-1.65 (4H, m, OCH$_2$CH$_2$CH$_2$CH$_2$S, OCH$_2$CH$_2$CH$_2$CH$_2$S), 1.53 (3H, m, CHCH$_2$CH(CH$_3$)$_2$, CHCH$_2$CH(CH$_3$)$_2$), 1.45 (9H, s, C(CH$_3$)$_3$), 0.86 (6H, dd J=4.7, J=10.4 Hz, CHCH$_2$CH(CH$_3$)$_2$).

$^{13}$C NMR (75 MHz in CDCl$_3$) 171.2, 170.7, 170.4, 157.3, 155.2, 130.1, 128.3, 115.1, 79.9, 66.5, 56.8, 52.7, 52.5, 51.2, 42.5, 38.2, 34.0, 31.6, 28.3, 26.6, 25.6, 24.4, 22.8, 22.4.

HRMS (ES) 566.2903 (MH$^+$). C$_{28}$H$_{44}$N$_3$O$_7$S requires 566.2900.

Scheme 18

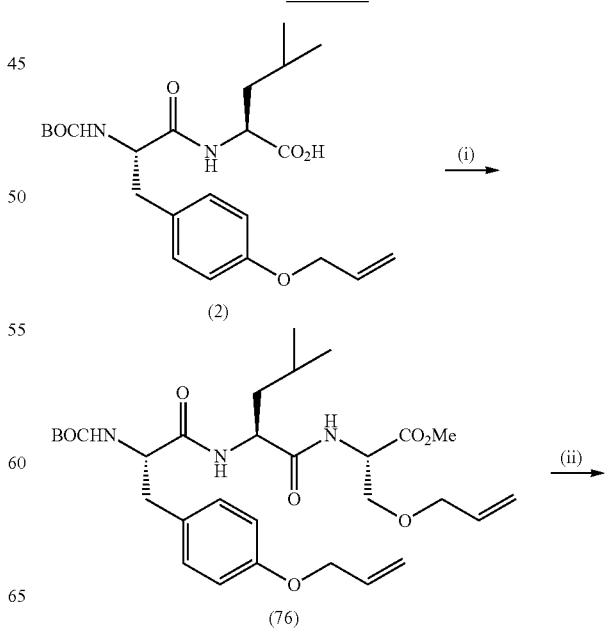

-continued

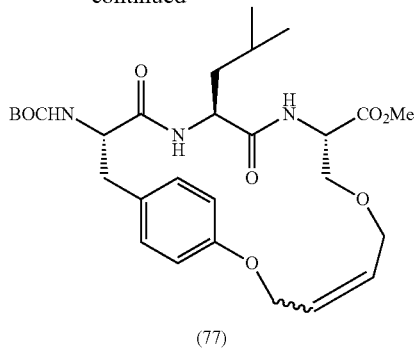

(77)

|(iii)

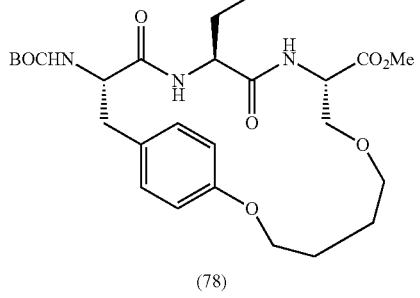

(78)

Reagents and Conditions: (i) HATU, DIPEA, 38, DMF, (77%); (ii) 3×10 mol % GSGC, 10 mol % chloro-dicyclohexyl borane, 1,1,2-TCE, microwave, (33%); H$_2$, 20 mol % Pd/C, MeOH, EtOAc, (75%).

3S-Allyloxy-2-{2S-[3S-(4-allyloxyphenyl)-2-tert-butoxycarbonylaminopropionylamino]-4-methyl-pentanoylamino}propionic acid methyl ester (76)

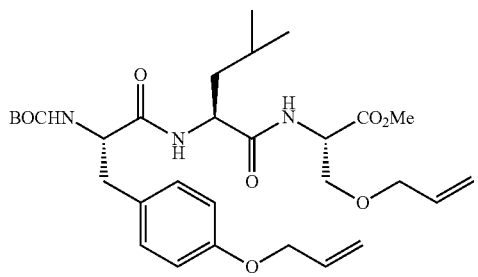

Acid 2 (4.58 g, 10.5 mmol), amine 38 (1.1 equiv) and HATU (1.1 equiv) were dissolved in anhydrous DMF (0.10-0.50M relative to acid). DIPEA was added (4 equiv) and the reaction mixture stirred at rt for 18 h. This was partitioned between EtOAc and 1M hydrochloric acid. The organic phase was washed sequentially with 1M hydrochloric acid and brine before being dried (MgSO$_4$), filtered and concentrated in vacuo. The crude material was purified by flash chromatography on silica using a gradient of EtOAc and (50/70) petroleum ether to yield a white solid, 4.65 g, 77%. m.p. 87-89° C. $[\alpha]_D$=−3.0 (c 1, CHCl$_3$).

$^1$H NMR (500 MHz in CDCl$_3$) 7.10 (2H, d J=8.5 Hz, o-Tyr), 6.83 (2H, d J=8.6 Hz, m-Tyr), 6.68 (1H, d J=7.9 Hz, Ser NH), 6.40 (1H, d J=7.3 Hz, Leu NH), 6.04 (1H, ddd J=5.3, J=10.5, J=22.5 Hz, Tyr OCH$_2$CHCH$_2$), 5.84 (1H, ddd J=5.6, J=10.8, J=16.0 Hz, Ser OCH$_2$CHCH$_2$), 5.39 (1H, dd J=1.6, J=17.3 Hz, Tyr OCH$_2$CHCH$_2$), 5.30-5.16 (3H, m, Tyr OCH$_2$CHCH$_2$, Ser OCH$_2$CHCH$_2$), 4.95 (1H, br s, Tyr NH), 4.67 (1H, m, Ser α-H), 4.50 (2H, d J=5.3 Hz, Tyr OCH$_2$CHCH$_2$), 4.46 (1H, m, Leu α-H), 4.31 (1H, m, Tyr α-H), 3.98 (2H, dq, J=5.6, J=13.0 Hz, Ser OCH$_2$CHCH$_2$), 3.87 (1H, dd J=3.3, J=9.6 Hz, CHCH$_2$Oallyl), 3.75 (3H, s, OCH$_3$), 3.62 (1H, dd J=3.3, J=9.6 Hz, CHCH$_2$Oallyl), 3.00 (2H, d J=6.6 Hz, CHCH$_2$Ar), 1.60 (2H, m, CHCH$_2$CH(CH$_3$)$_2$, CHCH$_2$CH(CH$_3$)$_2$), 1.48 (1H, m, CHCH$_2$CH(CH$_3$)$_2$), 1.40 (9H, s C(CH$_3$)$_3$), 0.91 (6H, dd J=2.8, J=6.2 Hz, CHCH$_2$CH(CH$_3$)$_2$)

$^{13}$C NMR (75 MHz in CDCl$_3$ 171.5, 171.2, 170.3, 157.5, 155.4, 133.9, 133.2, 130.2, 128.6, 117.5, 114.7, 80.1, 72.1, 69.3, 68.7, 55.6, 52.5, 51.5, 41.4, 37.1, 28.2, 24.4, 22.8, 22.0

HRMS (ES) 576.3275 (MH$^+$); C$_{30}$H$_{46}$N$_3$O$_8$ requires 576.3285.

(E/Z)-15S-tert-Butoxycarbonylamino-12S-isobutyl-11,14-dioxo-2,7-dioxa-10,13-diaza-bicyclo[15.2.2]heneicosa-1(20),4,17(21),18-tetraene-9R-carboxylic acid methyl ester (77)

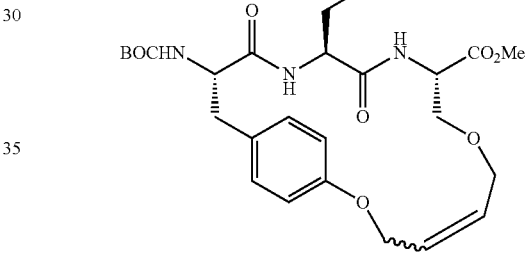

The diene 76 (719 mg, 1.25 mmol) was dissolved in anhydrous 1,1,2-trichloroethane (0.01M) under an atmosphere of argon. GSGC (0.10 equiv) was added. The mixture was heated at reflux in the microwave (1200 W) for 20 min. Two further additions of GSGC (0.10 equiv) were added and after each the reaction mixture was subjected to a further 20 min heating in the microwave. This was then cooled and concentrated in vacuo. The crude material was purified by flash chromatography on silica using a gradient of EtOAc and (50/70) petroleum ether to yield a pale brown solid, 229 mg, 33%. m.p. 209-211° C. A>19:1 ratio of geometric isomers was obtained. $[\alpha]_D$=−0.30 (c 1, CHCl$_3$).

$^1$H NMR (500 MHz in CDCl$_3$) 7.08 (2H, d J=8.4 Hz, Ar—H), 6.76 (2H, d J=8.5 Hz, Ar—H), 6.42 (1H, d J=8.2 Hz, Ser NH), 6.23 (1H, d J=7.9 Hz, Leu NH), 5.72 (1H, td J=3.9, J=3.9, J=16.0 Hz, PhOCH$_2$CHCHCH$_2$O), 5.68-5.60 (1H, td J=6.2, J=6.2, 16.0 Hz PhOCH$_2$CHCHCH$_2$O), 5.36 (1H, d J=8.0 Hz, Tyr NH), 4.72 (1H, m, Ser α-H), 4.64 (2H, s, PhOCH$_2$CHCHCH$_2$O), 4.39-4.26 (2H, m, Leu α-H, Tyr α-H), 4.12 (1H, dd J=5.1, J=12.9 Hz, PhOCH$_2$CHCHCH$_2$O), 3.81 (1H, dd J=7.1, J=12.7 Hz, PhOCH$_2$CHCHCH$_2$O), 3.78 (3H, s, OCH$_3$), 3.53 (1H, dd J=5.3, J=8.9 Hz, CHCH$_2$OCH$_2$), 3.47 (1H, dd J=4.0, J=9.1 Hz, CHCH$_2$OCH$_2$), 3.09 (1H, dd J=9.2, J=13.4 Hz, CHCH$_2$Ar), 2.86 (1H, dd J=3.7, J=13.6 Hz, CHCH$_2$Ar), 1.62-1.47 (3H, m, CHCH$_2$CH(CH$_3$)$_2$, CHCH$_2$CH(CH$_3$)$_2$), 1.46 (9H, s, C(CH$_3$)$_3$), 0.88 (6H, t J=6.5 Hz, CHCH$_2$CH(CH$_3$)$_2$).

¹³C NMR (75 MHz, CDCl₃) 171.0, 170.7, 170.1, 156.5, 155.2, 130.9, 130.1, 128.3 (2C), 115.1, 79.8, 70.7, 68.4, 67.0, 55.2, 52.6, 51.9, 51.4, 41.9, 37.3, 28.3, 24.4, 22.7, 22.2.

HRMS (ES) 548.2977 (MH⁺). $C_{28}H_{42}N_3O_8$ requires 548.2972.

15S-tert-Butoxycarbonylamino-12S-isobutyl-11,14-dioxo-2,7-dioxa-10,13-diaza-bicyclo[15.2.2]heneicosa-1(20),17(21),18-triene-9R-carboxylic acid methyl ester (78)

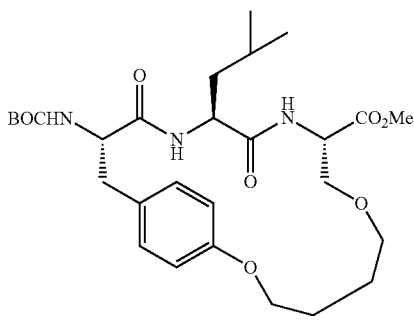

The olefin 77 (100 mg, 0.18 mmol) was dissolved in methanol and 20% (w/w) of 10% palladium on carbon catalyst was added. The mixture was subjected to hydrogenation at rt and atmospheric pressure for 18 h. The mixture was filtered through celite and concentrated in vacuo to afford a white solid, 75 mg, 75%. m.p. 181-183° C. $[\alpha]_D=-0.30$ (c 1, CHCl₃).

¹H NMR (500 MHz in CDCl₃) 7.14 (2H, d J=8.0 Hz, o-Tyr), 6.78 (2H, d J=8.3 Hz, m-Tyr), 6.23 (1H, d J=7.6 Hz, Ser NH), 5.91 (1H, d J=6.8 Hz, Leu NH), 5.31 (1H, d J=8.4 Hz, Tyr NH), 4.66 (1H, m, Ser α-H), 4.25 (1H, m, Tyr α-H), 4.17 (2H, m, Leu α-H, Tyr OCH₂CH₂), 4.04 (1H, td J=5.3, J=5.3, 10.7 Hz, Tyr OCH₂CH₂), 3.77 (3H, s, OCH₃), 3.61 (2H, s, CHCH₂OCH₂), 3.55 (1H, m, Tyr OCH₂CH₂CH₂CH₂O), 3.46 (1H, m, Tyr OCH₂CH₂CH₂CH₂O), 3.02 (1H, dd J=4.4, J=13.0 Hz, CHCH₂Ar), 2.88 (1H, t J=11.9 Hz, CHCH₂Ar), 1.90-1.61 (4H, m, Tyr OCH₂CH₂CH₂CH₂O, CHCH₂CH(CH₃)₂), 1.62-1.48 (3H, m, Tyr OCH₂CH₂CH₂CH₂O, CHCH₂CH(CH₃)₂), 1.45 (9H, s, C(CH₃)₃), 0.87 (6H, s CHCH₂CH(CH₃)₂).

¹³C NMR (75 MHz in CDCl₃) 171.1, 170.4, 170.3, 156.8, 155.1, 130.1, 128.3, 115.3, 79.7, 71.3, 70.0, 67.1, 56.2, 53.0, 52.5, 51.9, 42.4, 38.1, 28.2, 25.0, 24.7, 24.4, 22.7, 22.3.

HRMS (ES) 550.3115 (MH⁺). $C_{28}H_4N_3O_8$ requires 550.3128.

Scheme 19

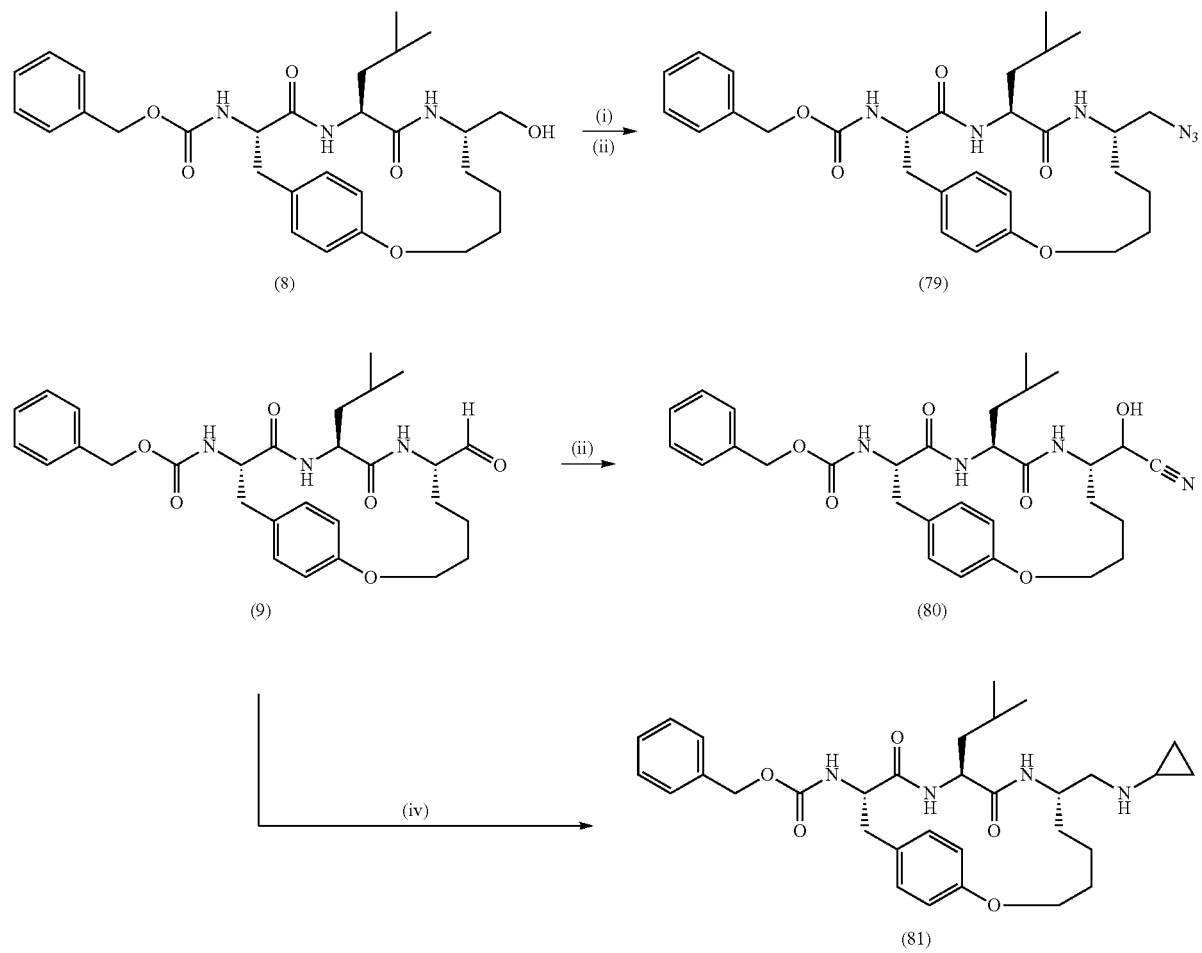

Reagents and Conditions: (i) Et₃N, MSCl, 9, DCM; (ii) NaN₃, DMF (61% for steps (i) and (ii)); (iii) NaHSO₃, KCN (81%); (iv) cyclopropylamide, NaBH(OAc)₃, (61%).

(7S-azidomethyl-10S-isobutyl-9,12-dioxo-2-oxa-8,11-diazabicyclo-[13.2.2]nonadeca-1(18),15(19),16-trien-13S-yl)carbamic acid benzyl ester (79)

[7-(R,S)-(cyanohydroxymethyl)-10S-isobutyl-9,12-dioxo-2-oxa-8,11-diaza-bicyclo-[13.2.2]nonadeca-1(18),15(19),16-trien-13S-yl]carbamic acid benzyl ester (80)

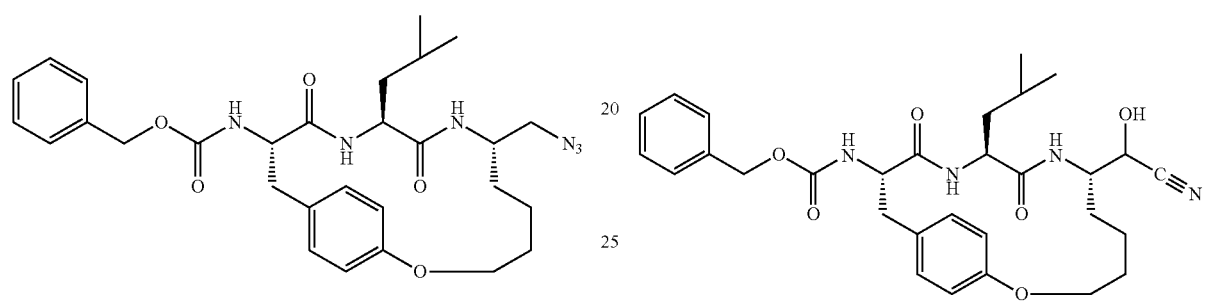

To the macrocyclic alcohol 8 (0.19 g, 0.36 mmol, 1.0 equiv) in dichloromethane was added triethylamine (120 µL, 0.90 mmol, 2.5 equiv) and mesyl chloride (16 µL, 0.36 mmol, 1.0 equiv). The reaction mixture was stirred at rt overnight, then the solvent removed in vacuo. The residue was dissolved in DMF and sodium azide (0.02 g, 0.36 mmol, 1.0 equiv) added and the reaction mixture stirred at rt for 4 h after which it was diluted with EtOAc. The organic phase was washed with brine, dried over MgSO₄ and solvent removed under reduced pressure to give the crude material. Recrystallisation from EtOAc/petroleum ether afforded the product as a white solid, 0.12 g, 61%. m.p. >250° C. $[\alpha]_D$=−3.0 (c 0.1, (CH₃)₂SO).

¹H NMR (500 MHz in (CD₃)₂SO) 7.55 (1H, d J=9.1 Hz, NH), 7.52 (1H, d J=7.1 Hz, NH), 7.38-7.35 (5H, m, Ar—H (Cbz)), 7.01 (2H, d J=7.5 Hz, Ar—H (o-Tyr)), 6.93 (1H, d J=7.7 Hz, NH), 6.74 (2H, d J=8.1 Hz, Ar—H (m-Tyr), 5.03 (2H, q$_{AB}$, J=12.6 Hz CCH₂O), 4.59-4.57 (1H, m, CHCH₂Ph), 4.34-4.29 (2H, m, OCH₂CH₂CH₂CH₂ and CHCH₂N₃), 4.06-4.01 (2H, m, OCH₂CH₂CH₂CH₂ and CHCH₂CH(CH₃)₂), 3.18-3.14 (1H, m, CHCH₂Ph), 3.08-3.03 (1H, m, CHCH₂Ph), 2.86 (1H, dd J=5.6, J=13.1 Hz, CHCH₂N₃), 2.62-2.60 (1H, m, CHCH₂N₃), 1.77-1.68 (2H, m, CHCH₂CH(CH₃)₂), 1.52-1.44 (2H, m, OCH₂CH₂CH₂CH₂), 1.33-1.14 (4H, m, OCH₂CH₂CH₂CH₂ and CHCH₂CH(CH₃)₂), 0.87-0.82 (1H, m, OCH₂CH₂CH₂CH₂), 0.80-0.77 (6H, m, CHCH₂CH(CH₃)₂), 0.64-0.59 (1H, m, OCH₂CH₂CH₂CH₂).

¹³C NMR (75 MHz in (CD₃)₂SO) 170.92, 169.90, 156.54, 155.80, 137.46, 130.45, 128.72, 128.60, 128.03, 115.03, 66.77, 65.65, 64.47, 56.62, 51.13, 49.60, 43.63, 37.38, 30.26, 28.28, 24.24, 23.27, 23.12, 22.35.

$\nu_{max}$ (KBr) 2955 (C(O)NH), 2864 (C(O)NH), 2783 (C(O)NH), 2406 (CH₂N₃), 1701 (OC(O)).

To a cooled solution (5° C.) of the macrocyclic aldehyde 9 (0.50 g, 0.96 mmol, 1 equiv) in methanol was added a cooled (5° C.) aqueous solution of sodium hydrogen sulfite (1.0 equiv). The solution was stirred for 16 h at 4° C. then potassium cyanide (1.0 equiv) in EtOAc added. The biphasic reaction mixture was stirred for 4 h at rt. The organic layer was separated and the aqueous phase was extracted (×2) with EtOAc. The separated organic phases were combined, washed with distilled water, dried over MgSO₄ and the solvent removed to yield the cyanohydrin 80 (0.43 g, 81%) as a mixture of diastereoisomers (1:1).

¹H NMR (500 MHz in (CD₃)₂SO) 7.99 (1H, d J=8.7 Hz, NH), 7.90 (1H, d J=9.5 Hz, NH), 7.52 (1H, d J=7.4 Hz, NH), 7.35 (10H, s, Ar—H (Cbz)), 7.31 (1H, d J=5.5 Hz, NH), 7.07 (1H, d J=8.3 Hz, NH), 7.03-6.99 (4H, m, Ar—H (o-Tyr)), 6.96 (1H, d J=8.1 Hz, NH), 6.76 (4H, d J=7.8 Hz, Ar—H (m-Tyr), 6.61 (1H, d J=6.9 Hz CHCHOH), 6.55 (1H, d J=5.8 Hz CHCHOH), 5.08-4.99 (4H, m, CCH₂O), 4.37-4.29 (4H, m, CHCH₂Ph and OCH₂CH₂CH₂CH₂), 4.13-4.10 (1H, m, CHCH₂CH(CH₃)₂), 4.08-4.01 (3H, m, CHCH₂CH(CH₃)₂ and OCH₂CH₂CH₂CH₂), 3.98-3.94 (2H, m, OCH₂CH₂CH₂CH₂), 3.89-3.85 (2H, m, CHCHOH), 2.85 (2H, dd J=5.2, J=13.1 Hz, CHCH₂Ph), 2.64-2.58 (2H, m, CHCH₂Ph), 1.76-1.67 (2H, m, OCH₂CH₂CH₂CH₂), 1.61-1.45 (4H, m, CHCH₂CH(CH₃)₂ and OCH₂CH₂CH₂CH₂), 1.37-1.12 (10H, m, CHCH₂CH(CH₃)₂ and CHCH₂CH(CH₃)₂ and OCH₂CH₂CH₂CH₂ and OCH₂CH₂CH₂OCH₂CH₂CH₂CH₂), 0.84-0.75 (14H, m, CHCH₂CH(CH₃)₂ and OCH₂CH₂CH₂CH₂).

¹³C NMR (75 MHz in (CD₃)₂SO) 171.19, 170.91, 169.41, 156.13, 155.76, 155.25, 137.10, 130.03, 128.21, 127.65, 127.58, 119.86, 119.33, 115.39, 115.34, 115.30, 66.18, 66.14, 65.11, 65.06, 63.40, 62.85, 56.04, 55.93, 50.54, 50.50, 49.95, 49.74, 43.46, 43.43, 43.34, 43.28, 37.06, 30.02, 29.17, 28.13, 27.52, 27.18, 23.88, 23.63, 22.91, 22.77, 22.60, 21.68, 21.53.

HRMS (ES) 551.2876 (MH$^+$). $C_{30}H_{39}N_4O_6$ requires 551.2870;

$v_{max}$ (KBr) 3319 (CH(OH)), 3064 (C(O)NH), 2922 (C(O)NH), 1882 (CH(OH)CN).

((7S,10S,13S)-7-Cyclopropylaminomethyl-10-isobutyl-9,12-dioxo-2-oxa-8,11-diaza-bicyclo[13.2.2]nonadeca-1(18),15(19),16-trien-13-yl)-carbamic acid benzyl ester (81)

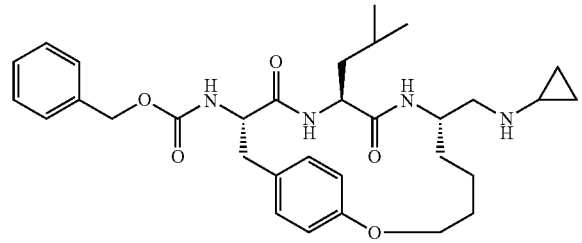 [SMILES: CC(C)C[C@@H]1NC(=O)[C@@H](NC(=O)OCc2ccccc2)Cc2ccc(cc2)OCCCC[C@@H](CNC2CC2)NC1=O]

Cyclopropylamine (29 µL, 0.42 mmol, 1.1 equiv.) was added to a stirred solution of the macrocyclic aldehyde 9 (200 mg, 0.38 mmol, 1.0 equiv.) in freshly distilled 1,2-dichloroethane under a nitrogen atmosphere and stirred for 30 mins, at which time NaBH(OAc)$_3$ (113 mg, 0.53 mmol, 1.4 equiv.) was added portionwise. After stirring for a further 22 h, the cloudy reaction mixture was quenched with saturated aqueous NaHCO$_3$, extracted with dichloromethane, washed with brine, dried (MgSO$_4$), and concentrated in vacuo. Flash chromatography on activated alumina (eluting with 1.5% to 2% methanol in DCM) gave 81 as a white solid, 147 mg, 68%. R$_f$ 0.29 (2% methanol in DCM, alumina). m.p. 208° C. (dec.).

$^1$H NMR (500 MHz in (CD$_3$)$_2$SO) 0.89-0.92 (m, 6H, CH$_2$CH(CH$_3$)$_2$), 1.20-1.29 (m, 1H, CH$_2$CH$_2$CH$_2$O), 1.31-1.36 (m, 1H, CH$_2$CH$_2$O), 1.38-1.45 (m, 4H, CH$_2$CH(CH$_3$)$_2$ and CH$_2$CH$_2$CH$_2$O), (m, 3H, CH$_2$CH(CH$_3$)$_2$ and CH$_2$CH$_2$CH$_2$CH$_2$O), 1.77-1.86 (m, 1H, NHcyclopropyl), 2.07-2.09 (m, 1H, CH$_2$NHcyclopropyl), 2.50-2.51 (m, 1H, CH$_2$NHcyclopropyl), 2.71 (t J=12.19 Hz, 1H, CH$_2$C$_6$H$_4$O), 2.96 (dd J=12.86, J=5.53 Hz, 1H, CH$_2$C$_6$H$_4$O), 3.80-3.87 (m, 1H, CHCH$_2$NHcyclopropyl), 4.00-4.02 (CHCH$_2$CH(CH$_3$)$_2$), 4.12-4.16 (m, 1H, CH$_2$O), 4.37-4.44 (m, 2H, Cbz NHCH and CH$_2$CO), 5.13 (q, J=12.75 Hz, 1H, Cbz CH$_2$), 6.85 (d J=8.30 Hz, 1H, CH$_2$CO), 6.99 (d J=8.30 Hz, 1H, CbzNHCHCOCH), 7.11 (d J=7.06 Hz, 1H, CH$_2$CH$_2$CO), 7.41-7.18 (m, 5H, Cbz Ar—H), 7.61 (d J=7.17 Hz, 1H, Cbz NH), 7.65 (d J=9.16 Hz, 1H, CONH).

$^{13}$C NMR (75 MHz in (CD$_3$)$_2$SO) 17.5, 17.7, 18.7, 18.9, 21.5, 21.6, 22.2, 22.4, 24.6, 30.8, 42.1, 49.5, 61.3, 66.6, 127.6, 127.8, 127.8, 128.0, 128.0, 128.2, 128.5, 137.0, 147.4, 147.7, 157.4, 161.3, 172.4, 172.4.

HRMS 565.3375 [MH$^+$]. $C_{32}H_{45}N_4O_5$ requires 565.3390.

Scheme 20

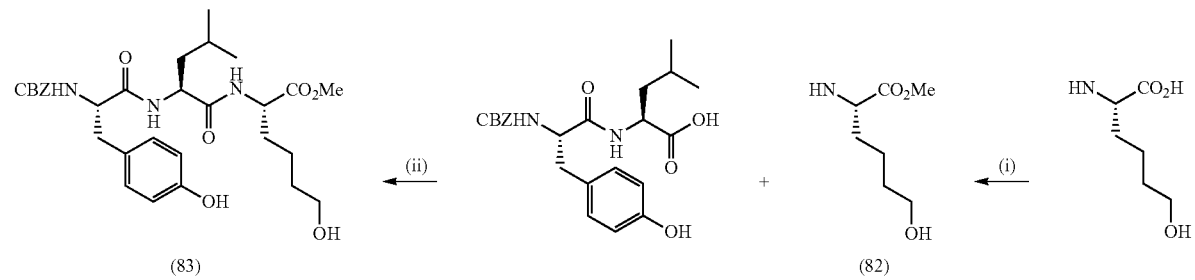

Reagents and Conditions: (i) SO$_2$Cl, MeOH (99%); (ii) EDC.HCl, HOBt, DIPEA, DMF, (76%).

(S)-2-Amino-6-hydroxy-hexanoic acid methyl ester (82)

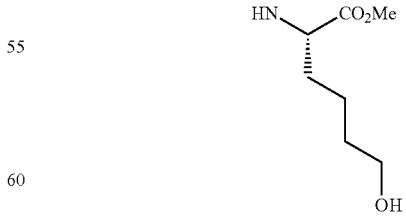

(S)-2-Amino-6-hydroxy-hexanoic acid (Chemstep) (5.54 mmol, 1.37 g) was dissolved in 100 mL of MeOH and cooled at 0° C. SOCl$_2$ (13.8 mmol, 1 mL, 2.5 eq) was added dropwise. The reaction mixture was stirred overnight at room temperature after which time the solvent was removed in vacuo. The crude solid was recrystallised from MeOH (3×100) to give the methyl ester 82 as an oil (5.52 mmol, 0.89 g, 99%).

(S)-6-Hydroxy-2-{(S)-2-[(S)-3-(4-hydroxy-phenyl)-2-methyl-propionylamino]-4-methyl-pentanoylamino}-hexanoic acid methyl ester (83)

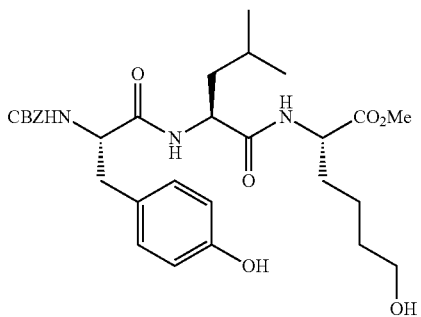

To a suspension of (S)-2-[(S)-2-benzyloxycarbonylamino-3-(4-hydroxy-phenyl)-propionyl-amino]-4-methyl pentanoic acid (Bachem) (5.44 mmol, 1.36 g, 1 eq) and methyl ester 82 (5.44 mmol, 0.91 g) in DMF was added HATU (5.98 mmol, 1.41 g, 1.1 eq). DIPEA (0.12 mol, 1.62 g, 2.1 eq) was added and the reaction mixture was stirred at room temperature overnight. EtOAc (100 mL) was added the mixture was washed with 1M hydrochloric acid, saturated aqueous NaHCO$_3$ and brine. The organic layer was dried over MgSO$_4$ and the solvent was removed in vacuo. The crude product was purified by recrystallisation from EtOAc to provide diol 83 as an oil (2.39 g, 76%).

Alternative Ring Closing Methods

The ring closing metathesis of dienes 70, 3, 22, 76 and 74 was examined both thermally and under microwave promoted conditions. The effect of the addition of the Lewis acid chloro-dicyclohexyl borane on the stereochemical outcome of the ring closing metathesis both thermally and under microwave promoted conditions was also examined. The reactions were performed under the following conditions:

A. Thermal reflux: to a solution of diene in anhydrous 1,1,2-trichloroethane (0.01M) under an inert atmosphere was added Grubb's second generation catalyst (10 mol %) and heated to reflux. After 1 hour a second portion of catalyst (10 mol %) was added and heated for another hour before the final portion (10 mol %) was added. The reaction mixture was heated at reflux for a further 16 hours, cooled, stirred overnight with activated charcoal, filtered and concentrated in vacuo.

B. Microwave reflux: to a solution of diene in anhydrous 1,1,2-trichloroethane (0.01M) under an inert atmosphere was added Grubb's second generation catalyst (10 mol %) and heated for 20 minutes in a microwave (1200 W, 110-115° C.). Two more portions of catalyst (2×10 mol %) were added with 20 minutes heating between each addition. The reaction mixture was cooled, stirred overnight with activated charcoal, filtered and concentrated in vacuo.

C. Thermal reflux with Lewis acid: to a solution of diene in anhydrous 1,1,2-trichloroethane (0.01M) under an inert atmosphere was added Grubb's second generation catalyst (10 mol %) and chlorodicyclohexyl borane (1M solution in hexane, 10 mol %) then heated to reflux. After 1 hour a second portion of catalyst (10 mol %) was added and heated for another hour before the final portion (10 mol %) was added. The reaction mixture was heated at reflux for a further 16 hours, cooled, stirred overnight with activated charcoal, filtered and concentrated in vacuo.

D. Microwave reflux with Lewis acid: to a solution of diene in anhydrous 1,1,2-trichloroethane (0.01M) under an inert atmosphere was added Grubb's second generation catalyst (10 mol %) and chlorodicyclohexyl borane (1M solution in hexane, 10 mol %) then heated for 20 minutes in a microwave (1200 W, 110-115° C.). Two more portions of catalyst (2×10 mol %) were added with 20 minutes heating between each addition. The reaction mixture was cooled, stirred overnight with activated charcoal, filtered and concentrated in vacuo.

The stereochemical outcome of the ring closing metathesis (RCM) under the different conditions and the yield of unsaturated macrocycles 71, 4, 23, 77 and 74 is detailed in Table 1.

TABLE 1[a]

| Diene | RCM | Product | Ring Size | Geometric isomer ratio E:Z[a] | Yield (%) |
|---|---|---|---|---|---|
| (structure 70) | A | (structure 71[b]) | 16 | 6:1 | 49 |
|  | B |  |  | >19:1 | 58 |
|  | C |  |  | >19:1 | 50 |
|  | D |  |  | >19:1 | 48 |

TABLE 1[a]-continued

| Diene | RCM | Product | Ring Size | Geometric isomer ratio E:Z[a] | Yield (%) |
|---|---|---|---|---|---|
| 3 | A B C D | 4[b,c] | 17 | 9:1 9:1 9:1 9:1 | 22 43 82 91 |
| 22 | A B C D | 23[e] | 18 | 1:1.7[d] 1:1.7[d] 1:1.7[d] 1:1.9 | 51 58 74 100 |
| 76 | A B C D | 77[b] | 19 | 6:1[d] 4:1[d] 5:1[d] >19:1 | 22 24 30 33 |

TABLE 1ᵃ-continued

| Diene | RCM Product | Ring Size | Geometric isomer ratio E:Zᵃ | Yield (%) |
|---|---|---|---|---|
| 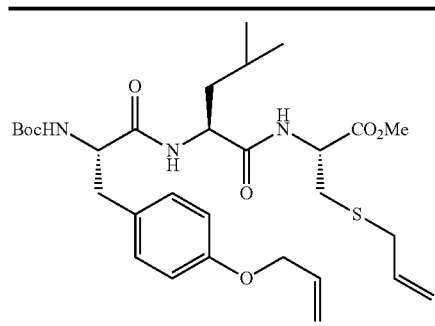 73 | 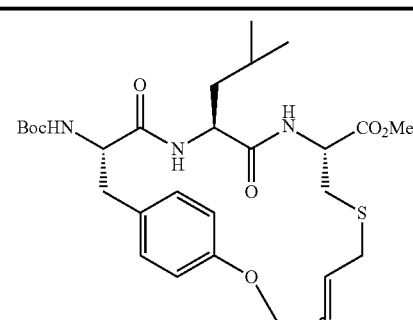 74ᵉ <br> A <br> B <br> C <br> D | 20 | 9:1 <br> 9:1 <br> >19:1 <br> >19:1 | 41 <br> 42 <br> 45 <br> 40 |

ᵃRatios measured using NMR integrals.
ᵇMajor geometric isomers assigned by NMR J coupling constants.
ᶜMajor geometric isomers unambiguously assigned by X-ray crystallography.
ᵈThree macrocyclic products were isolated from the RCM reaction of this diene. Two products were unambiguously assigned the structure of the desired cis and trans olefins. The NMR data of the third products clearly suggested double bond migration.
ᵉMajor geometric isomers assigned by NOE experiments.

Enzyme Specificity

The inhibitors were assayed against several enzymes using a BODIPY-casein substrate in the fluorescence-based assay procedure of V. F. Thompson, S. Saldana, J. Cong and D. E. Goll, *Anal. Biochem.* 2000, 279, 170. The results of these assays are presented in Table 2

TABLE 2

| | $IC_{50}$ | | | | | |
|---|---|---|---|---|---|---|
| Compound | calpain I (μ calpain) | calpain II (m calpain) | cathepsin B | pepsin | α-chymotrypsin | papain |
| 8 | 1750 nM | 700 nM | 290 nM | >50000 nM | >50000 nM | >50000 nM |
| 9 | 223 nM | 30 nM | 70 nM | >25000 nM | >50000 nM | >50000 nM |
| 27 | 1340 nM | 1100 nM | 1100 nM | >20000 nM | >50000 nM | >50000 nM |
| 28 | 170 nM | 180 nM | 770 nM | >50000 nM | >50000 nM | >50000 nM |
| 79 | >50000 nM | >50000 nM | >50000 nM | >50000 nM | >50000 nM | >50000 nM |
| 80 | 35000 nM | 8900 nM | 2400 nM | >50000 nM | >50000 nM | 12000 nM |

Enzyme Inhibition

A number of the compounds were assayed against m-calpain using a BODIPY-casein substrate in the fluorescence-based assay procedure of V. F. Thompson, S. Saldana, J. Cong and D. E. Goll, *Anal. Biochem.* 2000, 279, 170. The results of these assays are presented in Table 3.

The results of the enzyme inhibition assay for (7S,10S,13S)-7-formyl-10-isobutyl-9,12-dioxo-2-oxa-8,11-diaza-bicyclo[13.2.2]nonadeca-1(18),15(19),16-trien-13-yl)-carbamic acid benzyl ester (9) are graphically represented in FIG. 1 for which y=30.924x+97.63 and $R^2$=0.8554.

TABLE 3

| Cmpd | A | $R_2$ | $R_3$ | $R_{20}$ | $R_5$ | $R_6$ | $IC_{50}$ |
|---|---|---|---|---|---|---|---|
| 9 | C(=O)$R_5$ | Leu | CHO | butyl | benzyloxy | — | 30 nM |
| 28 | C(=O)$R_5$ | Leu | CHO | pentyl | benzyloxy | — | 180 nM |
| 50 | C(=O)$R_5$ | Val | CHO | butyl | benzyloxy | — | 40 nM |
| 52 | C(=O)$R_5$ | Leu | CHO | butyl | pyrrolyl | — | 690 nM |
| 17 | S(=O$_2$)$R_6$ | Leu | CHO | butyl | — | 4F-Ph | 45 nM |
| 54 | S(=O$_2$)$R_6$ | Val | CHO | butyl | — | 4F-Ph | 280 nM |
| 69 | S(=O$_2$)$R_6$ | Val | CHO | propyl | — | 4F-Ph | 3710 nM |
| 56 | S(=O$_2$)$R_6$ | Val | CHO | butyl | — | Me | 950 nM |
| 36 | C(=O)$R_5$ | Val | CHO | (CH$_2$)$_4$SCH$_2$ | benzyloxy | — | 295 nM |
| 58 | S(=O$_2$)$R_6$ | Val | CHO | (CH$_2$)$_4$SCH$_2$ | — | 4F-Ph | 2400 nM |
| 8 | C(=O)$R_5$ | Leu | CH$_2$OH | butyl | benzyloxy | — | 700 nM |
| 27 | C(=O)$R_5$ | Leu | CH$_2$OH | pentyl | benzyloxy | — | 1340 nM |
| 16 | S(=O)$R_6$ | Leu | CH$_2$OH | butyl | — | 4F-Ph | 930 nM |

TABLE 3-continued

| Cmpd | A | $R_2$ | $R_3$ | $R_{20}$ | $R_5$ | $R_6$ | $IC_{50}$ |
|---|---|---|---|---|---|---|---|
| 79 | $C(=O)R_5$ | Leu | $CH_2N_3$ | butyl | benzyloxy | — | >50000 nM |
| 80 | $C(=O)R_5$ | Leu | $C(OH)CN$ | butyl | benzyloxy | — | 8900 nM |
| 81 | $C(=O)R_5$ | Leu | $CH_2NH-C_3H_2$ | butyl | benzyloxy | — | >50000 nM |

In Vitro Lens Culture Assay

The ability of compound 9 to prevent the formation of a calcium induced cataract in adult ovine lens was assayed using the procedure of J. Sanderson, J. M. Marciantonio and G. A. Duncan, *Invest. Opth. Vis. Sci.* 2000, 41, 2255.

Figure 2:
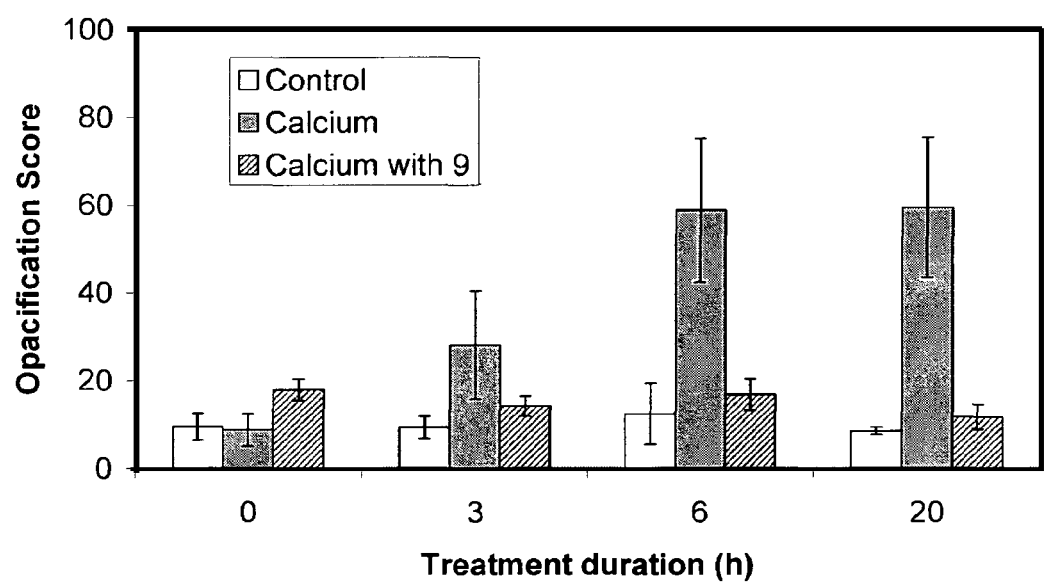
FIG. 2 is a graph of the mean opacification scores against time for normal ovine lenses in EMEM (control), ovine lenses treated with 5 mM calcium in EMEM ($Ca^{2+}$ only) and ovine lenses treated with 5 mM calcium in EMEM containing 1 μM (7S,10S,13S)-7-formyl-10-isobutyl-9,12-dioxo-2-oxa-8,11-diaza-bicyclo[13.2.2]nonadeca-1(18),15(19),16-trien-13-yl)-carbamic acid benzyl ester (9) ($Ca^{2+}$ with 9) during a 20 h experiment.

Six pairs of lenses were tested. One lens from each pair was preincubated with [1 µM] 9 in EMEM-culture media, for 3 h while the other was incubated at 35° C., 5% $CO_2$. Then 5 mM calcium chloride was added onto both the inhibitor treated lens and the other lens, and both lenses were then incubated for 20 h. The lenses were photographed and the images digitally analysed for opacity. The results of these studies are presented in FIG. 2.

Figure 3:
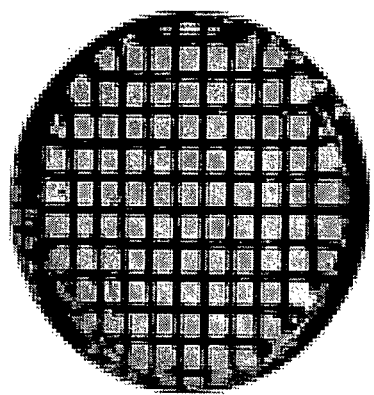
FIG. 3 is a photograph of an ovine lens that was pre-incubated with (7S,10S,13S)-7-formyl-10-isobutyl-9,12-dioxo-2-oxa-8,11-diaza-bicyclo[13.2.2]nonadeca-1(18),15(19),16-trien-13-yl)-carbamic acid benzyl ester (9) before being treated with calcium chloride.
Figure 4:
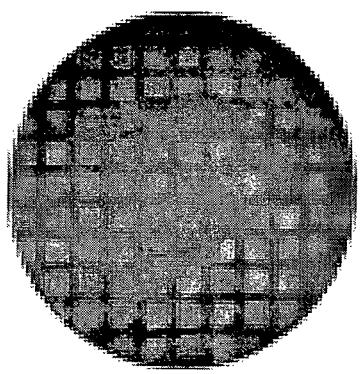
FIG. 4 is a photograph of an ovine lens that was treated with calcium chloride.

A typical pair of lenses was photographed when the assay had been completed. FIG. 3 shows the lens that was preincubated with compound 9 prior to the addition of calcium chloride. FIG. 4 shows the other lens.

In Vivo Tests

An ointment (50 mg) comprising 1% of compound 9 was applied to one eye of a lamb, three times in one day. No sign of irritation was observed and the lamb was then sacrificed.

A flock of 63 lambs genetically predisposed to cataracts were split into three equal groups. An ointment (25 mg) comprising 1% of compound 9 was applied twice daily to the right eye of one of the groups of 21 lambs for three months starting when they were three to four months old. An ointment (25 mg) comprising 1% of compound 8 was applied twice daily to the right eye of another of the groups of 21 lambs for three months starting when they were three to four months old. A placebo ointment (25 mg) was applied twice daily to the right eye of the final group of 21 lambs for three months starting when they were three to four months old.

Figure 5:
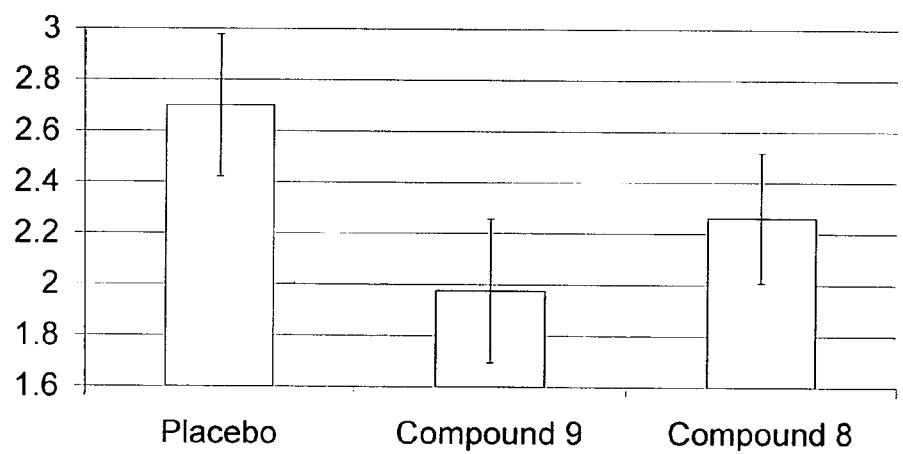
FIG. 5 is a graph of the mean change in eye score over three months for the treatment of three groups of lambs genetically predisposed to cataracts with ointments containing (7S,10S,13S)-7-hydroxymethyl-10-isobutyl-9,12-dioxo-2-oxa-8,11-diaza-bicyclo[13.2.2]-nona-deca-1(18),15(19),16-trien-13-yl)-carbamic acid benzyl ester (8), (7S,10S,13S)-7-formyl-10-isobutyl-9,12-dioxo-2-oxa-8,11-diaza-bicyclo[13.2.2]nonadeca-1(18),15(19),16-trien-13-yl)-carbamic acid benzyl ester (9) or with a placebo ointment.

The progression of cataracts was determined by a veterinary ophthalmologist with a slit-lamp microscope. The treated right eye did not show significantly slower cataract progression than the left eye for any of the three groups. However, cataract progression in both eyes of the animals treated with the ointment containing compound 9 or with the ointment containing compound 8 was significantly slower (p=0.066 and p=0.26, respectively) than the placebo-treated lambs. These results are presented in FIG. 5.

Compound 9 was found to be capable of slowing cortical cataract progression by 30% over a 12 week period in a flock of lambs genetically predisposed to cataracts with no signs of toxicity.

Formulations

Ointment

An ointment, suitable for intraocular application, and having the following composition (w/w) was prepared:
1% compound of Formula I
25% cetyl stearyl alcohol
35% wool fat
39% paraffinum subl.

Cetyl stearyl alcohol was heated until it had melted. The compound of Formula I was added and the oil stirred until the compound had dissolved. Wool fat and paraffinum subl. were added and the mixture was heated until all the components had melted. The mixture was allowed to cool with constant stirring until an ointment had formed.

Emulsion

An emulsion, suitable for intraocular application, and having the following composition (w/w) was prepared according to the procedure described below:
0.7% compound of Formula I
20% cetyl stearyl alcohol
25% wool fat
25% paraffinum subl.
1% sodium lauryl sulfate
0.1% sodium benzoate
28.3% water The hydrophobic phase (cetyl stearyl alcohol, wool fat, paraffinum subl.) and the hydrophilic phase (sodium lauryl sulfate, sodium benzoate, water) were separately heated to 50° C. The compound of Formula I was added to the hydrophobic phase which was stirred until the compound dissolved. The hydrophilic phase was then added to the hydrophobic phase, and the heating source removed. The mixture was stirred until it reached rt. The resulting emulsion was then checked for the absence of crystals by differential scanning calorimetry at the melting point of the compound of Formula I.

Industrial Application

It will be appreciated from the discussion above that this invention provides novel compounds having cysteine protease inhibitory properties, more particularly calpain inhibitory properties. These compounds may be formulated into pharmaceutical compositions for use in any therapeutic application for which their inhibitory activity make them appropriate. Such therapeutic applications include the prevention or treatment of cataracts.

Although the invention has been described by way of example and with reference to particular embodiments, it is to be understood that modifications and/or improvements may be made without departing from the scope of the invention as set out in the accompanying claims.

The invention claimed is:
1. A compound selected from the group consisting of:

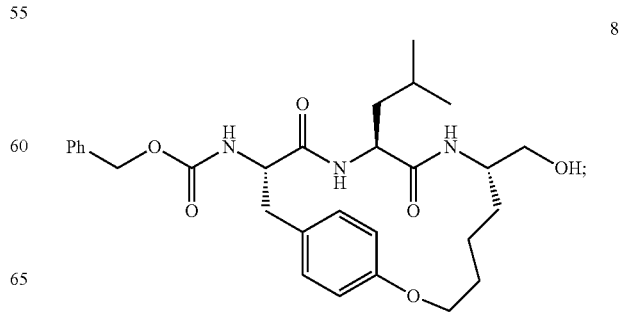

-continued

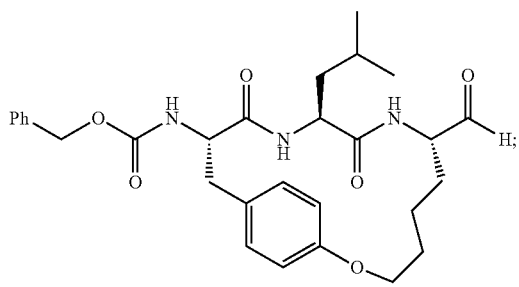

and the pharmaceutically acceptable salts thereof.

2. The compound:

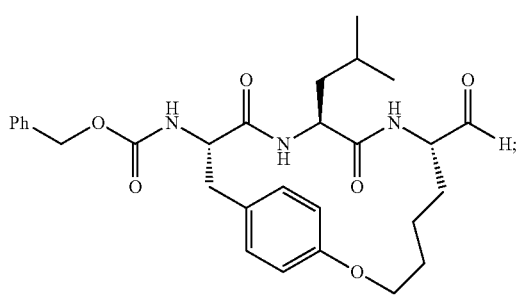

and the pharmaceutically acceptable salts thereof.

3. A pharmaceutical composition comprising a compound as claimed in claim 1 and a pharmaceutically acceptable carrier, diluent or excipient.

4. A method for treating cataracts comprising administering to a patient in need thereof, a therapeutically effective amount of a compound selected from the group consisting of:

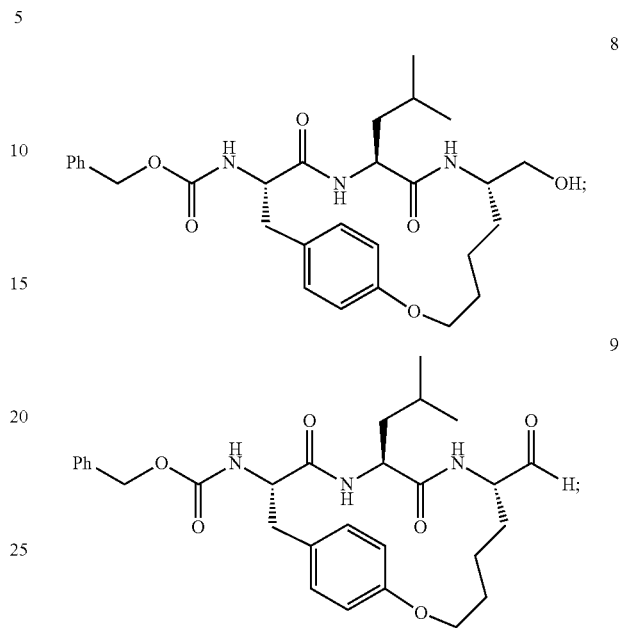

and the pharmaceutically acceptable salts thereof.

5. The method according to claim 4, wherein administration of the compound comprises topical administration to the eye.

* * * * *

UNITED STATES PATENT AND TRADEMARK OFFICE
CERTIFICATE OF CORRECTION

PATENT NO.       : 8,710,178 B2  
APPLICATION NO.  : 12/446053  
DATED            : April 29, 2014  
INVENTOR(S)      : Abell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1328 days.

Signed and Sealed this

Twenty-ninth Day of September, 2015

Michelle K. Lee
*Director of the United States Patent and Trademark Office*